United States Patent
Beazley et al.

(10) Patent No.: US 10,584,391 B2
(45) Date of Patent: *Mar. 10, 2020

(54) SOYBEAN TRANSGENIC EVENT MON87751 AND METHODS FOR DETECTION AND USE THEREOF

(71) Applicant: Monsanto Technology LLC, St. Louis, MO (US)

(72) Inventors: Kim A. Beazley, Kirkwood, MO (US); Wen C. Burns, Chesterfield, MO (US); Robert H. Cole, II, Florissant, MO (US); Ted C. MacRae, Wildwood, MO (US); John A. Miklos, Des Peres, MO (US); Lisa G. Ruschke, St. Louis, MO (US); Kairong Tian, St. Louis, MO (US); Liping Wei, St. Louis, MO (US); Kunsheng Wu, Ballwin, MO (US)

(73) Assignee: Monsanto Technology LLC, St. Louis, MO (US)

( * ) Notice: Subject to any disclaimer, the term of this patent is extended or adjusted under 35 U.S.C. 154(b) by 221 days.

This patent is subject to a terminal disclaimer.

(21) Appl. No.: 15/635,041

(22) Filed: Jun. 27, 2017

(65) Prior Publication Data

US 2017/0362667 A1 Dec. 21, 2017

Related U.S. Application Data

(62) Division of application No. 14/303,042, filed on Jun. 12, 2014, now Pat. No. 9,719,145.

(Continued)

(51) Int. Cl.
*C12N 15/00* (2006.01)
*C12Q 1/6895* (2018.01)

(Continued)

(52) U.S. Cl.
CPC .............. *C12Q 1/6895* (2013.01); *A23D 9/00* (2013.01); *A23J 1/14* (2013.01); *A23K 10/00* (2016.05);

(Continued)

(58) Field of Classification Search
None
See application file for complete search history.

(56) References Cited

U.S. PATENT DOCUMENTS

| | | |
|---|---|---|
| 5,500,365 A | 3/1996 | Fischhoff et al. |
| 6,017,534 A | 1/2000 | Malvar et al. |

(Continued)

FOREIGN PATENT DOCUMENTS

| | | |
|---|---|---|
| JP | 2009-505679 | 2/2009 |
| WO | WO 2000/026371 | 5/2000 |

(Continued)

OTHER PUBLICATIONS

New England BioLabs Inc., 1998/99 Catalog, (NEB Catalog), pp. 121 and 284, accessed Mar. 18, 2015.

(Continued)

*Primary Examiner* — Aaron A Priest
(74) *Attorney, Agent, or Firm* — Dentons US LLP

(57) ABSTRACT

The invention provides a transgenic *Glycine max* event MON87751, plants, plant cells, seeds, plant parts, progeny plants, and commodity products comprising event MON87751. The invention also provides polynucleotides specific for event MON87751, plants, plant cells, seeds, plant parts, and commodity products comprising polynucleotides for event MON87751. The invention also provides methods related to event MON87751.

7 Claims, 6 Drawing Sheets

Specification includes a Sequence Listing.

Related U.S. Application Data

(60) Provisional application No. 61/834,899, filed on Jun. 14, 2013.

(51) Int. Cl.
| | | |
|---|---|---|
| *C12N 15/82* | (2006.01) | |
| *A23J 1/14* | (2006.01) | |
| *A23D 9/00* | (2006.01) | |
| *C12G 1/00* | (2019.01) | |
| *A23K 10/00* | (2016.01) | |
| *A23C 11/10* | (2006.01) | |
| *A23C 20/02* | (2006.01) | |

(52) U.S. Cl.
CPC ........... *C12G 1/00* (2013.01); *C12N 15/8286* (2013.01); *A23C 11/103* (2013.01); *A23C 20/025* (2013.01); *C12Q 2600/13* (2013.01); *C12Q 2600/158* (2013.01); *Y02A 40/162* (2018.01)

(56) References Cited

U.S. PATENT DOCUMENTS

| | | |
|---|---|---|
| 6,489,542 B1 | 12/2002 | Corbin |
| 6,713,063 B1 | 3/2004 | Malvar et al. |
| 7,064,249 B2 | 6/2006 | Corbin |
| 7,070,982 B2 | 7/2006 | Malvar et al. |
| 7,223,907 B2 | 5/2007 | Huber et al. |
| 7,700,830 B2 | 4/2010 | Corbin |
| 7,858,764 B1 | 12/2010 | Huber et al. |
| 8,030,542 B2 | 10/2011 | Corbin |
| 8,034,997 B2 | 10/2011 | Bogdanova |
| 8,049,071 B2 | 11/2011 | Gao et al. |
| 8,062,840 B2 | 11/2011 | Anderson et al. |
| 8,344,207 B2 | 1/2013 | Bogdanova |
| 8,455,198 B2 | 6/2013 | Gao et al. |
| 8,581,047 B2 | 11/2013 | Anderson et al. |
| 9,222,099 B2 | 12/2015 | Chittoor et al. |
| 2007/0074305 A1* | 3/2007 | Eenennaam ....... C12N 15/8216 800/278 |
| 2010/0313310 A1 | 12/2010 | Andersch et al. |
| 2011/0067141 A1 | 3/2011 | Froman et al. |
| 2011/0143346 A1 | 6/2011 | Huber |
| 2011/0321185 A1 | 12/2011 | Anderson et al. |
| 2013/0095488 A1 | 4/2013 | Bogdanova |
| 2014/0189911 A1 | 7/2014 | Anderson et al. |
| 2014/0283200 A1 | 9/2014 | Chittoor et al. |
| 2016/0076047 A1 | 3/2016 | Chittoor et al. |
| 2016/0083740 A1 | 3/2016 | Chittoor et al. |

FOREIGN PATENT DOCUMENTS

| | | |
|---|---|---|
| WO | WO 2007/027777 | 3/2007 |
| WO | WO 2007/140256 | 12/2007 |
| WO | WO 2009/064652 | 5/2009 |
| WO | WO 2011/084629 | 7/2011 |
| WO | WO 2014/159434 | 10/2014 |

OTHER PUBLICATIONS

Weising et al., "Foreign genes in plants: transfer, structure, expression, and applications," *Annu Rev Genet* 22:421-77, 1988.

Final Office Action regarding U.S. Appl. No. 11/801,114, dated Aug. 26, 2009.

Siebert et al., "Evaluation of corn hybrids expressing Cry1F, Cry1A. 105, Cry2Ab2, Cry34Ab1/Cry35Ab1, and Cry3Bb1 against southern United States insect pests," J Economic Entomology 105(5):1825-1834, 2012.

Wu et al., "Susceptibility of Cry1Ab-resistant and -susceptible sugarcane borer (Lepidoptera: Crambidae) to four *Bacillus thuringiensis* toxins," J Invertebrate Pathology 100(1):29-34, 2009.

International Search Report and Written Opinion regarding PCT/US2014/042100, dated Dec. 10, 2014.

GenBank Accession No. M23724, dated Apr. 26, 1993.

Li et al., "Effects of Bt cotton expressing Cry1Ac and Cry2Ab and non-Bt cotton on behavior, survival and development of *Trichoplusia ni* (Lepidoptera: Noctuidae)," *Crop Protection* 25:940-948, 2006.

Macrae et al., "Laboratory and Field Evaluations of Transgenic Soybean Exhibiting High-Dose Expression of a Synthetic Bacillus thuringiensis cry1A Gene for Control of Lepidoptera," *J. Econ. Entomol.* 98(2):577-587, 2005.

Extended European Search Report regarding European Application No. 14810194.2, dated Jan. 5, 2017.

Storer et al., "Application of pyramided traits against Lepidoptera in insect resistance management for Bt Crops," *GM Crops & Food* 3(3):154-162, 2012.

Office Action regarding Chinese Application No. 201480044096, dated Jul. 2, 2018.

Wang et al., "Advances in Transgenic Soybean Resistant to Disease and Pest," *Soybean Science* 30(5):865-868, 2011.

\* cited by examiner

A.

B.

SOYBEAN TRANSGENIC EVENT MON87751 AND METHODS FOR DETECTION AND USE THEREOF

REFERENCE TO RELATED APPLICATIONS

This application is a divisional of U.S. Application Ser. No. 14/303,042, filed Jun. 12, 2014 (pending), which application claims the benefit of United States provisional application No. 61/834,899, filed Jun. 14, 2013, both of which disclosures of which are herein incorporated by reference in their entirety.

INCORPORATION OF SEQUENCE LISTING

The Sequence listing contained in the file named MONS357US_ST25.txt, which is 42.9 kilobytes (size as measured in Microsoft Windows®), and was created on May 28, 2014, is filed herewith by electronic submission and is incorporated by reference herein.

FIELD OF THE INVENTION

The invention relates to a transgenic *Glycine max* (soybean) event referred to as MON87751. The event provides two different modes of action of resistance from lepidopteran infestations of soybean by providing a unique combination of insecticidal toxin proteins not previously available in soybean plants. The combination of these insecticidal toxin proteins is highly efficacious for controlling lepidopteran species infestations characteristic to soybean plants. The invention also relates to soybean plants, plant parts, plant seeds, plant cells, progeny plants, agricultural products, and methods related to event MON87751, and provides nucleotide molecules that are unique to the event, created in connection with the insertion of transgenic DNA into the genome of a *Glycine max* (soybean) cell, and useful for detecting the presence of this event in biological samples containing soybean nucleic acids.

BACKGROUND OF THE INVENTION

Soybean (*Glycine max*) is an important crop in many areas of the world, and biotechnology methods have been applied to this crop in order to produce soybean varieties with desirable traits. One such desirable trait is insect resistance. The expression of an insect resistance transgene in a plant can confer the desirable trait of insect resistance on the plant, but expression of the transgene may be influenced by many different factors including the orientation and composition of the cassettes driving expression of the individual genes transferred to the plant chromosome, the chromosomal location, and the genomic result of the transgene insertion. For example, it has been observed in plants that there is variation in the level and pattern of transgene expression among individual events that differ in the chromosomal insertion site of the transgene but are otherwise identical. There are also undesirable and/or desirable phenotypic or agronomic differences between events. Therefore, it is often necessary to produce and analyze a large number of individual plant cell transformation events in order to select an event having both the desirable trait and the optimal phenotypic and agricultural characteristics suitable for commercial success. Selecting the preferred transgenic event requires extensive molecular characterization, as well as greenhouse and field trials with many events over multiple years, in multiple locations, and under a variety of conditions. A significant amount of efficacy, phenotypic, and molecular data is collected, and the resulting data and observations are then analyzed by teams of scientists and agronomists with the goal of selecting one or more commercially suitable events. Such an event, once selected, is then used for introgression of the desirable transgenic trait into other genetic backgrounds using plant breeding methods, thus producing a number of different crop varieties that contain the desirable trait and are suitably adapted to specific local agronomic conditions.

Transgenic soybeans which rely upon expression of a single toxin for insecticidal control of insect infestation may be at risk of limited durability because of the increased likelihood of development of resistance to the toxin by the insect pests. Similarly, transgenic soybeans containing toxic agents that do not provide multiple unique modes of action could also be at risk of limited durability. The first available soybean that produces a protein toxic to lepidopterans contains a single toxin protein, Cry1Ac. A recent soybean transgenic event has been disclosed that contains Cry1Ac and Cry1F toxin proteins. If resistance to Cry1Ac occurs, the Cry1Ac and Cry1F transgenic event would be left with only the Cry1F toxin as its source of efficacy. It is therefore necessary to provide for a soybean plant that has two or more toxic agents that control the pests controlled by Cry1Ac in which none of the toxic agents bind the same or substantially the same receptors in the target insect midgut that are bound by Cry1Ac. The invention described herein provides for a transgenic soybean event MON87751 that overcomes the durability problem described above for the soybean transgenic events described in the prior art, by providing two or more agents toxic to lepidopteran pest species, in which neither toxic agent has previously been included in any soybean plant for the purpose of targeting for control the lepidopteran pests of soybean.

To make a transgenic plant containing a single transformation event, a portion of a recombinant DNA construct is transferred into the genome of a soybean cell, and the soybean cell is subsequently grown into a plant. A soybean cell into which the event is initially transferred is regenerated to produce the R0 generation. The R0 plant and progeny plants from the R0 plant can be tested for any desired trait(s), but the effectiveness of the event can be impacted by cis and/or trans factors relative to the integration site in the transformation event. The phenotype conferred by the event can also be impacted by the size and design of the DNA construct, which can vary by the combination of genetic elements in an expression cassette, number of transgenes, number of expression cassettes, and configuration of such elements and such cassettes. Identifying an event with desirable traits can be further complicated by factors such as plant developmental, diurnal, temporal, or spatial patterns of transgene expression; or by extrinsic factors, e.g., environmental plant growth conditions, water availability, nitrogen availability, heat, or stress. Thus, the ability to obtain an event conferring a desirable set of phenotypic traits is not readily predictable.

SUMMARY OF THE INVENTION

The invention provides transgenic soybean plants comprising event MON87751 exhibiting superior properties and performance compared to existing transgenic soybean plants and to new events constructed in parallel. The soybean event MON87751 contains, at a single locus of insertion in the soybean genome, two linked expression cassettes which independently confer the trait of resistance to lepidopteran insect pests. Combined the two linked expression cassettes in soybean event MON87751 provide two modes of action against insect pest species in the order Lepidoptera, including *Chrysodeixis* spp., *Spodoptera* spp., *Helicoverpa* spp., *Crocidosema* spp., *Rachiplusia* spp., *Anticarsia* spp., *Elasmopalpus* spp., and *Plathypena* spp. The dual modes of action provide redundancy of insecticidal control against lepidopteran pest species, and significantly reduces the likelihood of the development of resistance to the pest control traits.

The event MON87751 is characterized by specific unique DNA segments that are useful in detecting the presence of the event in a sample. A sample is intended to refer to a composition that is either substantially pure soybean DNA or a composition that contains soybean DNA. In either case, the sample is a biological sample, i.e., it contains biological materials, including but not limited to DNA obtained or derived from, either directly or indirectly, from the genome of soybean comprising event MON87751. "Directly" refers to the ability of the skilled artisan to directly obtain DNA from the soybean genome by fracturing soybean cells (or by obtaining samples of soybean that contain fractured soybean cells) and exposing the genomic DNA for the purposes of detection. "Indirectly" refers to the ability of the skilled artisan to obtain the target or specific reference DNA, i.e. a novel and unique junction segment described herein as being diagnostic for the presence of the event MON87751 in a particular sample, by means other than by direct via fracturing of soybean cells or obtaining a sample of soybean that contains fractured soybean cells. Such indirect means include, but are not limited to, amplification of a DNA segment that contains the DNA sequence targeted by a particular probe designed to bind with specificity to the target sequence, or amplification of a DNA segment that can be measured and characterized, i.e. measured by separation from other segments of DNA through some efficient matrix such as an agarose or acrylamide gel or the like, or characterized by direct sequence analysis of the amplicon or cloning of the amplicon into a vector and direct sequencing of the inserted amplicon present within such vector. Alternatively, a segment of DNA corresponding to the position within the soybean chromosome at which the transgenic DNA was inserted into the soybean chromosome and which can be used to define the event MON87751, can be cloned by various means and then identified and characterized for its presence in a particular sample or in a particular soybean genome. Such DNA segments are referred to as junction segments or sequences, and can be any length of inserted DNA and adjacent (flanking) soybean chromosome DNA so long as the point of joining between the inserted DNA and the soybean genome is included in the segment. SEQ ID NO:1, SEQ ID NO:2, SEQ ID NO:3, SEQ ID NO:4, SEQ ID NO:5, SEQ ID NO:6, SEQ ID NO:7, SEQ ID NO:8, and SEQ ID NO:10 and the reverse complement of each of these, are representative of such segments.

The specific sequences identified herein may be present uniquely in event MON87751, or the construct comprised therein, and the identification of these sequences, whether by direct sequence analysis, by detecting probes bound to such sequences, or by observing the size and perhaps the composition of particular amplicons described herein, when present in a particular soybean germplasm or genome and/or present in a particular biological sample containing soybean DNA, are diagnostic for the presence of the event MON87751, or the construct comprised therein, in such sample. It is known that the flanking genomic segments (i.e., the soybean genome segments of DNA sequence adjacent to the inserted transgenic DNA) are subject to slight variability and as such, the limitation of at least 99% or greater identity is with reference to such anomalies or polymorphisms from soybean genome to soybean genome. Nucleotide segments that are completely complementary across their length in comparison to the particular diagnostic sequences referenced herein are intended to be within the scope of the present invention.

The position of the nucleotide segments of the present invention relative to each other and within the soybean genome are illustrated in FIG. 1 and the nucleotide sequence of each is illustrated as set forth in SEQ ID NO:10. Nucleotide segments that characterize the event MON87751 and which are diagnostic for the presence of event MON87751, or the construct comprised therein, in a sample include SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, or SEQ ID NO:26. The presence of one, or two, or more of these nucleotide sequences in a sample, when such sample contains soybean tissue and thus soybean DNA, are diagnostic for the presence of the event MON87751, or the construct comprised therein.

It is intended by use of the word "derived", that a particular DNA molecule is in the soybean plant genome, or is capable of being detected in soybean plant DNA. "Capable of being detected" refers to the ability of a particular DNA segment to be amplified and its size and or sequence characterized or elucidated by DNA sequence analysis, and can also refer to the ability of a probe to bind specifically to the particular DNA segment, i.e. the target DNA segment, and the subsequent ability to detect the binding of the probe to the target. The particular DNA segment or target DNA segment of the present invention is present within soybean that contains the insertion event MON87751.

By reference to soybean it is intended that soybean cells, soybean seed, soybean plant parts and soybean plants are within the scope of the present invention so long as each embodiment contains a detectable amount of DNA corresponding to any one, two, or more of the segments that are described herein as being diagnostic for the presence of the soybean event MON87751 DNA. Soybean plant parts include cells; pollen; ovules; flowers; pods; seed; root tissue; stem tissue; and leaf tissue. Commodity products that are made from soybean in which a detectable amount of the segments of DNA described herein as being diagnostic for the presence of the event MON87751 are within the scope of the invention. Such commodity products may include whole or processed soybean seed, soybean oil, soybean protein, soybean meal, soybean flour, soybean flakes, soybean bran, soybean milk, soybean cheese, soybean wine, animal feed comprising soybean, paper comprising soybean, cream comprising soybean, soybean biomass, and fuel products produced using soybean plants and soybean plant parts.

The DNA of soybean event MON87751 may be present in each cell and in each genome on one chromosome of the soybean plant, soybean seed, and soybean tissues containing the event. As the soybean genome is transmitted to progeny in Mendelian fashion, if a soybean plant were homozygous for the event MON87751 insertion, each progeny soybean plant and cell would contain the event DNA on each allele of the parental chromosome containing the event MON87751 insertion and inherited by the progeny from the parent(s). However, if the soybean genome containing the event MON87751 DNA is a heterozygous or hybrid parent, then about fifty percent of the pollen and about fifty percent of the ovules engaged in mating from hybrid parents will contain the soybean event MON87751 DNA, resulting in a mixed population of progeny that contain the event MON87751 DNA, and the percentage of such progeny arising from such crosses with hybrids can range anywhere from about fifty to about seventy five percent having the event MON87751 DNA transmitted to such progeny.

The DNA molecules of the present invention may be unique to the two separate junctions on either end of the inserted transgenic event MON87751 DNA and the soybean genome DNA that is adjacent to, i.e. flanking, each end of the MON87751 inserted DNA, or unique to the soybean event MON87751 inserted DNA. These molecules, when present in a particular sample analyzed by the methods described herein using the probes, primers and in some cases using DNA sequence analysis, may be diagnostic for the presence of an amount of event MON87751 soybean in that sample. Such DNA molecules unique to the soybean event MON87751 DNA can be identified and characterized in a number of ways, including by use of probe nucleic acid molecules designed to bind specifically to the unique DNA molecules followed by detection of the binding of such probes to the unique DNA, and by thermal amplification methods that use at least two different DNA molecules that act as probes but the sequence of such molecules may be somewhat less specific than the probes described above. The skilled artisan understands that contacting a particular target DNA with a probe or primer under appropriate hybridization conditions will result in the binding of the probe or primer to the targeted DNA segment.

The DNA molecules of the present invention may be target segments of DNA that may be capable of amplification and, when detected as one or more amplicons of the represented length obtained by amplification methods of a particular sample, may be diagnostic for the presence of event MON87751, or the construct comprised therein, in such sample. Such DNA molecules or polynucleotide segments may have the nucleotide sequences as set forth in each of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, and SEQ ID NO:26, and are further defined herein and in the examples below. Primer molecules and/or probes may be provided in kit form along with the necessary reagents, including controls, and packaged together with instructions for use.

Recombinant DNA molecules of the present invention may be present within or derived from a microorganism. A microorganism is intended to include any microscopic cell, whether prokaryote or eukaryote or otherwise that contains DNA within a genome or chromosome or an extra-chromosomal DNA structure more commonly referred to as a plasmid or vector. In one embodiment, microscopic organisms may include bacteria (prokaryotes) and cells corresponding to higher life forms (eukaryotes) which are beneath the visual range of the average human, typically beneath fifty cubic microns and more generally beneath ten cubic microns. Bacteria are common microscopic microorganisms that may contain a vector or plasmid that contains one or more of the novel DNA segments of the present invention, including each of the respective expression cassettes present as set forth in SEQ ID NO:9. Plant cells and particularly soybean plant cells of the present invention may contain any one, two, or more or all of the novel DNA segments of the present invention.

Probes for use herein may comprise DNA molecules or polynucleotide segments of sufficient length to function under stringent hybridization conditions as defined herein to bind with a particular target DNA segment, i.e., a unique segment of DNA present within and diagnostic for the presence of, event MON87751 DNA in a sample. Such a probe can be designed to bind only to a single junction or other novel sequence present only in the soybean event MON87751 DNA, or to two or more such single junction segments. The detection of the binding of such a probe to a DNA molecule in a particular sample suspected of containing soybean DNA is diagnostic for the presence of soybean event MON87751 in the sample.

Primers may comprise pairs of different oligonucleotides or polynucleotide segments for use in a thermal amplification reaction which amplifies a particular DNA target segment. Each primer in the pair is designed to bind to a rather specific segment of DNA within or near to a segment of DNA of interest for amplification. The primers bind in such way that these then act as localized regions of nucleic acid sequence polymerization resulting in the production of one or more amplicons (amplified target segments of DNA). In the present invention, use of primers designed to bind to unique segments of soybean event MON87751 DNA in a particular biological sample and that amplify particular amplicons containing one or more of the junction segments described herein, and the detection and/or characterization of such amplicons upon completion or termination of the polymerase reaction, is diagnostic for the presence of the soybean event MON87751 in the particular sample. The skilled artisan is well familiar with this amplification method and no recitation of the specifics of amplification is necessary here.

Soybean plants, soybean plant cells, soybean plant tissues and soybean seed of the present invention may be resistant to infestation by lepidopteran insect pests, including but not limited to *Chrysodeixis* spp., *Spodoptera* spp., *Helicoverpa* spp., *Crocidosema* spp., *Rachiplusia* spp., *Anticarsia* spp., *Elasmopalpus* spp., and *Plathypena* spp. The resistance to infestation by lepidopteran species arises in connection with the expression of two different DNA segments, encoding two different insecticidal proteins, that are operably and covalently linked within the inserted transgenic DNA: a Cry2Ab protein expressed from the expression cassette at the 5' proximal end of the inserted transgenic DNA as set forth in SEQ ID NO:10 and illustrated in FIG. 2; and a Cry1A.105 protein expressed from the expression cassette at the 3'end of the inserted transgenic DNA as set forth in SEQ ID NO:10 and illustrated in FIG. 2. The Cry2Ab protein is expressed from an At.Act2 promoter, while the Cry1A.105 protein is expressed from an At.RbcS4 promoter. The Cry2Ab and the Cry1A.105 proteins are agents toxic to lepidopteran insect pest species.

The construct used to generate soybean event MON87751 has the promoters driving expression of the Cry2Ab and the Cry1A.105 proteins positioned in a relative tandem orientation of transcription so that expression from each promoter of the respective Cry proteins proceeds in the same direction, but each from their separate respective promoters (see FIG. 2). Other constructs which were evaluated varied in the combination of the use of expression elements, i.e., enhancer (E), promoter (P), leader (L), introns (I), chloroplast targeting peptide (CTP), and 3'UTR (T). Also, the constructs contained either a vector stack of both Cry proteins (Cry2Ab and Cry1A.105), or contained a single Cry protein, i.e., Cry2Ab or Cry1A.105. A further variation in the expression constructs was the relative orientation of the two cassettes for the Cry proteins in the vector stack constructs. Specifically, the two cassettes were either in a tandem orientation of transcription, or the two cassettes were in a divergent orientation so that expression from each promoter of the two Cry proteins is away from a point centered between the two promoters, i.e., transcription of each expression cassette proceeds in opposite directions and does not converge. The DNA sequence encoding Cry1A.105 was sequence diversified in some constructs relative to the sequence in the transgene inserted into event MON87751. Finally, in two of the constructs with the two Cry expression cassettes oriented in reverse orientation of transcription, transcription enhancers were positioned between the diverging promoters (see FIG. 2).

The event MON87751 was selected based on comparisons to thousands of different independent transgenic events each transformed with one of the constructs containing a T-DNA segment as illustrated in FIG. 2, and to either event MON87701 and/or to event GM_A19478 (generated at the same time as MON87701, and both expressing Cry1Ac); to a transgenic event 40-3-2 (conferring tolerance to the herbicide glyphosate); and to non-transgenic control soybean (A3555, or A5547). The results as illustrated below in the examples show that the event MON87751 exhibited superior properties due to expression of the Cry2Ab and Cry1A.105 proteins. The plurality of transgenic events produced using the construct used for generating the event MON87751 were each more likely than other events produced with other constructs to exhibit efficacious control of lepidopteran insect pests.

Soybean plants and parts thereof including seed, each containing the DNA corresponding to event MON87751, are within the scope of the present invention. Such plants and parts thereof including seed are resistant to lepidopteran infestation. In certain embodiments, such plants and seed include hybrids and inbreds, and plants and seed that contain only one event MON87751 allele, i.e., a genome characterized as heterozygous with reference to the locus corresponding to the event MON87751 DNA. Such hybrids may be produced by breeding plants comprising event MON87751 with desirable germplasm as part of the commercial variety development process and other agriculturally desirable properties of soybean. Hybrids may be produced by any number of methods but a preferred method takes advantage of a first inbred (homozygous) parent that contains the event MON87751 specific allele on both chromosomes at the locus at which the event MON87751 DNA is inserted, and breeding the first inbred together with a second inbred which does not contain the MON87751 DNA. Both parental inbred varieties will have one or more advantageous properties desirable in the progeny seed, i.e. the hybrid seed, and these hybrid seed are heterozygous for the event MON87751 allele.

A transgenic property or allele conferring some additional trait to a plant containing the event MON87751 DNA may be desirable. Other such transgenic alleles conferring desirable traits may include herbicide tolerance: GTS 40-3-2, MON87708, MON89788, A2704-12, A2704-21, A5547-35, A5547-127, BPS-CV127-9, DP356043, GU262, W62, W98, DAS-44406-6, DAS-68416-4, FG72, BPS-CV127-9, SYHT04R, SYHT0H2, 3560.4.3.5, EE-GM3, pDAB4472-1606, pDAB4468-0416, pDAB8291.45.36, 127, AAD-12; insect resistance: MON87701, DAS-81419-2; increased enhanced oil composition: DP-305423, G94-1, G94-19, G168, OT96-15, MON87705, MON87769; increased yield: MON 87712, or nitrogen fixation traits, traits modulating the use of water, resistance to fungal infestation, resistance to nematode infestation, and the like. A non-transgenic property (e.g., QTL or maturity group) may also confer a desirable trait and one with skill in the art would know how to breed soybean to contain such non-transgenic trait and event MON87751 DNA.

The foregoing and other aspects of the invention will become more apparent from the following detailed description.

Figure 5:
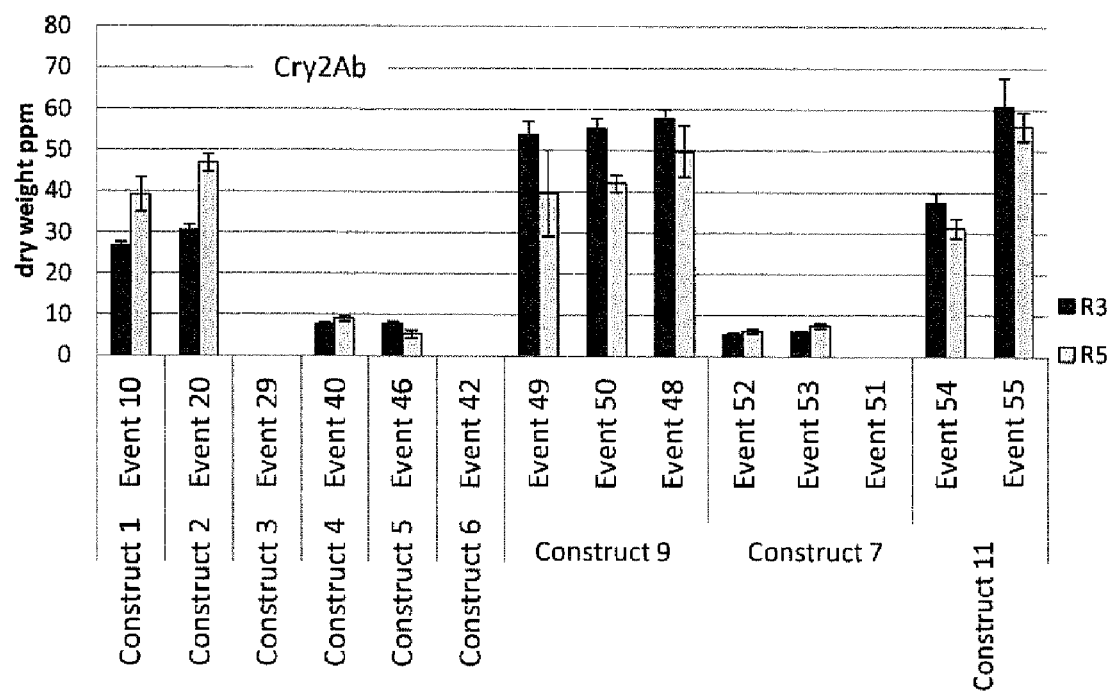

FIG. 5 is a graphical representation of the results of ELISA analysis of Cry2Ab protein expression in events generated with construct 1, construct 2, construct 3, construct, 4, construct 5, construct 6, construct 9, construct 7, and construct 11 for leaf samples collected at the R3 and R5 stage of plant growth.

Figure 6:
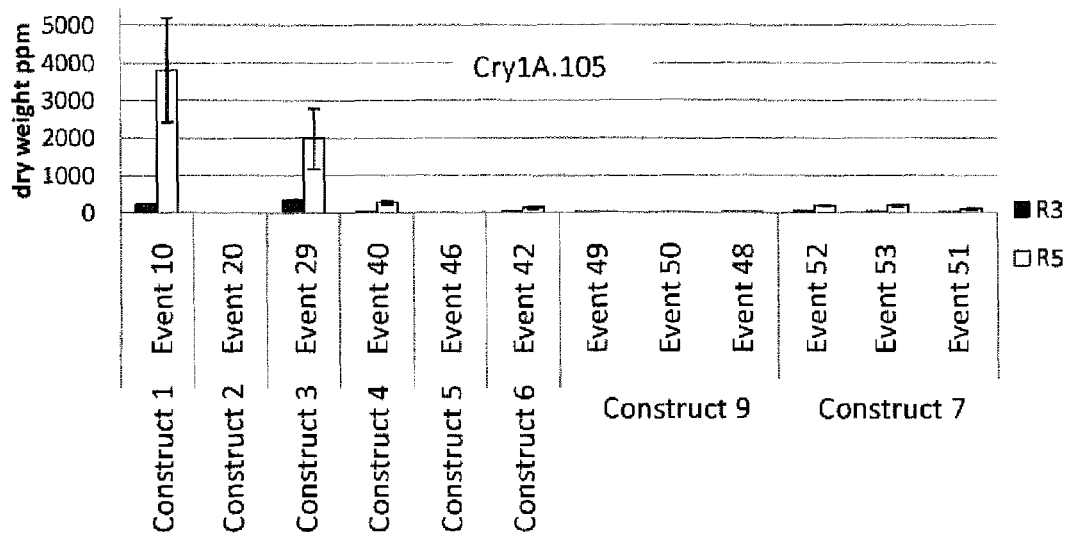
Figure 6:
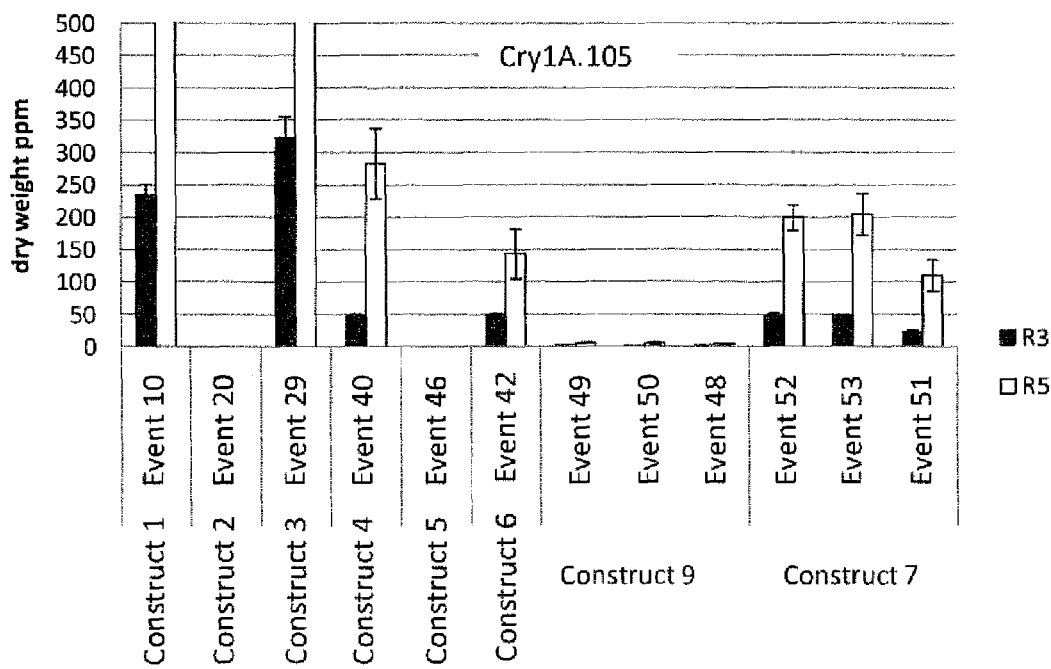

FIG. 6 is a graphical representation of the results of ELISA analysis of Cry21A.105 protein expression in events generated with construct 1, construct 2, construct 3, construct, 4, construct 5, construct 6, construct 9, construct 7, and construct 11 for leaf samples collected at the R3 and R5 stage of plant growth. Panel A Y-axis plotted at 0-5000 ppm dry weight and Panel B Y-axis plotted at 0-500 ppm dry weight to better illustrate in Panel B the data for the R3 stage.

BRIEF DESCRIPTION OF THE SEQUENCES

SEQ ID NO:1 is a twenty nucleotide sequence representing the 5' junction region of soybean genomic DNA and the integrated transgenic expression cassette. SEQ ID NO:1 is positioned in SEQ ID NO:10 at nucleotide position 1325-1344.

SEQ ID NO:2 is a twenty nucleotide sequence representing the 3' junction region of soybean genomic DNA and the integrated transgenic expression cassette. SEQ ID NO:2 is positioned in SEQ ID NO:10 at nucleotide position 11444-11463.

SEQ ID NO:3 is a sixty nucleotide sequence representing the 5' junction region of soybean genomic DNA and the integrated transgenic expression cassette. SEQ ID NO:3 is positioned in SEQ ID NO:10 at nucleotide position 1305-1364.

SEQ ID NO:4 is a sixty nucleotide sequence representing the 3' junction region of soybean genomic DNA and the integrated transgenic expression cassette. SEQ ID NO:4 is positioned in SEQ ID NO:10 at nucleotide position 11424-11483.

SEQ ID NO:5 is a one-hundred nucleotide sequence representing the 5' junction region of soybean genomic DNA and the integrated transgenic expression cassette. SEQ ID NO:5 is positioned in SEQ ID NO:10 at nucleotide position 1285-1384.

SEQ ID NO:6 is a one-hundred nucleotide sequence representing the 3' junction region of soybean genomic DNA and the integrated transgenic expression cassette. SEQ ID NO:6 is positioned in SEQ ID NO:10 at nucleotide position 11404-11503.

SEQ ID NO:7 is a 1626 nucleotide sequence representing the 5' flanking soybean genomic sequence up to and including the junction of the genomic DNA and transgenic inserted DNA, and includes (5' to 3') 1334 of flanking genomic DNA and 292 nucleotides of the arbitrarily designated 5' end of the inserted transgenic DNA.

SEQ ID NO:8 is a 1452 nucleotide sequence representing the flanking soybean genomic sequence up to and including the junction of the genomic DNA and transgenic inserted DNA, and includes (5' to 3') 265 nucleotides of the arbitrarily designated 3' end of the inserted transgenic DNA and 1187 nucleotides of 3' flanking genomic DNA.

SEQ ID NO:9 is a 10119 nucleotide sequence corresponding to the transgenic DNA inserted in the genome of soybean event MON87751.

SEQ ID NO:10 is a 12640 nucleotide sequence corresponding the composite nucleotide sequence of the transgenic genomic DNA inserted in event MON87751 and the 5' flanking genomic DNA nucleotide sequences and the 3' flanking genomic DNA nucleotide sequence and includes SEQ ID NO:7 and SEQ ID NO:9 and SEQ ID NO:8.

SEQ ID NO:11 is a 27 nucleotide sequence corresponding to a thermal amplification primer referred to as SQ20267 used to identify soybean event MON87751 DNA in a sample, and is identical to the nucleotide sequence corresponding to positions 11400 to 11426 of SEQ ID NO:10.

SEQ ID NO:12 is a 26 nucleotide sequence corresponding to a thermal amplification primer referred to as SQ25826 used to identify soybean event MON87751 DNA in a sample, and is identical to the reverse compliment of the nucleotide sequence corresponding to positions 11454 to 11479 of SEQ ID NO:10.

SEQ ID NO:13 is a 19 nucleotide sequence corresponding to a probe referred to as PB 10263 used to identify soybean event MON87751 DNA in a sample, and is identical to the nucleotide sequence corresponding to positions 11428 to 11446 of SEQ ID NO:10.

SEQ ID NO:14 is a 24 nucleotide sequence corresponding to a thermal amplification primer referred to as SQ27115 used to identify the presence of soybean wild-type allele DNA and/or soybean event MON87751 DNA in a sample, and is identical to the reverse compliment of the nucleotide sequence corresponding to positions 11458 to 11481 of SEQ ID NO:10.

SEQ ID NO:15 is a 30 nucleotide sequence corresponding to a thermal amplification primer referred to as SQ26901 used in a zygosity assay to identify the presence of wild-type allele DNA in a sample derived from soybean, and is identical to the nucleotide sequence corresponding to positions 1288 to 1317 of SEQ ID NO:10.

SEQ ID NO:16 is a 18 nucleotide sequence corresponding to a probe referred to as PB 11254 and is used in a zygosity assay to identify the presence of a wild-type allele DNA in a sample derived from soybean.

SEQ ID NO:17 is a 112 nucleotide sequence corresponding to a unique nucleotide sequence in the transgenic DNA (SEQ ID NO:9) inserted in soybean event MON87751, and is identical to positions 36-147 in SEQ ID NO:9, and to positions 1370-1481 in SEQ ID NO:10.

SEQ ID NO:18 is a 52 nucleotide sequence corresponding to a unique nucleotide sequence in the transgenic DNA (SEQ ID NO:9) inserted in soybean event MON87751, and is identical to positions 1305-1356 in SEQ ID NO:9, and to positions 1639-1690 in SEQ ID NO:10.

SEQ ID NO:19 is a 283 nucleotide sequence corresponding to a unique nucleotide sequence in the transgenic DNA (SEQ ID NO:9) inserted in soybean event MON87751, and is identical to positions 1561-1843 in SEQ ID NO:9, and to positions 2895-3177 in SEQ ID NO:10.

SEQ ID NO:20 is a 486 nucleotide sequence corresponding to a unique nucleotide sequence in the transgenic DNA (SEQ ID NO:9) inserted in soybean event MON87751, and is identical to positions 2340-2825 in SEQ ID NO:9, and to positions 3674-4159 in SEQ ID NO:10.

SEQ ID NO:21 is a 179 nucleotide sequence corresponding to a unique nucleotide sequence in the transgenic DNA (SEQ ID NO:9) inserted in soybean event MON87751, and is identical to positions 3326-3504 in SEQ ID NO:9, and to positions 4660-4838 in SEQ ID NO:10.

SEQ ID NO:22 is a 106 nucleotide sequence corresponding to a unique nucleotide sequence in the transgenic DNA (SEQ ID NO:9) inserted in soybean event MON87751, and is useful for identifying event MON87751 DNA in a sample, and is identical to positions 3749-3854 in SEQ ID NO:9, and to positions 5083-5188 in SEQ ID NO:10.

SEQ ID NO:23 is a 60 nucleotide sequence corresponding to a unique nucleotide sequence in the transgenic DNA (SEQ ID NO:9) inserted in soybean event MON87751, and is useful for identifying event MON87751 DNA in a sample, and is identical to positions 9320-9379 in SEQ ID NO:9, and to positions 10654-10713 in SEQ ID NO:10.

SEQ ID NO:24 is a 66 nucleotide sequence corresponding to a unique nucleotide sequence in the transgenic DNA (SEQ ID NO:9) inserted in soybean event MON87751, and is useful for identifying event MON87751 DNA in a sample, and is identical to positions 9620-9685 in SEQ ID NO:9, and to positions 10954-11019 in SEQ ID NO:10.

SEQ ID NO:25 is a 156 nucleotide sequence corresponding to a unique nucleotide sequence in the transgenic DNA (SEQ ID NO:9) inserted in soybean event MON87751, and is useful for identifying event MON87751 DNA in a sample, and is identical to positions 9720-9875 in SEQ ID NO:9, and to positions 11054-11209 in SEQ ID NO:10.

SEQ ID NO:26 is a 1905 nucleotide sequence corresponding to the open reading frame encoding the Cry2Ab protein expressed in soybean event MON87751.

DETAILED DESCRIPTION

The inventors have identified a transgenic soybean event MON87751 that exhibits commercially acceptable resistance to agriculturally important insect pests in the order Lepidoptera such as *Spodoptera frugiperda* (fall armyworm, FAW), *Spodoptera eridania* (southern armyworm, SAW), *Spodoptera exigua* (beet armyworm, BAW), *Spodoptera ornithogalli* (yellowstriped armyworm, YSAW), *Crocidosema aporema* (bean shoot moth, BSM), *Rachiplusia nu* (sunflower looper, SFL), *Anticarsia gemmatalis* (velvetbean caterpillar, VBC), *Chrysodeixis includens* (soybean looper, SBL), *Helicoverpa zea* (soybean podworm, SPW), *Helicoverpa gelotopeon* (South American bollworm), *Elasmopalpus lignosellus*, (lesser cornstalk borer), *Estigmene acrea* (saltmarsh caterpillar), and *Plathypena scabra* (green cloverworm), amongst others. The event provides two different operably linked expression cassettes, one encoding Cry2Ab, and the other encoding Cry1A.105 insecticidal proteins, and provides two different modes of action for resistance to soybean from lepidopteran infestations. Other transgenic soybean events are known in the art, i.e. MON 88701, which expresses a Cry1Ac *Bacillus thuringiensis* (Bt) toxin protein (MacRae et al. 2005, Fischhoff & Perlak 1995). MON 88701 provides a single mode of action for resistance to major lepidopteran insect pests of soybean, though efficacy against *Spodoptera* spp. is not significant. It would be preferable to provide transgenic soybean expressing two or more different insecticidal proteins exhibiting efficacy to major pests of soybean and including control of *Spodoptera* spp. The inventors provide at least one solution to this problem in the form of the soybean event MON87751, which combines two covalently linked expression cassettes in one locus within the soybean genome, these cassettes conferring the traits of expanded lepidopteran species resistance, and additionally, provides to the soybean cells, soybean tissues, soybean leaves, soybean pods, soybean seed, and soybean plants more than one mode of action to prevent or delay development of resistance among species of Lepidoptera.

The soybean event MON87751 was produced by an *Agrobacterium* mediated transformation process of soybean meristem tissue with the plasmid construct 1. This plasmid construct contains two regions, each bounded by *Agrobacterium* border segments (T-DNA segment). The first T-DNA segment contains two linked plant expression cassettes, one expression cassette encoding a selectable marker and one expression cassette encoding a scorable marker. The second T-DNA segment contains two linked plant expression cassettes with the regulatory genetic elements necessary for expression in soybean plant cells of two different insecticidal proteins, Cry2Ab and Cry1A.105. Due to the two T-DNA segments in the plasmid construct 1, the T-DNA segment containing the selection/scorable marker genes inserted randomly into the soybean genome and at a site separate from the site of integration of the T-DNA segment containing the Cry2Ab and Cry1A.105 expression cassettes, thus allowing for segregation of the two T-DNA segments within the genome of the transformed soybean plants during the process of selfing and/or backcrossing, e.g. screening R1 and higher generation of transgenic plants. The transformed soybean cells were regenerated into intact soybean plants and individual plants were selected from the population of plants that showed integrity of the second T-DNA segment encoding the Cry2Ab and Cry1A.105 proteins. In R1 and subsequent generations, events were selected based on integrity of the second T-DNA segment encoding the Cry2Ab and Cry1A.105 proteins, and on the absence (i.e., segregation) of the first T-DNA segment encoding the selectable/scorable marker cassettes, and for plants not containing any plasmid backbone sequence. The expression of the Cry2Ab and Cry1A.105 insecticidal toxic proteins in the cells of the soybean event MON87751 confers resistance to lepidopteran insect pests when the soybean cells of event MON87751 are provided in the diet the insects.

The plasmid DNA inserted into the genome of soybean event MON87751 was characterized by detailed molecular analyses. These analyses included: the insert number (number of integration sites within the soybean genome), the genomic insert location (the specific site in the soybean genome where the insertion occurred), the copy number (the number of copies of the T-DNA within one locus), and the integrity of the transgenic inserted DNA. The plasmid construct containing the two linked expression cassettes inserted into the soybean genome giving rise to the event MON87751 contains multiple segments (junction sequences between elements used to build or construct the several expression cassettes) that are not known to appear naturally in the soybean genome nor in other vectors or transgenic events of soybean or otherwise (for example, sequences as set forth in SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, and SEQ ID NO:26). In addition, the transformation event that gave rise to the inserted transgenic DNA in the event MON87751 is characterized herein as an insertion into a single locus in the soybean genome, resulting in two new loci or junction sequences between the inserted DNA and the soybean genome DNA. Also characterized herein are additional unique sequences within the heterologous DNA inserted into the soybean genome of event MON87751 and that are of sufficient length to be unique only to a soybean genome comprising of the event MON87751 DNA. These junction sequences are useful for detecting the presence of the event MON87751 DNA in soybean cells, soybean tissue, soybean seed and soybean plants or soybean plant products (soybean commodity products). DNA molecular probes and primer pairs are described herein that have been developed for use in identifying the presence of these various junction segments in biological samples containing or suspected of containing soybean cells, soybean seed, soybean plant parts or soybean plant tissue that contain the event MON87751 DNA. The data show that event MON87751 contains a single T-DNA insertion with one copy of the inserted transgenic DNA. No additional elements from the transformation construct 1 other than portions of the *Agrobacterium tumefaciens* left and right border regions used for transgenic DNA transfer from the plant transformation plasmid to the soybean genome have been identified in event MON87751 DNA. Finally, thermal amplification producing specific amplicons diagnostic for the presence of such event MON87751 DNA in a sample, and DNA sequence analyses were performed to determine the arbitrarily assigned 5' and 3' insert-to-plant genome junctions, confirm the organization of the elements within the insert, and determine the complete DNA sequence of the inserted transgene DNA (SEQ ID NO:9) in soybean event MON87751.

Dozens of transgenic events were produced using the transformation construct 1 used to produce the transgenic soybean event MON87751, and ten additional transformation constructs were generated and used to produce many dozens of other transgenic soybean events which were compared to the soybean event MON87751 and similar soybean events. These events were tested by ELISA assay for expression in leaf tissue of the two insecticidal proteins, Cry2Ab and Cry1A.105. A subset of the events produced from each transformation, and most of the constructs, were tested for efficacy for controlling lepidopteran insect pests in small-plot screenhouse trials. It was determined that the plant expression elements, and relative orientation of the Cry2Ab and Cry1A.105 expression cassettes in the transformation construct 1, provided the events with the best efficacy against the broadest spectrum of lepidopteran insect pests tested.

Unless otherwise noted herein, terms are to be understood according to conventional usage by those of ordinary skill in the relevant art. Definitions of common terms in molecular biology may also be found in Rieger et al., *Glossary of Genetics: Classical and Molecular*, 5th edition, Springer-Verlag: New York, 1991; and Lewin, Genes V, Oxford University Press: New York, 1994. As used herein, the term "soybean" means *Glycine max* and includes all plant varieties that can be bred with soybean plants containing event MON87751 DNA, including wild soybean species as well as those plants belonging to the genus *Glycine* that permit breeding between species. As used herein, the term "comprising" means "including but not limited to".

The present invention provides for transgenic plants which have been transformed with a DNA construct that contains at least two expression cassettes; a first expression cassette expressing toxic amounts of insecticidal protein Cry2Ab, and a second expression cassette expressing toxic amounts of insecticidal protein Cry1A.105. What is meant by toxic amount is an efficacious amount, an insecticidal amount, an efficacious insecticidal amount, an insecticidally effective amount, a target insect suppressive amount, an efficacious pesticidal amount, an amount in the diet of insects of the order Lepidoptera that is insecticidal, and other similar terms to be understood according to conventional usage by those of ordinary skill in the relevant art. Soybean plants transformed according to the methods and with the DNA construct disclosed herein are resistant to lepidopteran insect pests. The linked agronomic traits provide ease in maintaining these traits together in a breeding population, and exhibit resistance to a broader spectrum of lepidopteran insect pests than plants containing only a single gene conferring resistance to lepidopteran insect pests (i.e., Cry1Ac).

A transgenic "plant" is produced by transformation of a plant cell with heterologous DNA, i.e., a polynucleic acid construct that includes a number of efficacious features of interest; regeneration of a plant resulting from the insertion of the transgene into the genome of the plant cell, and selection of a particular plant characterized by insertion into a particular genome location and the number of efficacious features of the regenerated transgenic plant. The term "event" refers to DNA from the original transformant comprising the inserted DNA, and flanking genomic sequence immediately adjacent to the inserted DNA. Such DNA is unique and would be expected to be transferred to a progeny that receives the inserted DNA including the transgene of interest as the result of a sexual cross of one parental line that includes the inserted DNA (e.g., the original transformant and progeny resulting from selfing) and a parental line that does not contain the inserted DNA. The present invention also provides the original transformant plant and progeny of the transformant that include the heterologous DNA. Such progeny may be produced by a sexual outcross between plants comprising the event and another plant wherein the progeny includes the heterologous DNA. Even after repeated backcrossing to a recurrent parent, the event is present in the progeny of the cross at the same chromosomal location. The present invention is related to the transgenic event, soybean plant comprising MON87751, progeny thereof, and DNA compositions contained therein.

A "probe" is an isolated nucleic acid to which may be attached a conventional detectable label or reporter molecule, e.g., a radioactive isotope, ligand, chemiluminescent agent, or enzyme. Such a probe is complementary to a strand of a target nucleic acid, in the case of the present invention, to a strand of DNA from MON87751 whether from a MON87751 containing plant or from a sample that includes MON87751 DNA. Probes according to the present invention include not only deoxyribonucleic or ribonucleic acids, but also polyamides and other probe materials that bind specifically to a target DNA sequence and can be used to detect the presence of that target DNA sequence.

DNA primers are isolated polynucleic acids that are annealed to a complementary target DNA strand by nucleic acid hybridization to form a hybrid between the primer and the target DNA strand, then extended along the target DNA strand by a polymerase, e.g., a DNA polymerase. A DNA primer pair or a DNA primer set of the present invention refer to two DNA primers useful for amplification of a target nucleic acid sequence, e.g., by the polymerase chain reaction (PCR) or other conventional polynucleic acid amplification methods.

DNA probes and DNA primers may be 11 polynucleotides or more in length, or may be 18 polynucleotides or more, 24 polynucleotides or more, or 30 polynucleotides or more. Such probes and primers are selected to be of sufficient length to hybridize specifically to a target sequence under high stringency hybridization conditions. Preferably, probes and primers according to the present invention have complete sequence similarity with the target sequence, although probes differing from the target sequence that retain the ability to hybridize to target sequences may be designed by conventional methods.

Primers and probes based on the flanking genomic DNA and insert sequences disclosed herein can be used to confirm (and, if necessary, to correct) the disclosed DNA sequences by conventional methods, e.g., by re-cloning and sequencing such DNA molecules.

The nucleic acid probes and primers of the present invention hybridize under stringent conditions to a target DNA molecule. Any conventional nucleic acid hybridization or amplification method can be used to identify the presence of DNA from a transgenic plant in a sample. Polynucleic acid molecules also referred to as nucleic acid segments or fragments thereof are capable of specifically hybridizing to other nucleic acid molecules under certain circumstances. As used herein, two polynucleic acid molecules are said to be capable of specifically hybridizing to one another if the two molecules are capable of forming an anti-parallel, double-stranded nucleic acid structure. A nucleic acid molecule is said to be the "complement" of another nucleic acid molecule if they exhibit complete complementarity. As used herein, molecules are said to exhibit "complete complementarity" when every nucleotide of one of the molecules is complementary to a nucleotide of the other. Two molecules are said to be "minimally complementary" if they can hybridize to one another with sufficient stability to permit them to remain annealed to one another under at least conventional "low-stringency" conditions. Similarly, the molecules are said to be "complementary" if they can hybridize to one another with sufficient stability to permit them to remain annealed to one another under conventional "high-stringency" conditions. Conventional stringency conditions are described by Sambrook et al., 1989, and by Haymes et al., In: *Nucleic Acid Hybridization, A Practical Approach*, IRL Press, Washington, D.C. (1985). Departures from complete complementarity are therefore permissible, as long as such departures do not completely preclude the capacity of the molecules to form a double-stranded structure. In order for a nucleic acid molecule to serve as a primer or probe it need only be sufficiently complementary in sequence to be able to form a stable double-stranded structure under the particular solvent and salt concentrations employed.

As used herein, a substantially homologous sequence is a nucleic acid sequence that will specifically hybridize to the complement of the nucleic acid sequence to which it is being compared under high stringency conditions. Appropriate stringency conditions that promote DNA hybridization, for example, 6.0× sodium chloride/sodium citrate (SSC) at about 45° C., followed by a wash of 2.0×SSC at 50° C., are known to those skilled in the art or can be found in *Current Protocols in Molecular Biology*, John Wiley & Sons, N.Y. (1989), 6.3.1-6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed. In a preferred embodiment, a polynucleic acid of the present invention will specifically hybridize to one or more of the nucleic acid molecules set forth in SEQ ID NOs: 1, 2, 3, 4, 5, 6, 7, 8, 9, 10, 17, 18, 19, 20, 21, 22, 23, or 24, or complements thereof or fragments of either under moderately stringent conditions, for example at about 2.0×SSC and about 65° C. In a particularly preferred embodiment, a nucleic acid of the present invention will specifically hybridize to one or more of the nucleic acid molecules set forth in SEQ ID NOs: 1, 2, 3, 4, 5, 6, 7, 8, 9, 10, 17, 18, 19, 20, 21, 22, 23, or 24 or complements or fragments of either under high stringency conditions. In one aspect of the present invention, a preferred marker nucleic acid molecule of the present invention has the nucleic acid sequence set forth in SEQ ID NO:1, or SEQ ID NO:2, or SEQ ID NO:3, or SEQ ID NO:4, or SEQ ID NO:5, or SEQ ID NO:6, or SEQ ID NO:7, or SEQ ID NO:8, or SEQ ID NO:9, or SEQ ID NO:10; or SEQ ID NO:17, or SEQ ID NO:18, OR SEQ ID NO:19, or SEQ ID NO:20, or SEQ ID NO:21, or SEQ ID NO:22, or SEQ ID NO: 23, or complements thereof or fragments of either. The hybridization of the probe to the target DNA molecule can be detected by any number of methods known to those skilled in the art, these can include, but are not limited to, fluorescent tags, radioactive tags, antibody based tags, and chemiluminescent tags.

Regarding the amplification of a target nucleic acid sequence (e.g., by PCR) using a particular amplification primer pair, "stringent conditions" are conditions that permit the primer pair to hybridize only to the target nucleic acid sequence to which a primer having the corresponding wild-type sequence (or its complement) would bind and preferably to produce a unique amplification product, the amplicon, in a DNA thermal amplification reaction.

The term "specific for (a target sequence)" indicates that a probe or primer hybridizes under stringent hybridization conditions only to the target sequence in a sample comprising the target sequence.

As used herein, "amplified DNA" or "amplicon" refers to the product of polynucleic acid amplification method directed to a target polynucleic acid molecule that is part of a polynucleic acid template. For example, to determine whether a soybean plant resulting from a sexual cross contains transgenic plant genomic DNA from a soybean plant comprising event MON87751 of the present invention, DNA that is extracted from a soybean plant tissue sample may be subjected to a polynucleic acid amplification method using a primer pair that includes a first primer derived from a genomic DNA sequence in the region flanking the heterologous inserted DNA of event MON87751 and is elongated by polymerase 5' to 3' in the direction of the inserted DNA. The second primer is derived from the heterologous inserted DNA molecule is elongated by the polymerase 5' to 3' in the direction of the flanking genomic DNA from which the first primer is derived. The amplicon may range in length from the combined length of the primer pair plus one nucleotide base pair, or plus about fifty nucleotide base pairs, or plus about two hundred-fifty nucleotide base pairs, or plus about four hundred-fifty nucleotide base pairs or more. Alternatively, a primer pair can be derived from genomic sequence on both sides of the inserted heterologous DNA so as to produce an amplicon that includes the entire insert polynucleotide sequence (e.g., a forward primer isolated from the genomic portion on the 5' end of SEQ ID NO:10 and a reverse primer isolated from the genomic portion on the 3' end of SEQ ID NO:10 that amplifies a DNA molecule comprising the inserted heterologous DNA sequence (SEQ ID NO:9) identified herein in the event MON87751 containing genome). A member of a primer pair derived from the plant genomic sequence adjacent to the inserted transgenic DNA is located a distance from the inserted DNA sequence, this distance can range from one nucleotide base pair up to about twenty thousand nucleotide base pairs. The use of the term "amplicon" specifically excludes primer dimers that may be formed in the DNA thermal amplification reaction.

For practical purposes, one should design primers which produce amplicons of a limited size range, for example, between 100 to 1000 bases. Smaller (shorter polynucleotide length) sized amplicons in general are more reliably produced in thermal amplification reactions, allow for shorter cycle times, and can be easily separated and visualized on agarose gels or adapted for use in endpoint TAQMAN®-like assays. Smaller amplicons can be produced and detected by methods known in the art of DNA amplicon detection. In addition, amplicons produced using the primer pairs can be cloned into vectors, propagated, isolated, and sequenced or can be sequenced directly with methods well established in the art. Any primer pair derived from the combination of SEQ ID NO:7 and SEQ ID NO:9 or the combination of SEQ ID NO:8 and SEQ ID NO:9 that are useful in a DNA amplification method to produce an amplicon diagnostic for plants comprising MON87751 or progeny thereof is an aspect of the invention. Any single isolated DNA polynucleotide primer molecule comprising at least 15 contiguous nucleotides of SEQ ID NO:7, or its complement that is useful in a DNA amplification method to produce an amplicon diagnostic for plants comprising MON87751 or progeny thereof is an aspect of the invention. Any single isolated DNA polynucleotide primer molecule comprising at least 15 contiguous nucleotides of SEQ ID NO:8, or its complement that is useful in a DNA amplification method to produce an amplicon diagnostic for plants comprising MON87751 or progeny thereof is an aspect of the invention. Any single isolated DNA polynucleotide primer molecule comprising at least 15 contiguous nucleotides of SEQ ID NO:9, or its complement that is useful in a DNA amplification method to produce an amplicon diagnostic for plants comprising MON87751 or progeny thereof is an aspect of the invention.

Polynucleic acid amplification can be accomplished by any of the various polynucleic acid amplification methods known in the art, including the polymerase chain reaction (PCR). Amplification methods are known in the art and are described, inter alia, in U.S. Pat. Nos. 4,683,195 and 4,683,202 and in *PCR Protocols: A Guide to Methods and Applications*, ed. Innis et al., Academic Press, San Diego, 1990. PCR amplification methods have been developed to amplify up to 22 kb (kilobase) of genomic DNA and up to 42 kb of bacteriophage DNA (Cheng et al., Proc. Natl. Acad. Sci. USA 91:5695-5699, 1994). These methods as well as other methods known in the art of DNA amplification may be used in the practice of the present invention. The sequence of the heterologous DNA insert or flanking genomic DNA sequence from soybean event MON87751 can be verified (and corrected if necessary) by amplifying such DNA molecules from soybean seed containing event MON87751 DNA or soybean plants grown from the soybean seed containing event MON87751 DNA deposited with the ATCC having accession no. PTA-120166, using primers derived from the sequences provided herein, followed by standard DNA sequencing of the PCR amplicon or cloned DNA fragments thereof.

The diagnostic amplicon produced by these methods may be detected by a plurality of techniques. One such method is Genetic Bit Analysis (Nikiforov, et al. *Nucleic Acid Res.* 22:4167-4175, 1994) where a DNA oligonucleotide is designed that overlaps both the adjacent flanking genomic DNA sequence and the inserted DNA sequence. The oligonucleotide is immobilized in wells of a microtiter plate. Following PCR of the region of interest (using one primer in the inserted sequence and one in the adjacent flanking genomic sequence), a single-stranded PCR product can be hybridized to the immobilized oligonucleotide and serve as a template for a single base extension reaction using a DNA polymerase and labeled dideoxynucleotide triphosphates (ddNTPs) specific for the expected next base. Readout may be fluorescent or ELISA-based. A signal indicates presence of the transgene/genomic sequence due to successful amplification, hybridization, and single base extension.

Another method is the Pyrosequencing technique as described by Winge (*Innov. Pharma. Tech.* 00:18-24, 2000). In this method an oligonucleotide is designed that overlaps the adjacent genomic DNA and insert DNA junction. The oligonucleotide is hybridized to single-stranded PCR product from the region of interest (one primer in the inserted sequence and one in the flanking genomic sequence) and incubated in the presence of a DNA polymerase, ATP, sulfurylase, luciferase, apyrase, adenosine 5' phosphosulfate and luciferin. DNTPs are added individually and the incorporation results in a light signal that is measured. A light signal indicates the presence of the transgene/genomic sequence due to successful amplification, hybridization, and single or multi-base extension.

Fluorescence Polarization as described by Chen, et al., (*Genome Res.* 9:492-498, 1999) is a method that can be used to detect the amplicon of the present invention. Using this method an oligonucleotide is designed that overlaps the genomic flanking and inserted DNA junction. The oligonucleotide is hybridized to single-stranded PCR product from the region of interest (one primer in the inserted DNA and one in the flanking genomic DNA sequence) and incubated in the presence of a DNA polymerase and a fluorescent-labeled ddNTP. Single base extension results in incorporation of the ddNTP. Incorporation can be measured as a change in polarization using a fluorometer. A change in polarization indicates the presence of the transgene/genomic sequence due to successful amplification, hybridization, and single base extension.

Taqman® (PE Applied Biosystems, Foster City, Calif.) is described as a method of detecting and quantifying the presence of a DNA sequence and is fully understood in the instructions provided by the manufacturer. Briefly, a FRET oligonucleotide probe is designed that overlaps the genomic flanking and insert DNA junction. The FRET probe and PCR primers (one primer in the insert DNA sequence and one in the flanking genomic sequence) are cycled in the presence of a thermalstable polymerase and dNTPs. Hybridization of the FRET probe results in cleavage and release of the fluorescent moiety away from the quenching moiety on the FRET probe. A fluorescent signal indicates the presence of the transgene/genomic sequence due to successful amplification and hybridization.

Molecular Beacons have been described for use in sequence detection as described in Tyangi, et al. (*Nature Biotech.* 14:303-308, 1996). Briefly, a FRET oligonucleotide probe is designed that overlaps the flanking genomic and insert DNA junction. The unique structure of the FRET probe results in it containing secondary structure that keeps the fluorescent and quenching moieties in close proximity. The FRET probe and PCR primers (one primer in the insert DNA sequence and one in the flanking genomic sequence) are cycled in the presence of a thermalstable polymerase and dNTPs. Following successful PCR amplification, hybridization of the FRET probe to the target sequence results in the removal of the probe secondary structure and spatial separation of the fluorescent and quenching moieties. A fluorescent signal results. A fluorescent signal indicates the presence of the flanking/transgene insert sequence due to successful amplification and hybridization.

DNA detection kits that are based on DNA amplification methods contain DNA primer molecules that hybridize specifically to a target DNA and amplify a diagnostic amplicon under the appropriate reaction conditions. The kit may provide an agarose gel based detection method or any number of methods of detecting the diagnostic amplicon that are known in the art. DNA detection kits can be developed using the compositions disclosed herein and are useful for identification of soybean event MON87751 DNA in a sample and can be applied to methods for breeding soybean plants containing event MON87751 DNA. A kit that contains DNA primers that are homologous or complementary to any portion of the soybean genomic region as set forth in SEQ ID NO:10 and to any portion of the inserted transgenic DNA as set forth in SEQ ID NO:10 is an object of the invention. The DNA molecules can be used in DNA amplification methods (PCR) or as probes in polynucleic acid hybridization methods, i.e., Southern analysis, northern analysis.

Junction sequences may be represented by a sequence from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10; SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, and SEQ ID NO:26. For example, the junction sequences may be arbitrarily represented by the nucleotide sequences provided as SEQ ID NO:1 and SEQ ID NO:2. Alternatively, the junction sequences may be arbitrarily represented by the nucleotide sequences provided as SEQ ID NO:3 and SEQ ID NO:4. Alternatively, the junction sequences may be arbitrarily represented by the nucleotide sequences provided as SEQ ID NO:5 and SEQ ID NO:6. These nucleotides are connected by phosphodiester linkage and in soybean event MON87751 are present as part of the recombinant plant cell genome. The identification of one or more of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10; SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, and SEQ ID NO:26 in a sample derived from a soybean plant, soybean seed, or soybean plant part is determinative that the DNA was obtained from soybean event MON87751 and is diagnostic for the presence in a sample containing DNA from soybean event MON87751. The invention thus provides a DNA molecule that contains at least one of the nucleotide sequences provided as SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10; SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, and SEQ ID NO:26. Any segment of DNA derived from transgenic soybean event MON87751 that is sufficient to include at least one of the sequences provided as SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10; SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, or SEQ ID NO:26 is within the scope of the invention. In addition, any polynucleotide comprising a sequence complementary to any of the sequences described within this paragraph is within the scope of the invention.

The invention provides exemplary DNA molecules that can be used either as primers or probes for detecting the presence of DNA derived from a soybean plant comprising event MON87751 DNA in a sample. Such primers or probes are specific for a target nucleic acid sequence and as such are useful for the identification of soybean event MON87751 nucleic acid sequence by the methods of the invention described herein.

A "primer" may be a highly purified, isolated polynucleotide that is designed for use in specific annealing or hybridization methods that involve thermal amplification. A pair of primers may be used with template DNA, such as a sample of soybean genomic DNA, in a thermal amplification, such as polymerase chain reaction (PCR), to produce an amplicon, where the amplicon produced from such reaction would have a DNA sequence corresponding to sequence of the template DNA located between the two sites where the primers hybridized to the template. As used herein, an "amplicon" is a replication of a piece or fragment of DNA that has been synthesized using amplification techniques. An amplicon of the invention may comprise at least one of the sequences provided as provided as SEQ ID NO:11 or SEQ ID NO:12. A primer is typically designed to hybridize to a complementary target DNA strand to form a hybrid between the primer and the target DNA strand, and the presence of the primer is a point of recognition by a polymerase to begin extension of the primer (i.e., polymerization of additional nucleotides into a lengthening nucleotide molecule) using as a template the target DNA strand. Primer pairs, as used in the invention, are intended to refer to use of two primers binding opposite strands of a double stranded nucleotide segment for the purpose of amplifying linearly the polynucleotide segment between the positions targeted for binding by the individual members of the primer pair, typically in a thermal amplification reaction or other conventional nucleic-acid amplification methods. Exemplary DNA molecules useful as primers are provided as SEQ ID NO:11, SEQ ID NO:12, SEQ ID NO:14, or SEQ ID NO:15. The primer pair provided as SEQ ID NO:11 and SEQ ID NO:12 are useful as a first DNA molecule and a second DNA molecule that is different from the first DNA molecule, and both are each of sufficient length of contiguous nucleotides of SEQ ID NO:10 to function as DNA primers that, when used together in a thermal amplification reaction with template DNA derived from soybean event MON87751, to produce an amplicon diagnostic for soybean event MON87751 DNA in a sample.

A "probe" is an isolated nucleic acid that is complementary to a strand of a target nucleic acid. Probes according to the invention include not only deoxyribonucleic or ribonucleic acids but also polyamides and other probe materials that bind specifically to a target DNA sequence and the detection of such binding can be useful in diagnosing, discriminating, determining, or confirming the presence of that target DNA sequence in a particular sample. A probe may be attached to a conventional detectable label or reporter molecule, e.g., a radioactive isotope, ligand, chemiluminescent agent, or enzyme. An exemplary DNA molecule useful as a probe is provided as SEQ ID NO:13 and SEQ ID NO:16.

Probes and primers according to the invention may have complete sequence identity with the target sequence, although primers and probes differing from the target sequence that retain the ability to hybridize preferentially to target sequences may be designed by conventional methods. In order for a nucleic acid molecule to serve as a primer or probe it need only be sufficiently complementary in sequence to be able to form a stable double-stranded structure under the particular solvent and salt concentrations employed. Any conventional nucleic acid hybridization or amplification method can be used to identify the presence of transgenic DNA from soybean event MON87751 in a sample. Probes and primers are generally at least about 11 nucleotides, at least about 18 nucleotides, at least about 24 nucleotides, or at least about 30 nucleotides or more in length. Such probes and primers hybridize specifically to a target DNA sequence under stringent hybridization conditions. Conventional stringency conditions are described by Sambrook et al., 1989, and by Haymes et al., In: *Nucleic Acid Hybridization, A Practical Approach*, IRL Press, Washington, D.C. (1985).

Any number of methods well known to those skilled in the art can be used to isolate and manipulate a DNA molecule, or fragment thereof, disclosed in the invention, including thermal amplification methods. DNA molecules, or fragments thereof, can also be obtained by other techniques such as by directly synthesizing the fragment by chemical means, as is commonly practiced by using an automated oligonucleotide synthesizer.

The DNA molecules and corresponding nucleotide sequences provided herein are therefore useful for, among other things, identifying soybean event MON87751, selecting plant varieties or hybrids comprising soybean event MON87751, detecting the presence of DNA derived from the transgenic soybean event MON87751 in a sample, and monitoring samples for the presence and/or absence of soybean event MON87751 or plant parts derived from soybean plants comprising event MON87751.

The invention provides soybean plants, soybean plant cells, soybean seeds, soybean plant parts (such as pollen, ovule, pod, flower tissue, root tissue, stem tissue, and leaf tissue), soybean progeny plants, soybean oil, soybean wine, soybean milk, soybean protein, and soybean commodity products. These soybean plants, soybean plant cells, soybean seeds, soybean plant parts, soybean progeny plants, soybean oil, soybean wine, soybean milk, soybean protein, and soybean commodity products contain a detectable amount of a polynucleotide of the invention, i.e., such as a polynucleotide having at least one of the sequences provided as SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10; SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, or SEQ ID NO:26. Soybean plants, plant cells, seeds, plant parts, and progeny plants of the invention may also contain one or more additional transgenes. Such additional transgene may be any nucleotide sequence encoding a protein or RNA molecule conferring a desirable trait including but not limited to increased insect resistance, increased water use efficiency, increased yield performance, increased drought resistance, increased seed quality, improved nutritional quality, and/or increased herbicide tolerance, in which the desirable trait is measured with respect to a soybean plant lacking such additional transgene.

The invention provides soybean plants, soybean plant cells, soybean seeds, soybean plant parts (such as pollen, ovule, pod, flower tissue, root tissue, stem tissue, and leaf tissue), soybean progeny plants derived from a transgenic soybean plant containing event MON87751 DNA. A representative sample of soybean seed containing event MON87751 DNA has been deposited according to the Budapest Treaty with the American Type Culture Collection (ATCC®). The ATCC repository has assigned the Patent Deposit Designation PTA-120166 to the seed containing event MON87751 DNA.

The invention provides a microorganism comprising a DNA molecule having at least one sequence selected from SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10; SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, and SEQ ID NO:26 present in its genome. An example of such a microorganism is a transgenic plant cell. Microorganisms, such as a plant cell of the invention, are useful in many industrial applications, including but not limited to: (i) use as research tool for scientific inquiry or industrial research; (ii) use in culture for producing endogenous or recombinant carbohydrate, lipid, nucleic acid, or protein products or small molecules that may be used for subsequent scientific research or as industrial products; and (iii) use with modern plant tissue culture techniques to produce transgenic plants or plant tissue cultures that may then be used for agricultural research or production. The production and use of microorganisms such as transgenic plant cells utilizes modern microbiological techniques and human intervention to produce a man-made, unique microorganism. In this process, recombinant DNA is inserted into a plant cell's genome to create a transgenic plant cell that is separate and unique from naturally occurring plant cells. This transgenic plant cell can then be cultured much like bacteria and yeast cells using modern microbiology techniques and may exist in an undifferentiated, unicellular state. The transgenic plant cell's new genetic composition and phenotype is a technical effect created by the integration of the heterologous DNA into the genome of the cell. Another aspect of the invention is a method of using a microorganism of the invention. Methods of using microorganisms of the invention, such as transgenic plant cells, include (i) methods of producing transgenic cells by integrating recombinant DNA into the genome of the cell and then using this cell to derive additional cells possessing the same heterologous DNA; (ii) methods of culturing cells that contain recombinant DNA using modern microbiology techniques; (iii) methods of producing and purifying endogenous or recombinant carbohydrate, lipid, nucleic acid, or protein products from cultured cells; and (iv) methods of using modern plant tissue culture techniques with transgenic plant cells to produce transgenic plants or transgenic plant tissue cultures.

Plants of the invention may pass along the event MON87751 DNA, including the transgene inserted in soybean event MON87751, to progeny. As used herein, "progeny" includes any plant, seed, plant cell, and/or regenerable plant part comprising the event MON87751 DNA derived from an ancestor plant and/or comprising a DNA molecule having at least one sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10; SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, and SEQ ID NO:26. Plants, progeny, and seeds may be homozygous or heterozygous for the transgene. Progeny may be grown from seeds produced by a soybean event MON87751 containing plant and/or from seeds produced by a plant fertilized with pollen from a soybean event MON87751 containing plant.

Progeny plants may be self-pollinated (also known as "selfing") to generate a true breeding line of plants, i.e., plants homozygous for the transgene. Selfing of appropriate progeny can produce plants that are homozygous for both added, exogenous genes.

Alternatively, progeny plants may be out-crossed, e.g., bred with another unrelated plant, to produce a varietal or a hybrid seed or plant. The other unrelated plant may be transgenic or non-transgenic. A varietal or hybrid seed or plant of the invention may thus be derived by sexually crossing a first parent that lacks the specific and unique DNA of the soybean event MON87751 with a second parent comprising soybean event MON87751, resulting in a hybrid comprising the specific and unique DNA of the soybean event MON87751. Each parent can be a hybrid or an inbred/varietal, so long as the cross or breeding results in a plant or seed of the invention, i.e., a seed having at least one allele containing the DNA of soybean event MON87751 and/or a DNA molecule having at least one sequence selected from SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10; SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, and SEQ ID NO:26. Two different transgenic plants may thus be crossed to produce hybrid offspring that contain two independently segregating, added, exogenous genes. For example, the MON87751 containing Cry2Ab and Cry1A.105 conferring dual mode of action insect resistance to soybean can be crossed with other transgenic soybean plants to produce a plant having the characteristics of both transgenic parents. One example of this would be a cross of MON87751 containing Cry2Ab and Cry1A.105 conferring dual mode of action insect resistance to soybean with a plant having one or more additional traits such as herbicide tolerance (e.g. soybean event MON89788 or soybean event MON 87708) and/or insect control (e.g. soybean event MON 88701), resulting in a progeny plant or seed that has dual mode of action resistance to lepidopteran insect pests and has at least one or more additional traits. Back-crossing to a parental plant and out-crossing with a non-transgenic plant are also contemplated, as is vegetative propagation. Descriptions of other breeding methods that are commonly used for different traits and crops can be found in one of several references, e.g., Fehr, in *Breeding Methods for Cultivar Development*, Wilcox J. ed., American Society of Agronomy, Madison Wis. (1987).

The invention provides a plant part that is derived from soybean plants comprising event MON87751. As used herein, a "plant part" refers to any part of a plant which is comprised of material derived from a soybean plant comprising event MON87751. Plant parts include but are not limited to pollen, ovule, pod, flower, root or stem tissue, fibers, and leaves. Plant parts may be viable, nonviable, regenerable, and/or nonregenerable.

The invention provides a commodity product that is derived from soybean plants comprising event MON87751 and that contains a detectable amount of a nucleic acid specific for event MON87751. As used herein, a "commodity product" refers to any composition or product which is comprised of material derived from a soybean plant, whole or processed soybean seed, one or more plant cells and/or plant parts containing the soybean event MON87751 DNA. Commodity products may be sold to consumers and may be viable or nonviable. Nonviable commodity products include but are not limited to nonviable seeds; whole or processed seeds, seed parts, and plant parts; soybean oil, soybean protein, soybean meal, soybean flour, soybean flakes, soybean bran, soybean milk, soybean cheese, soybean wine, animal feed comprising soybean, paper comprising soybean, cream comprising soybean, soybean biomass, and fuel products produced using soybean plants and soybean plant parts. Viable commodity products include but are not limited to seeds, plants, and plant cells. The soybean plants comprising event MON87751 can thus be used to manufacture any commodity product typically acquired from soybean. Any such commodity product that is derived from soybean plants comprising event MON87751 may contain at least a detectable amount of the specific and unique DNA corresponding to soybean event MON87751, and specifically may contain a detectable amount of a polynucleotide comprising a DNA molecule having at least one sequence selected from SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10; SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, and SEQ ID NO:26. Any standard method of detection for nucleotide molecules may be used, including methods of detection disclosed herein. A commodity product is within the scope of the invention if there is any detectable amount of a DNA molecule having at least one sequence selected from SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10; SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, and SEQ ID NO:26 in the commodity product.

The plants, progeny, seeds, plant cells, plant parts (such as pollen, ovule, pod, flower, root or stem tissue, and leaves), and commodity products of the invention are therefore useful for, among other things, growing plants for the purpose of producing seed and/or plant parts comprising soybean event MON87751 for agricultural purposes, producing progeny comprising soybean event MON87751 for plant breeding and research purposes, use with microbiological techniques for industrial and research applications, and sale to consumers.

Methods for producing an insect resistant soybean plant comprising the DNA sequences specific and unique to event MON87751 of the invention are provided. Transgenic plants used in these methods may be homozygous or heterozygous for the transgene. Progeny plants produced by these methods may be varietal or hybrid plants; may be grown from seeds produced by a soybean event MON87751 containing plant and/or from seeds produced by a plant fertilized with pollen from a soybean event MON87751 containing plant; and may be homozygous or heterozygous for the transgene. Progeny plants may be subsequently self-pollinated to generate a true breeding line of plants, i.e., plants homozygous for the transgene, or alternatively may be out-crossed, e.g., bred with another unrelated plant, to produce a varietal or a hybrid seed or plant.

Methods of detecting the presence of DNA derived from a soybean cell, soybean tissue, soybean seed, or soybean plant comprising soybean event MON87751 in a sample are provided. One method consists of (i) extracting a DNA sample from at least one soybean cell, soybean tissue, soybean seed, or soybean plant, (ii) contacting the DNA sample with at least one primer that is capable of producing DNA sequence specific to event MON87751 DNA under conditions appropriate for DNA sequencing, (iii) performing a DNA sequencing reaction, and then (iv) confirming that the nucleotide sequence comprises a nucleotide sequence specific for event MON87751, or the construct comprised therein, such as one selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10; SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, and SEQ ID NO:26. Another method consists of (i)

extracting a DNA sample from at least one soybean cell, soybean tissue, soybean seed, or soybean plant, (ii) contacting the DNA sample with a primer pair that is capable of producing an amplicon from event MON87751 DNA under conditions appropriate for DNA amplification, (iii) performing a DNA amplification reaction, and then (iv) detecting the amplicon molecule and/or confirming that the nucleotide sequence of the amplicon comprises a nucleotide sequence specific for event MON87751, such as one selected from the group consisting of SEQ ID NO: 1, SEQ ID NO:2, SEQ ID NO:3, SEQ ID NO:4, SEQ ID NO:5, and SEQ ID NO:6. The amplicon should be one that is specific for event MON87751, such as an amplicon that comprises SEQ ID NO: 1, or SEQ ID NO:2, or SEQ ID NO:3, or SEQ ID NO:4, or SEQ ID NO:5, or SEQ ID NO:6. The detection of a nucleotide sequence specific for event MON87751 in the amplicon is determinative and/or diagnostic for the presence of the soybean event MON87751 specific DNA in the sample. An example of a primer pair that is capable of producing an amplicon from event MON87751 DNA under conditions appropriate for DNA amplification is provided as SEQ ID NO:11, and SEQ ID NO:12. Other primer pairs may be readily designed by one of skill in the art and would produce an amplicon comprising SEQ ID NO: 1, or SEQ ID NO:2, or SEQ ID NO:3, or SEQ ID NO:4, or SEQ ID NO:5, or SEQ ID NO:6, wherein such a primer pair comprises at least one primer within the genomic region flanking the insert and a second primer within the insert. Another method of detecting the presence of DNA derived from a soybean cell, soybean tissue, soybean seed, or soybean plant comprising soybean event MON87751 in a sample consists of (i) extracting a DNA sample from at least one soybean cell, soybean tissue, soybean seed, or soybean plant, (ii) contacting the DNA sample with a DNA probe specific for event MON87751 DNA, (iii) allowing the probe and the DNA sample to hybridize under stringent hybridization conditions, and then (iv) detecting hybridization between the probe and the target DNA sample. An example of the sequence of a DNA probe that is specific for event MON87751 DNA is provided as SEQ ID NO:13 or SEQ ID NO:16. Other probes may be readily designed by one of skill in the art and would comprise at least one fragment of genomic DNA flanking the insert and at least one fragment of insert DNA, such as sequences provided in, but not limited to, SEQ ID NO: 1, SEQ ID NO:2, SEQ ID NO:3, SEQ ID NO:4, SEQ ID NO:5, SEQ ID NO:6, SEQ ID NO:7, SEQ ID NO:8, and SEQ ID NO:10. Detection of probe hybridization to the DNA sample is diagnostic for the presence of soybean event MON87751 specific DNA in the sample. Absence of hybridization is alternatively diagnostic of the absence of soybean event MON87751 specific DNA in the sample.

DNA detection kits are provided that are useful for the identification of soybean event MON87751 DNA in a sample and can also be applied to methods for breeding soybean plants containing the appropriate event DNA. Such kits contain DNA primers and/or probes comprising fragments of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10; SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, and SEQ ID NO:26. One example of such a kit comprises at least one DNA molecule of sufficient length of contiguous nucleotides of SEQ ID NO:10 to function as a DNA probe useful for detecting the presence and/or absence of DNA derived from transgenic soybean plants comprising event MON87751 in a sample. The DNA derived from transgenic soybean plants comprising event MON87751 would comprise a DNA molecule having at least one sequence selected from SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10; SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, and SEQ ID NO:26. A DNA molecule sufficient for use as a DNA probe is provided that is useful for determining, detecting, or diagnosing the presence and/or absence of soybean event MON87751 DNA in a sample is provided as SEQ ID NO:13. Other probes may be readily designed by one of skill in the art and should comprise at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, or at least 40 contiguous nucleotides of SEQ ID NO:10 and be sufficiently unique to soybean event MON87751 DNA in order to identify DNA derived from the event. Another type of kit comprises a primer pair useful for producing an amplicon useful for detecting the presence and/or absence of DNA derived from transgenic soybean event MON87751 in a sample. Such a kit would employ a method comprising contacting a target DNA sample with a primer pair as described herein, then performing a nucleic acid amplification reaction sufficient to produce an amplicon comprising a DNA molecule having at least one sequence selected from SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10; SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, and SEQ ID NO:26, and then detecting the presence and/or absence of the amplicon. Such a method may also include sequencing the amplicon or a fragment thereof, which would be determinative of, i.e. diagnostic for, the presence of the soybean event MON87751 specific DNA in the target DNA sample. Other primer pairs may be readily designed by one of skill in the art and should comprise at least 15, at least 16, at least 17, at least 18, at least 19, at least 20, at least 21, at least 22, at least 23, at least 24, at least 25, at least 26, at least 27, at least 28, at least 29, or at least 30 contiguous nucleotides of sequences provided in, but not limited to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10; SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, and SEQ ID NO:26 and be sufficiently unique to soybean event MON87751 DNA in order to identify DNA derived from the event.

The kits and detection methods of the invention are useful for, among other things, identifying soybean event MON87751, selecting plant varieties or hybrids comprising soybean event MON87751, detecting the presence of DNA derived from the transgenic soybean plants comprising event MON87751 in a sample, and monitoring samples for the presence and/or absence of soybean plants comprising event MON87751 or plant parts derived from soybean plants comprising event MON87751.

The sequence of the heterologous DNA insert, junction sequences, or flanking sequences from soybean event MON87751 can be verified (and corrected if necessary) by amplifying such sequences from the event using primers derived from the sequences provided herein followed by standard DNA sequencing of the amplicon or of the cloned DNA.

The following examples are included to demonstrate examples of certain preferred embodiments of the invention. It should be appreciated by those of skill in the art that the techniques disclosed in the examples that follow represent approaches the inventors have found function well in the practice of the invention, and thus can be considered to constitute examples of preferred modes for its practice. However, those of skill in the art should, in light of the present disclosure, appreciate that many changes can be made in the specific embodiments that are disclosed and still obtain a like or similar result without departing from the spirit and scope of the invention.

DEPOSIT INFORMATION

A deposit of a representative sample of *Glycine max* seed containing event MON87751 DNA has been made on Feb. 28, 2013 according to the Budapest Treaty with the American Type Culture Collection (ATCC) having an address at 10801 University Boulevard, Manassas, Va. USA, Zip Code 20110, and assigned ATCC Accession No. PTA-120166. Access to the deposits will be available during the pendency of the application to the Commissioner of Patents and Trademarks and persons determined by the Commissioner to be entitled thereto upon request. Upon issuance of the patent, all restrictions upon availability to the public will be irrevocably removed. The deposit will be maintained in the depository for a period of 30 years, or 5 years after the last request, or for the effective life of the patent, whichever is longer, and will be replaced as necessary during that period.

EXAMPLE 1

This example describes the transformation and selection of soybean event MON87751. The expression of foreign genes in plants is known to be influenced by their chromosomal position, perhaps due to chromatin structure (e.g., heterochromatin) or the proximity of transcriptional regulation elements (e.g., enhancers) close to the integration site (Weising, 1988). For this reason, it is often necessary to screen a large number of events in order to identify an event characterized by optimal expression of an introduced gene of interest. For example, it has been observed in plants and in other organisms that there may be wide variation in the levels of expression of an introduced gene among events. There may also be differences in spatial or temporal patterns of expression, for example, differences in the relative expression of a transgene in various plant tissues, that may not correspond to the patterns expected from transcriptional regulatory elements present in the introduced gene construct. For these reasons, eleven different expression vectors were generated and tested in transformed soybean during the selection of event MON87751.

Eleven different expression constructs were transformed and tested in plants. The individual expression constructs varied in the combination of the use of expression elements, i.e., enhancer (E), promoter (P), leader (L), introns (I), chloroplast targeting peptide (CTP), and 3' transcription termination and polyadenylation signal (T). Also, T-DNA segments contained two expression cassettes encoding both Cry proteins (Cry2Ab and Cry1A.105), or contained one expression cassette encoding a single Cry protein, i.e., Cry2Ab or Cry1A.105. A further variation in the expression constructs with the T-DNA segments containing both Cry2Ab and Cry1A.105 expression cassettes was the relative orientation of the two cassettes encoding the Cry proteins. Specifically, the two Cry protein expression cassettes were either positioned in a relative tandem orientation of transcription so that expression from each promoter of the respective Cry proteins proceeds in the same direction, but each from their separate respective promoters (see FIG. 2), or the two Cry protein expression cassettes were in a reversed orientation so that expression from each promoter of the two Cry proteins is away from a point centered between the two promoters, i.e., transcription of each Cry protein expression cassette proceeds in opposite directions and does not converge (see FIG. 2). The DNA sequence encoding Cry1A.105 was sequence diversified in constructs 4, 6, 7, 8, and 9, compared to constructs 1 and 3. In yet a further variation, in two of the constructs with the two Cry expression cassettes oriented in reverse orientation of transcription, transcription enhancers were positioned between the diverging promoters (see FIG. 2).

The eleven expression constructs were transformed at three separate times, by *Agrobacterium*-mediated transformation of soybean meristem tissue. The method was described in U.S. Pat. No. 8,030,544, which allows for the generation of transformed plants without utilization of callus. Briefly, meristem tissues were excised from the embryos of germinated A3555 soybean seed (Asgrow, St Louis, Mo.). Construct 1 comprised two separate T-DNA segments, each bounded by *Agrobacterium* border sequences (T-DNA segment). The first T-DNA segment of the transformation construct contained two expression cassettes with the first expression cassette encoding a region of the Tn7 adenylyltransferase gene from *Escherichia coli* (which confers spectinomycin and streptomycin resistance; aadA-SPR) and is used for selection; and the second expression cassette encoding a region of the sucrose phosphorylase gene from *Agrobacterium tumefaciens* strain C58 (which catalyzes the conversion of sucrose to fructose and glucose-1-phosphate; STR+OriRi) and is used as a scorable marker. The second T-DNA segment of the different transformation constructs contained either one expression cassette encoding only Cry2Ab (constructs 2, 5, 10 or 11) or an expression cassette encoding only Cry1A.105 (constructs 3 or 6); or the second T-DNA segment of the different transformation constructs contained one expression cassette encoding Cry2Ab and one expression cassette encoding Cry1A.105 (constructs 1, 4, 7, 8, or 9) (illustrated in FIG. 2). Because each T-DNA segment of the transformation construct is bounded by separate *Agrobacterium* border sequences, the T-DNA segment comprising the selection and scorable marker cassettes may integrate into the soybean cell genome at a site that is different from the site of integration of the T-DNA segment encoding the Cry2Ab and/or Cry1A.105 expression cassettes. Thus, events can be screened for segregation and loss of the selection and scorable marker sequences. All events were selected for absence of the backbone and absence of the selection/scorable marker cassette sequences. After co-culturing with *Agrobacterium* carrying the transformation construct, the meristems were placed on selection medium containing spectinomycin, carbenicillin disodium salt, cefotaxime sodium salt, and ticarcillin disodium salt/potassium clavulanate mixture to inhibit the growth of untransformed plant cells and excess *Agrobacterium*. The meristems were then placed in media conducive to shoot and root development. Rooted plants (R0) with normal phenotypic characteristics were selected and transferred to soil for growth and further assessment.

The expression construct 1, used to generate event MON87751, contained a T-DNA segment encoding two different Cry proteins, in a 5' to 3' relative order of plant expression elements (with or without intervening sequences): a promoter, leader and first intron derived from the *Arabidopsis thaliana* Actin 2 gene(P-At.Act2), a chimeric coding sequence comprised of the N-terminal chloroplast transit peptide coding sequence derived from the *Arabidopsis* 5-enolpyruvylshikimate-3-phosphate synthase (EPSPS) gene fused in frame to a gene encoding Cry2Ab (which encodes a protein that confers insect resistance) from *Bacillus thuringiensis* (Bt) with nucleotides modified for plant expression (CTP2-Cry2Ab), a 3' transcription termination and polyadenylation element (3' UTR) derived from an *Oryza sativa* metallothionein-like protein gene (T.OsMth), an intervening sequence between the first Cry protein expression cassette and the second Cry protein expression cassette; a promoter and leader derived from the *Arabidopsis* ribulose 1,5-bisphosphate carboxylase small subunit 1A gene (P-At.RbcS4), this promoter-leader is linked to a chimeric coding sequence comprised of chloroplast transit peptide coding sequence derived from the *Arabidopsis* ribulose 1,5-bisphosphate carboxylase small subunit 1A protein gene (CTP1) which also contained coding sequence encoding a repeat of the transit peptide cleavage site and 3 amino acids from the mature protein fused in frame with a gene encoding Cry1A.105 (which encodes a protein that confers insect resistance), composed of segments of genes encoding Cry1Ab1 (domains I & II), Cry1Fa1 (domain III), and Cry1Ac1 (protoxin domain) from *Bacillus thuringiensis* (Bt) with nucleotides modified for plant expression, a 3' UTR (T-Mt.Pt1) derived from the *Medicago truncatula* phosphate transporter 1 gene. In the construct 1 expression cassette, the T-DNA cassette containing the two separate Cry2Ab and Cry1A.105 expression cassettes has an *Agrobacterium* right border on the arbitrarily designated 5' end, which is 5' to the Cry2Ab cassette; and an *Agrobacterium* left border on the arbitrarily designated 3' end, which is 3' to the Cry1A.105 cassette. The Cry2Ab cassette (promoter through terminator) is at positions 123-3785 in SEQ ID NO:9, and the Cry1A.105 cassette (promoter through terminator) is at positions 3831-9754 in SEQ ID NO:9.

Figure 1:
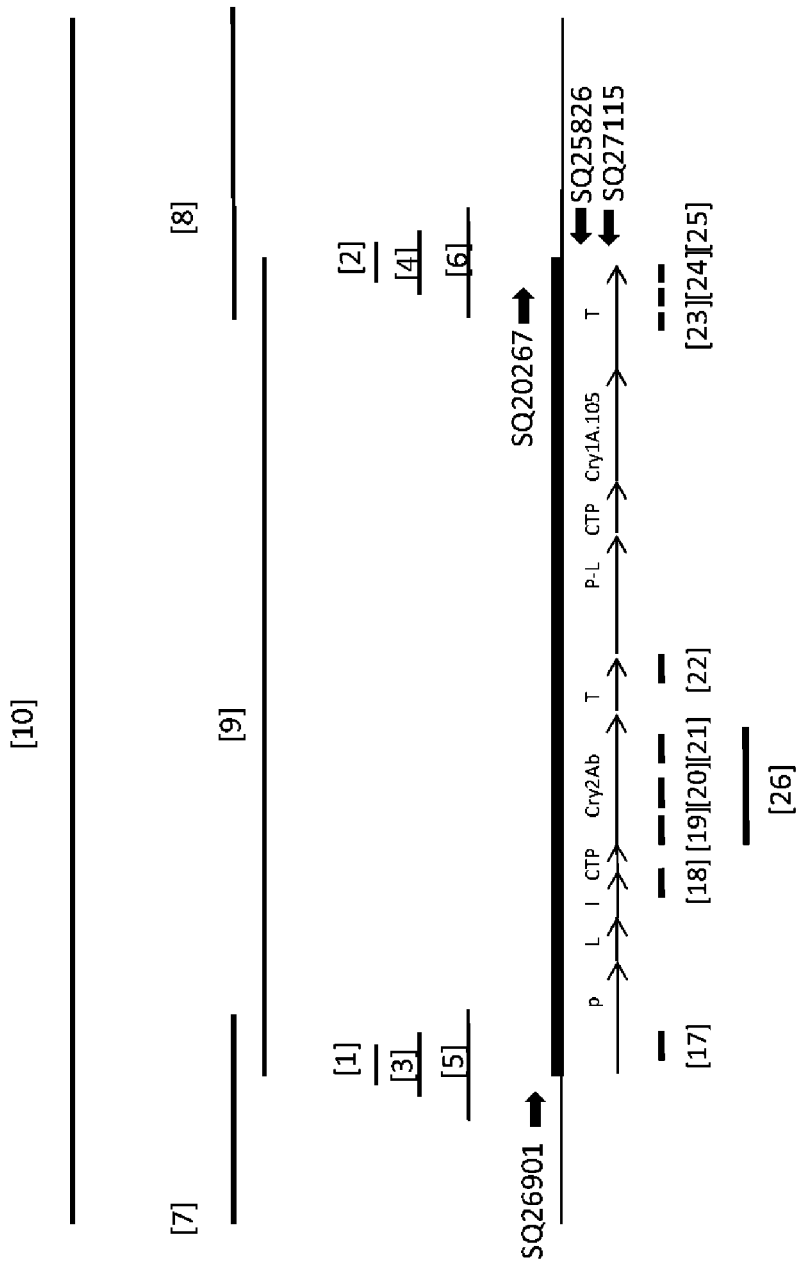
FIG. 1 is a diagrammatic representation of the relative positions, illustrated by each horizontal line, of the segments of the heterologous transgenic DNA, the flanking genomic DNA, the arbitrarily designated 5' and 3' genomic/inserted DNA junctions, and relative positions of sequence unique to event MON87751 within the heterologous transgenic DNA which may be used to identify soybean event MON87751; the horizontal lines labeled [1], [2], [3], [4], [5], [6], [7], [8], [9], [10], [17], [18], [19], [20], [21], [22], [23], [24], [25], and [26] correspond to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, and SEQ ID NO:26, respectively; the horizontal line with a thick bar represents the composite of the heterologous transgenic DNA inserted in event MON87751 (SEQ ID NO:9) and both the 5' and 3' flanking genomic DNA and is a representation of SEQ ID NO:10 containing SEQ ID NO:7, SEQ ID NO:9, and SEQ ID NO:8; the thick horizontal arrows designated SQ26901, SQ20267, SQ25826, and SQ27115, correspond to SEQ ID NO:15, SEQ ID NO:11, SEQ ID NO:12, and SEQ ID NO:14, respectively; the thin horizontal arrows represent the relative organization of the two separate expression cassettes of the heterologous transgenic inserted DNA of event MON87751, P represents a promoter element, L represents a leader, P-L represents a promoter and leader, I represents an intron, CTP represents a chloroplast transit peptide, Cry2Ab represents the coding region for Cry2Ab protein, T=3' transcription termination and polyadenylation element (3' UTR), and Cry1A.105 represents the coding region for Cry1A.105 protein.
Figure 2:
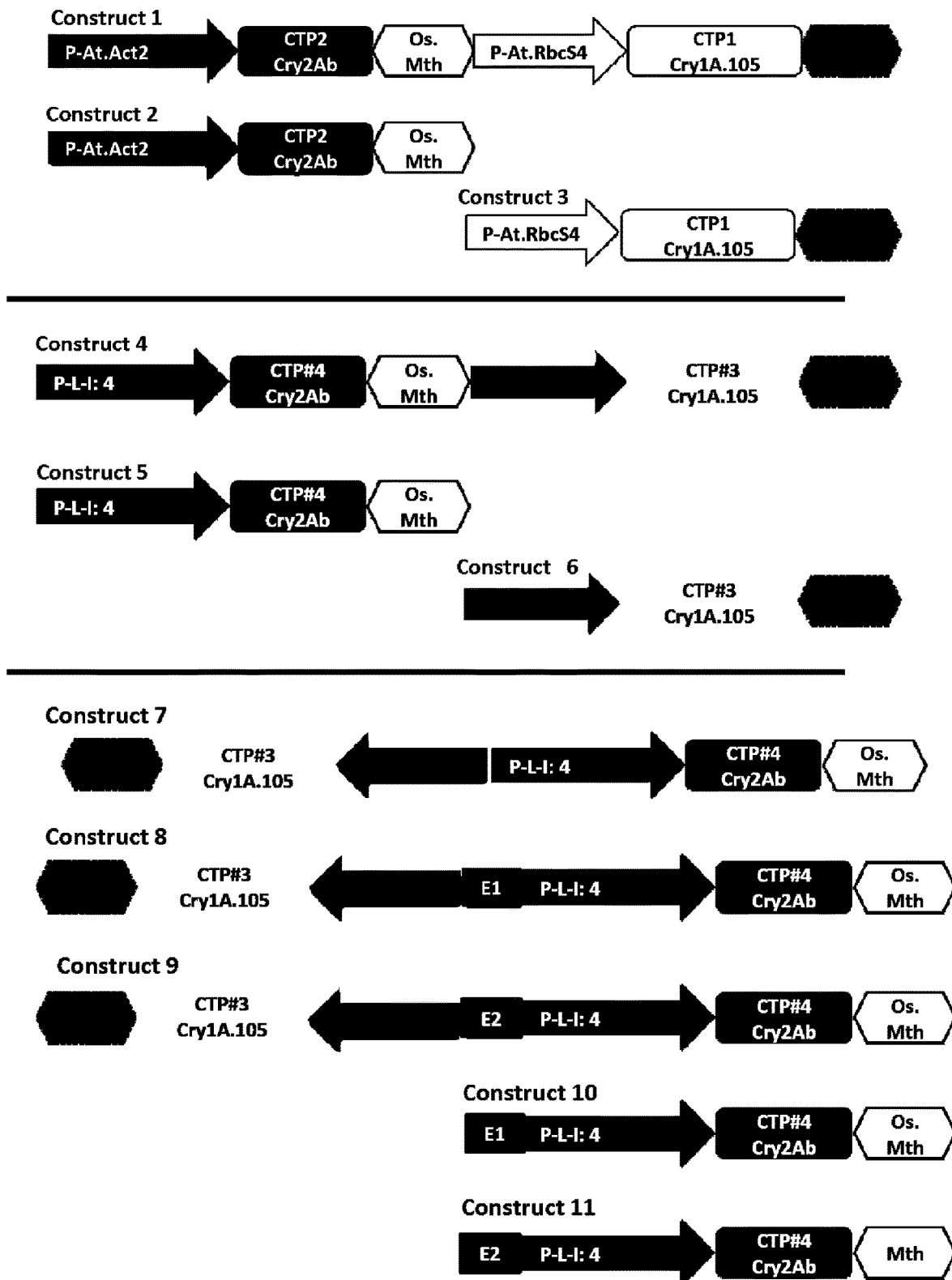
FIG. 2 illustrates the T-DNA segment encoding the Cry protein expression cassette(s) in the eleven transformation constructs used to generate transgenic soybean events evaluated during selection of soybean event MON87751, and the composition of each Cry protein expression cassette within each construct.

The T-DNA cassette for construct 2 (Cry2Ab) and for construct 3 (Cry1A.105) contained single Cry-protein encoding cassettes with the same elements for the respective Cry-protein encoding genes used in construct 1, see FIG. 2.

Constructs 4, 5, and 6 were similar in element orientation to constructs 1, 2, and 3, respectively, but with differing promoter-leader-intron and chloroplast transit peptide for both the Cry2Ab and Cry1A.105 cassettes. The terminators for the corresponding Cry protein cassettes (Cry2Ab with T-Os.Mth, or Cry1A.105 with T-Mt.Pt1) were identical in all expression constructs 1 through 11 (see FIG. 2).

The promoter-leader-intron and chloroplast transit peptide, Cry-protein encoding sequence, and terminator used for both the Cry2Ab and Cry1A.105 cassettes in each of the constructs 7-11 were identical to those used in constructs 4, 5, and 6. However, for constructs 7, 8, and 9 the orientation of the Cry2Ab cassette and the Cry1A.105 cassette were inverted or reversed relative to one another and the orientation of transcription was in opposite directions, each from their respective promoters, see FIG. 2. Constructs 7, 8, and 9 differed in the absence (construct 7) of an enhancer between the two cassettes, or the presence of an enhancer; construct 8 with enhancer 1 (E1), or construct 9 with enhancer 2 (E2), see FIG. 2. Construct 10 and construct 11 were single Cry2Ab cassettes with either E1 (construct 10) or E2 (construct 11).

Following transformation, and transfer of (R0) events to soil, extensive molecular, agronomic, and phenotypic analysis was done to select events for further testing. Additionally, events were self-pollinated and the resulting seed from the selected events was used for field and additional molecular testing.

The molecular testing included the following: assays to determine copy number, assays to determine integrity of both Cry protein containing expression cassettes (constructs 1, 4, 7, 8, and 9), presence of Cry protein encoding T-DNA cassette (single Cry protein expression cassettes (constructs 2, 3, 6, 10, or 11) or two Cry protein expression cassettes (constructs 1, 4, 7, 8, or 9)); assays to determine protein expression as measured by ELISA, and assays to determine segregation ratio of the T-DNA expression cassette (1:2:1 or 1:3). Agronomic assays included (for R0 events generated from constructs 1, 2, and 3, insect efficacy by leaf disc bioassay for two pest species (*Anticarsia gemmatalis* (velvetbean caterpillar, VBC) and *Chrysodeixis includens* (soybean looper, SBL)). R0 plants were grown to maturity, events were self-pollinated, and seed set for each event was determined.

The number of R0 events generated by transformation with the 11 individual constructs and transferred to soil varied, and ranged from 420 events to greater than 5000 events (see Table 1). For the transformation with the construct 1, from which event MON87751 was generated, there were a total of 1102 R0 plants rooted into soil, of which from these only 281 events passed the initial molecular analysis. The additional molecular, agronomic and phenotypic analysis of these 281 events which were generated by transformation with construct 1 resulted in only 29 R1 events evaluated for additional greenhouse analysis.

TABLE 1

R0 events produced from the eleven transformation constructs showing the number of events transferred to soil and the number of events passing a copy number assay.

| Construct | # events to soil | # events passing copy number assay |
|---|---|---|
| Construct 1 | 1102 | 281 |
| Construct 2 | 420 | 150 |
| Construct 3 | 420 | 107 |
| Construct 4 | 5544 | 209 |
| Construct 5 | 579 | 24 |
| Construct 6 | 588 | 32 |
| Construct 7 | 630 | 33 |
| Construct 8 | 1260 | 47 |
| Construct 9 | 1260 | 51 |
| Construct 10 | 504 | 12 |
| Construct 11 | 504 | 18 |

For the 29 R1 events generated from transformation with construct 1 and evaluated for further analysis, the R1 seed was planted in a greenhouse for analysis of the R1 events with assays including: (a) R1 germination (100% germination); (b) identification of homozygous plants; (c) confirmation PCR analysis that the homozygous plants no longer contained the selection/scorable marker sequence (it had segregated independently); (d) insect efficacy as determined by leaf disc bioassay for *C. includens* (SBL); and (e) insect efficacy as determined by leaf disc bioassay for *Spodoptera frugiperda* (fall armyworm, FAW), (f) protein expression by ELISA analysis on V7 stage leaf tissue, advancing events with Cry2Ab and Cry1A.105 protein levels over >4 ppm. In addition to the molecular analysis and insect leaf disc bioassay results, agronomic phenotype observations and seed set from four selections/event were collected. Based on the totality of these data, R2 seed from 21 of R1 events generated by transformation with construct 1 were evaluated in agronomic field trials and efficacy screenhouse trials.

EXAMPLE 2

Agronomic field trials were designed to evaluate the phenotypic characteristics and yield of soybean events expressing Cry2Ab and Cry1A.105 compared to the control, A3555 (parental background). In these agronomic field trials, the controls and events were of soybean variety A3555, with a relative maturity group 3 (RM3). The trials were planted under a randomized complete block design (RCBD) over four seasons and two geographic locations. In one geographic location the agronomic field trials were conducted at 25 field sites in each season, and in a second geographic location the agronomic field trials were conducted at 14 field sites in each season. Standard agronomic practices were followed in the planting and data collection for all trials. The data collected included emergence rating, seedling vigor, flowering date, flower color observation, phenotype observation, pubescence color, maturity, lodging, plant height, shattering score, harvest date, seed weight/plot, seed moisture/plot, and yield in bushels per acre (bu/ac).

For data analysis, some locations were dropped due to pre-harvest quality issues (i.e., standing water, inadequate soil moisture, poor emergence, late season pod shattering due to hail storm), or some locations were dropped due to a coefficient of variation (CV) above 15% and/or a high location quality index (LQI).

Across all locations tested, the phenotype measures taken indicated that the agronomic ratings for the events were within the normal range of the control, A3555. Not all observations were taken at all sites and some data, for example emergence, may have been collected but yield was not determined because the location was dropped for issues which occurred post collection of the early phenotype data.

For the agronomic field trials, the number of events generated by construct 1, 2, 3, 4, 5, or 6 and tested at each field trial in two geographic locations, and the soybean event generation tested (i.e. R3, R4, R5, R6, or R7) is shown in Table 2.

TABLE 2

Number of events (and soybean event generation) tested per construct during two seasons and two geographic locations of agronomic field trials (n.t. means not tested).

| | Season 1/ location 2 | Season 1/ location 1 | Season 2/ location 2 | Season 2/ location 1 |
|---|---|---|---|---|
| Construct 1 | 12 (R3) | 10 (R3) | 3 (R6) | 3 (R7) |
| Construct 2 | 2 (R3) | 2 (R3) | 1 (R4) | 1 (R5) |
| Construct 3 | 3 (R3) | 3 (R3) | 1 (R4) | 1 (R5) |
| Construct 4 | nt. | 9 (R3) | nt. | nt. |
| Construct 5 | nt. | 3 (R3) | nt. | nt. |
| Construct 6 | nt. | 3 (R3) | nt. | nt. |

Meta analysis of agronomic field trials for events tested across each season, each geographic location, and each field trial testing mean yield (bu/acre) demonstrated that there was a statistically significant increase in yield for event MON87751 compared to control A3555 (Table 2). The events expressing only Cry2Ab did not have a statistically significant difference in yield compared to the control A3555, see Table 3. The event expressing only Cry1A.105 had a statistically significant decrease in yield compared to the control A3555, see Table 3.

TABLE 3

Meta analysis of agronomic field trials for events tested across each season, each geographic location, and each field trial testing yield when compared to non-transgenic soybean line A3555.

| Construct | GOI | Event | Mean yield (bu/acre) | Delta | PERC | P_value | LSD05 | LSD10 |
|---|---|---|---|---|---|---|---|---|
| Construct 1 | Cry2Ab + Cry1A.105 | MON87751 | 68.16 | 1.83 | 2.76 | 0.00 | 1.17 | 0.98 |
|  |  | 8 | 64.88 | −1.45 | −2.19 | 0.02 | 1.17 | 0.98 |
|  |  | 10 | 66.59 | 0.26 | 0.39 | 0.66 | 1.17 | 0.98 |
| Construct 2 | Cry2Ab | 20 | 67.39 | 1.06 | 1.60 | 0.08 | 1.17 | 0.98 |
| Construct 3 | Cry1A.105 | 29 | 64.06 | −2.27 | −3.42 | 0.00 | 1.17 | 0.98 |
|  |  | A3555 | 66.33 |  |  |  |  |  |

EXAMPLE 3

Efficacy screenhouse trials were conducted to evaluate the efficacy of experimental soybean events expressing both Cry proteins from an insertion of a T-DNA segment from a single construct with two expression cassettes (i.e., both Cry2Ab and Cry1A.105), or single Cry proteins (i.e., Cry2Ab only, or Cry1A.105 only) against artificial infestations of lepidopteran pest populations contained in screenhouse enclosures. The comparison of single- to double-gene events was used to determine the relative contribution of each single Cry protein towards the efficacy observed in the double-gene expression construct events. The screenhouse trials were conducted during multiple seasons in two geographic locations. In one geographic location, 5 target pest species were tested: *Anticarsia gemmatalis* (velvetbean caterpillar, VBC), *Chrysodeixis includens* (soybean looper, SBL), *Spodoptera eridania* (southern armyworm, SAW), *Spodoptera frugiperda* (fall armyworm, FAW), and *Helicoverpa zea* (soybean podworm, SPW). In the second geographic location, 3 target pest species were tested: *Crocidosema aporema* (bean shoot moth, BSM), *Rachiplusia nu* (sunflower looper, SFL), and *Spodoptera frugiperda* (fall armyworm, FAW).

The events (i.e., entries) which were tested in these screenhouse trials were generated from transformations with each of the separate transformation constructs. Transformation events generated from construct 1, 2, or 3, were evaluated in the R2 generation in screenhouse trials and included twenty events expressing both proteins (events generated from transformation with construct 1), six events expressing only Cry2Ab (events generated from transformation with construct 2), and six events expressing only Cry1A.105 (events generated from transformation with construct 3). Of these, 12 events with both Cry2Ab and Cry1A.105 (construct 1), two events with Cry2Ab-only (construct 2), and three events with Cry1A.105-only (construct 3) were evaluated in the R3 generation in screenhouse trials. Eleven of the events with both Cry2Ab and Cry1A.105 (construct 1) were further evaluated in the R4 generation screenhouse trials. Three events with both Cry2Ab and Cry1A.105 (construct 1), one event with Cry2Ab-only (construct 2), and one event with Cry1A.105-only (construct 3) were evaluated in the R5, R6, and R7 screenhouse trials. Ten events expressing Cry2Ab and Cry1A.105 (events generated from transformation with construct 4), three Cry2Ab-only events (events generated from transformation with construct 5), and three Cry1A.105-only events (events generated from transformation with construct 6) were evaluated in the R3 generation to screenhouse trials. Two events with both Cry2Ab and Cry1A.105, one event with Cry2Ab-only, and one event with Cry1A.105-only were evaluated in the R4 screenhouse trials, and one event each was evaluated in the R5 screenhouse trials. Three events expressing both Cry2Ab and Cry1A.105 in opposing 5' to 3' orientation with an enhancer (events generated from transformation with construct 8), 3 stacked events expressing both Cry2Ab and Cry1A.105 in opposing 5' to 3' orientation without an enhancer (events generated from transformation with construct 7), and 2 Cry2Ab-only events (events generated from transformation with construct 10) were evaluated in the R2 generation were evaluated in screenhouse trials. The positive transgenic soybean controls included MON87701 or event GM_A19478 (generated at the same time as MON87701), and both expressing Cry1Ac. Non-transgenic soybean lines A3555 (parental background for MON87751 events, relative maturity 3 (RM3)) and A5547 (parental background for MON87701 and GM_A19478, RM5) were included in all screenhouse and field trials as negative controls. The non-transgenic soybean line AG3705 was included as a white flower check in some trials.

Standard practices were followed in establishing and conducting the screenhouse trials. The plots were evaluated once after each infestation at the time of maximal damage to the negative checks (usually 3-4 weeks after pupae were placed within the screenhouse). At each evaluation, the following agronomic observations were recorded: the date and the stage of plant growth. Additionally, for defoliating insects, an estimated percent defoliation in each plot was recorded. For *C. aporema*, ten plants were randomly selected in each plot and the number of plants with damage was recorded. In some cases the numbers of live larvae were also recorded.

Defoliation data were subjected to ANOVA to determine significant sources of variability among line and replicate for each insect at each location at the 0.05 probability level (P). Significant differences among means were determined using the Tukey-Kramer test (Kramer 1956) at P=0.05.

Three small-plot screenhouse trials were conducted in the second geographic location during one season using *R. nu* and *C. aporema* for infestation. The trial design included Randomized Complete Block Design (RCBD) test blocks with three replicates per event or control, with events tested shown in Table 4. One trial was infested with *C. aporema* during mid-vegetative stage of soybean growth and again at early reproductive stage of soybean growth. Two trials were infested with *R. nu* during mid-vegetative stage of soybean growth.

For the *C. aporema* trial, very heavy pressure was achieved. Replicate was not a significant source of variability in damage (F=0.8794; df=2, 69; P=0.4196), but event was highly significant (F=11.9398; df=23, 48; P<0.0001). The maximum percent of plants damaged (Table 4) averaged 83-100% in the negative checks but was absent in the Cry1Ac positive control. Events generated from transformation construct 1 and expressing Cry2Ab and Cry1A.105 exhibited 0-13% of plants damaged, while those expressing Cry2Ab-only or Cry1A.105-only exhibited 10-17% and 10-13%, respectively. The small, albeit significant, numbers of plants recorded as damaged in this trial may be due to the criteria used by the individuals when recording the damage rating.

For the R. nu trials, heavy pressure was achieved in one screenhouse trial. Replicate was not a significant source of variability in defoliation (F=0.203; df=2, 69; P=0.8167), but event was highly significant (F=20.2461; df=23, 48; P<0.0001). Maximum defoliation (Table 4) averaged 60-63% in the negative checks but was absent in the Cry1Ac positive control and events generated from transformation construct 1 expressing Cry2Ab+Cry1A.105 or events generated from transformation construct 2 expressing Cry2Ab-only. Events generated from transformation construct 3 expressing Cry1A.105-only exhibited slightly higher defoliation (4-10%). Moderately heavy pressure was achieved in the second screenhouse trial evaluating R. nu. Replicate was not a significant source of variability in defoliation in either trial (F=0.2542; df=2, 69; P=0.7763), but event was highly significant (F=16.1793; df=23, 48; P<0.0001). Maximum defoliation (Table 4) averaged 38-40% in the negative checks but was negligible in the Cry1Ac positive control (4%) and absent in events generated with construct 1 and expressing Cry2Ab+Cry1A.105 or events generated with construct 2 and expressing Cry2Ab-only. Events generated with construct 3 and expressing Cry1A.105-only exhibited slightly higher defoliation (2-7%).

In these screenhouse trials, soybean event MON87751 exhibited no damaged plants due to infestation of the insect pests, C. aporema or R. nu, which was significant compared to the damage and/or defoliation of the controls in the same trial (Table 4).

In a subsequent season of small-plot screenhouse trials conducted in the second geographic location, local lab populations of R. nu, C. aporema and S. frugiperda were used for infestation. The protocols for conducting the trials were essentially as described above, and with events and controls tested shown in Table 5.

For the trial infested with C. aporema, heavy pressure was achieved. Replicate was not a significant source of variability in damage (F=0.2742; df=2, 33; P=0.7619), but event was highly significant (F=8.2313; df=11, 24; P<0.0001). Maximum damage averaged 4.2-5.5 damaged points per plant in the negative checks, with 80-100% of plants exhibiting damage, but was negligible in the positive control and all test events (Table 5).

For the trial infested with R. nu, moderately heavy pressure was achieved. Replicate was not a significant source of variability in damage (F=0.041; df=2, 33; P=0.9599), but event was highly significant (F=143.5526; df=11, 24; P<0.0001). Maximum damage averaged 33.3-40.0% defoliation in the negative checks (well above economic threshold) but was absent or negligible in the positive control and all test events except the events generated by transformation with construct 6 expressing only TIC105 (Table 5).

For the trial infested with S. frugiperda, light pressure was achieved. Replicate was not a significant source of variability in damage (F=0.1187; df=2, 33; P=0.8884), but event was highly significant (F=12.8602; df=11, 24; P<0.0001). Maximum damage averaged 7.5-15.0% defoliation in the negative checks—just reaching the economic threshold. Some damage was also noted in events expression only Cry2Ab generated by transformation with either construct 2 or construct 5, but damage was absent or negligible in the positive control and all other test events (Table 5).

In these screenhouse trials, soybean event MON87751 exhibited no damaged plants due to infestation of the insect pests, C. aporema, R. nu, S. frugiperda, which was significant when compared to damage to the negative controls in the same trial (Table 5). Soybean event MON87751 had significantly less damage from R. nu when compared to transgenic soybean events generated by transformation with construct 6 expressing only Cry1A.105 (Table 5), though it is noted that there is lower expression of Cry1A.105 protein in the events generated by transformation with construct 6. These results also demonstrate for the first time the expanded spectrum of control of the insect pest S. frugiperda.

TABLE 4

Damage by C. aporema and defoliation by R. nu larvae to events generated using constructs 1, 2, or 3 and evaluated in artificially-infested screenhouses.

| Construct | GOI | Event | % Plants damaged (season maximum) Crocidosema aporema | | % Defoliation (season maximum) Rachiplusia nu | | | | |
|---|---|---|---|---|---|---|---|---|---|
| | | | | | Screenhouse trial 1 | | Screenhouse trial 2 | | |
| | Cry1Ac | GM_A19459 | 0 ± 0 | b | 0 ± 0 | d | 3.7 ± 0.0 | bc |
| Construct 1 | Cry2Ab + Cry1A.105 | 2 | 6.7 ± 6.7 | b | 0 ± 0 | d | 0 ± 0 | c |
| | | 3 | 0 ± 0 | b | 0 ± 0 | d | 0 ± 0 | c |
| | | 4 | 13.3 ± 3.3 | b | 0 ± 0 | d | 0 ± 0 | c |
| | | MON87751 | 0 ± 0 | b | 0 ± 0 | d | 0 ± 0 | c |
| | | 7 | 6.7 ± 6.7 | b | 0 ± 0 | d | 0 ± 0 | c |
| | | 8 | 13.3 ± 8.8 | b | 0 ± 0 | d | 0 ± 0 | c |
| | | 9 | 3.3 ± 3.3 | b | 0 ± 0 | d | 0 ± 0 | c |
| | | 10 | 13.3 ± 6.7 | b | 0 ± 0 | d | 0 ± 0 | c |
| | | 11 | 3.3 ± 3.3 | b | 0 ± 0 | d | 0 ± 0 | c |
| | | 14 | 6.7 ± 6.7 | b | 0 ± 0 | d | 0 ± 0 | c |
| | | 18 | 13.3 ± 8.8 | b | 0 ± 0 | d | 0 ± 0 | c |
| | | 19 | 13.3 ± 8.8 | b | 0 ± 0 | d | 0 ± 0 | c |
| Construct 2 | Cry2Ab | 20 | 10.0 ± 10.0 | b | 0 ± 0 | d | 0.3 ± 0.0 | c |
| | | 22 | 16.7 ± 3.3 | b | 0 ± 0 | d | 0 ± 0 | c |
| Construct 3 | Cry1A.105 | 29 | 10.0 ± 10.0 | b | 10.0 ± 0.1 | cd | 5.3 ± 0.0 | bc |
| | | 30 | 13.3 ± 8.8 | b | 6.7 ± 0.0 | cd | 2.0 ± 0.0 | c |
| | | 31 | 10.0 ± 5.8 | b | 3.7 ± 0.0 | d | 7.0 ± 0.0 | bc |
| | Negative | A3555 | 83.3 ± 16.7 | a | 63.3 ± 0.0 | a | 38.3 ± 0.1 | a |
| | | A5547 | 100 ± 0 | a | 60.0 ± 0.0 | a | 40.0 ± 0.1 | a |

Means within columns followed by the same letter are not significantly different (Tukey-Kramer means test, P < 0.05).

TABLE 5

Maximum damage by *C. aporema*, and mean percent defoliation by *R. nu* and *S. frugiperda* larvae in artificially-infested screenhouses evaluating events generated with constructs 1, 2, 3, 4, 5, or 6 and compared to positive and negative controls.

| | | | Maximum damage[1, 2] (means ± S.E.) | | | | | | |
|---|---|---|---|---|---|---|---|---|---|
| | GOI | Event | *C. aporema*[1] | | *R. nu*[2] | | *S. frugiperda*[2] | |
| POS | Cry1Ac | GM_A19459 | 0 ± 0 | B | 0 ± 0 | D | 0.8 ± 0.8 | BC |
| Construct 1 | Cry2Ab + Cry1A.105 | MON87751 | 0 ± 0 | B | 0 ± 0 | D | 0 ± 0 | C |
| | | 8 | 0 ± 0 | B | 0 ± 0 | D | 0 ± 0 | C |
| | | 10 | 0 ± 0 | B | 0 ± 0 | D | 0 ± 0 | C |
| Construct 2 | Cry2Ab | 20 | 0.3 ± 0.3 | B | 0 ± 0 | D | 1.7 ± 0.8 | BC |
| Construct 3 | Cry1A.105 | 29 | 0 ± 0 | B | 0.8 ± 0.8 | D | 0 ± 0 | C |
| Construct 4 | Cry2Ab + Cry1A.105 | 32 | 0 ± 0 | B | 0 ± 0 | D | 0 ± 0 | C |
| | | 40 | 0.1 ± 0.1 | B | 0 ± 0 | D | 0 ± 0 | C |
| Construct 5 | Cry2Ab | 46 | 0 ± 0 | B | 2.0 ± 1.5 | D | 6.5 ± 2.2 | BC |
| Construct 6 | Cry1A.105 | 42 | 0 ± 0 | B | 13.3 ± 1.7 | C | 0 ± 0 | C |
| NEG | Negative | A3555 | 5.5 ± 2.2 | A | 33.3 ± 3.3 | B | 15.0 ± 2.9 | A |
| | | A5547 | 4.2 ± 0.3 | A | 40.0 ± 0.0 | A | 7.5 ± 2.5 | B |

Means within columns followed by the same letter are not significantly different (Tukey-Kramer means test, $P < 0.05$).
[1]Mean damaged points/plant.
[2]Mean percent defoliation One small-plot screenhouse trial was conducted in the first geographic location using infestation of a lab population of *H. zea*. The trial design included Randomized Complete Block Design (RCBD) test blocks with three replicates per event, with events and controls tested shown in Table 6. There were two infestations of *H. zea* and defoliation was assessed 19-27 days post-infest (R2-R3 stage of soybean growth) for the first infestation, and 25-28 days post-infest (R5 stage of soybean growth) for the second infestation. The results from the screenhouse trials testing the insect pest, *H. zea*, are as follows: moderately heavy pressure was achieved. Replicate was not a significant source of variability in defoliation ($F=0.326$; $df=2, 105$; $P=0.7225$), but event was highly significant ($F=13.8864$; $df=35, 72$; $P<0.0001$). Maximum defoliation (Table 6) averaged 32-33% in the negative checks but was negligible in the Cry1Ac positive control (1%) and events generated with construct 1 and expressing Cry2Ab+Cry1A.105 (2-4%). A somewhat higher defoliation was observed in events generated with construct 4 expressing Cry2Ab+Cry1A.105 (5-12%), events generated with construct 5 expressing only Cry2Ab (13-17%) or events generated with construct 6 expressing only Cry1A.105 (8-12%).

Soybean event MON87751 exhibited significantly less damage by *H. zea* in this screenhouse trial when compared to damage to the negative controls in the same trial. This level of control by *H. zea* is within acceptable commercial level of control for this soybean pest species. Additionally, in this screenhouse trial, soybean event MON87751 had significantly less damage when compared to transgenic soybean events generated with construct 5 expressing only Cry2Ab (Table 6), demonstrating expanded level of control. However, expression of Cry2Ab is lower in events generated with construct 5 than in events generated with construct 2, and the significant defoliation of events generated with construct 5 expressing only Cry2Ab may indicate that there may be reduced efficacy against *H. zea* by Cry2Ab in generated with construct 5.

TABLE 6

Maximum seasonal defoliation to events generated with constructs 1, 4, 5, or 6 by *H. zea* larvae in artificially-infested screenhouse trial when compared to positive and negative controls.

| Construct | GOI | Event | % Defoliation (season maximum) *H. zea* | |
|---|---|---|---|---|
| | Cry1Ac | GM_A19478 | 1.0 ± 0.0 | e |
| Construct 1 | Cry2Ab + Cry1A.105 | 2 | 3.0 ± 0.0 | cde |
| | | 3 | 2.3 ± 0.7 | de |
| | | 4 | 2.7 ± 0.3 | cde |
| | | MON87751 | 4.3 ± 0.7 | cde |
| | | 8 | 2.3 ± 0.3 | de |
| | | 9 | 2.0 ± 0.0 | de |
| | | 10 | 2.3 ± 0.3 | de |
| | | 11 | 4.3 ± 1.9 | cde |
| | | 14 | 3.3 ± 0.9 | cde |
| | | 18 | 3.7 ± 0.7 | cde |
| | | 19 | 2.3 ± 0.3 | de |
| Construct 4 | Cry2Ab + Cry1A.105 | 32 | 9.3 ± 0.7 | bcde |
| | | 33 | 5.0 ± 0.0 | cde |
| | | 34 | 7.0 ± 1.0 | bcde |
| | | 35 | 7.7 ± 1.5 | bcde |
| | | 36 | 8.7 ± 0.7 | bcde |
| | | 37 | 11.7 ± 1.7 | bcde |
| | | 38 | 8.7 ± 0.7 | bcde |
| | | 39 | 9.3 ± 0.7 | bcde |
| | | 40 | 7.7 ± 1.5 | bcde |
| | | 41 | 9.3 ± 0.7 | bcde |
| Construct 5 | Cry1A.105 | 42 | 11.0 ± 2.1 | bcde |
| | | 43 | 11.7 ± 1.7 | bcde |
| | | 44 | 7.7 ± 1.5 | bcde |
| Construct 6 | Cry2Ab | 45 | 13.3 ± 1.7 | bc |
| | | 46 | 16.7 ± 3.3 | b |
| | | 47 | 12.7 ± 3.7 | bcd |
| | Negative | A3555 | 33.3 ± 6.7 | a |
| | | A5547 | 31.7 ± 1.7 | a |

Means within columns followed by the same letter are not significantly different (Tukey-Kramer means test, $P < 0.05$).

In another season of small-plot screenhouse trials conducted in the first geographic location, resistance to infestation from lab populations of the insect pests *S. eridania* (1st-instar or 3rd-instar), *A. gemmatalis* (1st-instar), and *C. includens* (1st-instar) was tested. The results from these trials are as follows: extreme pressure was achieved with 1st-instar *S. eridania*, and moderate pressure was achieved with *A.*

*gemmatalis*. Maximum percent defoliation (means±S.E.) by *A. gemmatalis* (1st-instar) and *S. eridania* (1st-instar) larvae are reported in Table 7.

negative controls in the same trial (Table 7 and Table 8). Additionally, in these screenhouse trials, soybean event MON87751 had significantly less damage by *S. eridania*

TABLE 7

Maximum percent defoliation by *A. gemmatalis* (1st-instar) and *S. eridania* (1st-instar) larvae in artificially-infested screenhouses evaluating events generated with constructs 1, 2, 3, 4, 5, 6, 7, 8, and 10 and compared to positive and negative controls.

| | | | Maximum % defoliation (means ± S.E.) | | | |
|---|---|---|---|---|---|---|
| | Event | GOI | *A. gemmatalis* | | *S. eridania* | |
| POS | GM_A19478 | Cry1Ac | 0 ± 0 | B | 65.0 ± 6.5 | A |
| Construct 1 | MON87751 | Cry2Ab + Cry1A.105 | 0.5 ± 0.3 | B | 3.8 ± 2.1 | BC |
| | 10 | | 0.3 ± 0.3 | B | 1.8 ± 0.3 | C |
| Construct 2 | 20 | Cry2Ab | 0.3 ± 0.3 | B | 3.3 ± 1.0 | BC |
| Construct 3 | 29 | Cry1A.105 | 0.5 ± 0.3 | B | 52.5 ± 6.3 | A |
| Construct 4 | 40 | Cry2Ab + Cry1A.105 | 0 ± 0 | B | 16.3 ± 1.3 | BC |
| Construct 5 | 46 | Cry2Ab | 1.5 ± 1.2 | B | 15.0 ± 2.9 | BC |
| Construct 6 | 42 | Cry1A.105 | 0.5 ± 0.3 | B | 50.0 ± 0.0 | A |
| Construct 8 | 48 | eCry2Ab + Cry1A.105 | 1.8 ± 0.3 | B | 2.8 ± 0.8 | BC |
| | 49 | | 0 ± 0 | B | 1.8 ± 0.3 | C |
| | 50 | | 1.0 ± 0.4 | B | 2.3 ± 0.9 | BC |
| Construct 7 | 51 | Cry2Ab + Cry1A.105 | 0.5 ± 0.5 | B | 52.5 ± 11.8 | A |
| | 52 | | 1.0 ± 0.4 | B | 22.5 ± 2.5 | B |
| | 53 | | 0 ± 0 | B | 13.8 ± 2.4 | BC |
| Construct 10 | 54 | eCry2Ab | 0.5 ± 0.5 | B | 2.5 ± 0.9 | BC |
| | 55 | | 0 ± 0 | B | 3.5 ± 0.9 | BC |
| NEG | A3555 | Negative | 35.8 ± 8.0 | A | 58.8 ± 3.0 | A |
| | A5547 | | 35.5 ± 11.4 | A | 45.0 ± 6.5 | A |

Within columns means followed by the same letter are not significantly different (Tukey-Kramer means test at $P < 0.05$).

For the trials testing *C. includens* (1st-instar) and *S. eridania* (3rd-instar), extreme pressure was achieved for both of the insect pests. Maximum percent defoliation (means±S.E.) by *C. includens* (1st-instar) larvae and *S. eridania* (3rd-instar) larvae in these artificially-infested screenhouses is reported in Table 8.

($1^{st}$-instar and 3rd-instar) larvae when compared to transgenic soybean events expressing Cry1Ac (Table 7 and Table 8), demonstrating the expanded performance of event MON87751 to transgenic soybean event currently available for lepidopteran pest control. Further, in these screenhouse trials, soybean event MON87751 had significantly less

TABLE 8

Maximum percent defoliation by *C. includens* (1st-instar) and *S. eridania* (3rd-instar) larvae in artificially-infested screenhouses evaluating events generated with constructs 1, 2, 3, 4, 5, 6, 7, 8, and 10 and compared to positive and negative controls.

| Transformation | | | Maximum % defoliation (means ± S.E.) | | | |
|---|---|---|---|---|---|---|
| Construct | Event | GOI | *C. includens* | | *S. eridania* | |
| POS | GM_A19478 | Cry1Ac | 1.0 ± 0.7 | C | 78.8 ± 1.3 | A |
| Construct 1 | MON87751 | Cry2Ab + Cry1A.105 | 0.5 ± 0.3 | C | 13.8 ± 1.3 | D |
| | 10 | | 0 ± 0 | C | 11.3 ± 1.3 | D |
| Construct 2 | 20 | Cry2Ab | 0.8 ± 0.5 | C | 13.8 ± 2.4 | D |
| Construct 3 | 29 | Cry1A.105 | 3.5 ± 1.6 | C | 82.5 ± 4.8 | A |
| Construct 4 | 40 | Cry2Ab + Cry1A.105 | 3.3 ± 1.0 | C | 36.3 ± 5.5 | B |
| Construct 5 | 46 | Cry2Ab | 4.8 ± 1.0 | C | 30.0 ± 4.6 | BC |
| Construct 6 | 42 | Cry1A.105 | 9.8 ± 1.0 | C | 80.0 ± 4.6 | A |
| Construct 8 | 48 | eCry2Ab + Cry1A.105 | 0.3 ± 0.3 | C | 12.5 ± 2.5 | D |
| | 49 | | 0.3 ± 0.3 | C | 13.8 ± 1.3 | D |
| | 50 | | 2.0 ± 1.1 | C | 14.3 ± 0.8 | D |
| Construct 7 | 51 | Cry2Ab + Cry1A.105 | 40.0 ± 6.8 | B | 73.3 ± 3.3 | A |
| | 52 | | 4.0 ± 1.2 | C | 35.0 ± 2.9 | B |
| | 53 | | 4.8 ± 1.0 | C | 38.8 ± 4.3 | B |
| Construct 10 | 54 | eCry2Ab | 0.8 ± 0.5 | C | 15.0 ± 2.0 | CD |
| | 55 | | 0.5 ± 0.3 | C | 12.5 ± 1.4 | D |
| NEG | A3555 | Negative | 76.9 ± 5.3 | A | 79.4 ± 2.0 | A |
| | A5547 | | 65.0 ± 10.4 | A | 82.5 ± 2.5 | A |

Within columns means followed by the same letter are not significantly different (Tukey-Kramer means test at $P < 0.05$).

The results for these screenhouse trials show that soybean event MON87751 exhibited significantly less damage by *S. eridania* ($1^{st}$-instar or $3^{rd}$-instar), *A. gemmatalis* ($1^{st}$-instar), or *C. includens* (1st-instar) when compared to damage to the damage by *S. eridania* larvae when compared to [1] any of the events generated with constructs 4, 5, or 6 ($3^{rd}$-instar larvae), or events generated with construct 6 expressing only Cry1A.105 event ($1^{st}$ instar larvae), or events generated with construct 3 expressing only Cry1A.105 event (1st instar larvae and 3rd-instar larvae) and [2] when compared to events generated with construct 7 expressing Cry2Ab and Cry1A.105 without an enhancer (1st instar- and 3rd-instar larvae), demonstrating the superior performance of the event MON87751 to the events generated with constructs 4, 5, 6, or 7 (Table 7 and Table 8).

EXAMPLE 4

Open field efficacy trials were conducted to evaluate the efficacy of experimental soybean event MON87751 and events created using the different transformation constructs 1, 2, 3, 4, 5, and 6, against natural field infestations of lepidopteran pest populations. The comparison of events generated with construct 2 or 5 (expression of Cry2Ab only), and events generated with construct 3 or 6 (expression of Cry1A.105 only), to events generated with construct 1 or 4 (expression of both Cry1Ab and Cry1A.105) was used to determine the relative contribution of each single Cry protein (i.e. Cry2Ab only, or Cry1A.105 only) towards the efficacy observed in events expressing both Cry proteins (i.e., Cry2Ab and Cry1A.105) from a single construct. The efficacy field trials of native populations of endemic soybean pests were conducted over multiple seasons, at multiple field trial sites, and in three geographic locations.

In the initial efficacy field trials conducted in one geographic location, the events (i.e., entries) evaluated included twelve events generated by construct 1 and expressing both Cry proteins, Cry2Ab and Cry1A.105 (and including event MON87751), two events generated by construct 2 and expressing only Cry2Ab, and three events generated by construct 3 expressing only Cry1A.105. In the initial efficacy field trials conducted in a second geographic location, the events generated by constructs 1, 2 and 3 were evaluated and included 11 events expressing both Cry proteins, Cry2Ab and Cry1A.105 (generated from transformation with construct 1 and including event MON87751), two events expressing only Cry2Ab (events generated from transformation with construct 2), and three events expressing only Cry1A.105 (events generated from transformation with construct 3). In a second season of efficacy field trials conducted in 3 geographic locations, the events (i.e., entries) evaluated included three events expressing both Cry proteins, Cry2Ab and Cry1A.105 (events generated from transformation with construct 1 and including event MON87751), one event expressing only Cry2Ab (events generated from transformation with construct 2), and one event expressing only Cry1A.105 (events generated from transformation with construct 3). The events evaluated in the open field efficacy trials included generations R3 through R7.

For each efficacy field trial site, test blocks were planted and natural infestation by native pest populations of the target lepidopteran insects was allowed to occur. The test block remained untreated with insecticides for the target pests (Lepidoptera). However, the test blocks may have been sprayed to prevent significant damage by non-target insect pests. All experimental events were in the soybean germplasm background A3555, of relative maturity group 3 (RM3). The other entries in the trials included the positive control MON87701 (expressing Cry1Ac) or GM_A19459 (RM5); the negative parental check A3555 (purple flower, RM3); and the negative commercial check A5547 (white flower, MG5) or CMA5805 (white flower, RM5).

Standard practices were followed in establishing and conducting the open field efficacy trials. Larval incidence of lepidopteran pests, defoliation, and plant growth stage were recorded periodically (i.e., every 5-14 days) commencing with onset of target lepidopteran activity and ending when target lepidopteran activity ceased or plants reached R7 stage of growth. Pest incidence data was collected from rows 1 and 4 only to avoid plant damage in rows 2 and 3, which were harvested for yield data. Monitoring and recording of pest incidence data occurred as follows: defoliating lepidopterans (i.e., *A. gemmatalis, C. includens, R. nu, Spodoptera* spp.) were monitored using a drop cloth or vertical beating sheet, with at least two drop cloth or four vertical beating sheet samplings per plot. The total number of larvae for each target species encountered and the number of samplings within each plot were recorded as the mean number of larvae per m row (total number larvae÷ number samplings÷ cloth/sheet length in meters) for each target species encountered. Subsequent samplings were done in a manner which avoided repeated sampling in the same area of each plot. In the efficacy field trials conducted at one geographic location, data were also recorded at two trial sites for opportunistically for damage by *H. zea* by randomly selecting 20 or 33 plants/location, and recording the number with larval feeding damage. At a second geographic location, one trial was rated opportunistically for *H. zea* by randomly selecting 10 plants per plot and recording total number of pods and number of damaged pods per plant.

Data for infestation by *Elasmopalpus lignosellus* were recorded by counting the total number of plants in each plot with damage (wilted, dying, or dead) due to larval feeding. Damage data for this insect was taken at a single time point when maximal damage was noted.

In addition to target pests, non-targets pests, primarily those with potential for surpassing economic thresholds (e.g., stink bugs), were monitored periodically by sweep net, modified sweep net, or ground cloth at randomly selected locations within the test block, and assessed to determine whether they reached or were approaching economic injury levels At trial maturity, the entire length of rows 2 and 3 of each plot were harvested, and both total weight and percent moisture for each plot was recorded. During harvest, significant gaps (plants not touching each other) in harvested rows were noted and the total length of these gaps was recorded. Yields were calculated after correcting seed weight to 13% moisture. Larval incidence, defoliation, and yield data were subjected to ANOVA to determine significant sources of variability among line and replicate for each location at the 0.05 probability level (P). Significant differences among means were determined using the Tukey-Kramer test (Kramer 1956) at P=0.05.

In open field trials conducted at field trial site 1, defoliating caterpillars were first encountered at the R3 stage of growth, and increased to moderately damaging levels by the R6 stage of growth. Species encountered included *A. gemmatalis* (98%), *R. nu* (2%) and *Spodoptera* spp. (1%). Replicate was not a significant source of variability in larval incidence (F=0.0435; df=2, 57; P=0.9575), defoliation (F=0.0807; df=2, 57; P=0.9226) or yield (F=0.0213; df=2, 57; P=0.979), but event was highly significant for all three (larval incidence: F=69.6956; df=19, 38; P<0.0001; defoliation: F=25.9918; df=19, 40; P<0.0001; yield: F=3.357; df=19, 38; P=0.0007). Cumulative larval incidence (Table 9) reached 139-189 larvae per m row in the negative checks, while virtually no larvae were encountered in any of the transgenic entries. Maximum defoliation (Table 9) averaged 21-27% in the negative checks and was absent in all transgenic entries. Yields (Table 9) were reduced in both negative checks relative to all transgenic entries, although variability in yield reduced the significance of these reductions.

Event MON87751 had a significantly lower incidence of defoliating lepidopteran larvae (season cumulative) and significantly lower percent defoliation (season maximum) when compared to non-transgenic controls.

TABLE 9

Incidence of defoliating lepidopteran larvae (season cumulative) and defoliation (season maximum) of events generated with construct 1, 2, or 3 in naturally-infested open field efficacy trial conducted at field trial site 1.

| Transformation Construct | GOI | Event | Larvae/m row (season cumulative) | | % Defoliation (season maximum) | | Yield (kg/ha) | |
|---|---|---|---|---|---|---|---|---|
| | Cry1Ac | GM_A19459 | 2.2 ± 0.3 | c | 0 ± 0 | B | 2194 ± 89 | a |
| Construct 1 | Cry2Ab + Cry1A.105 | 2 | 0.8 ± 0.2 | c | 0 ± 0 | B | 2130 ± 28 | a |
| | | 3 | 0.8 ± 0.2 | c | 0 ± 0 | B | 1855 ± 240 | abc |
| | | 4 | 0.3 ± 0.0 | c | 0 ± 0 | B | 1643 ± 105 | abc |
| | | MON87751 | 0.3 ± 0.3 | c | 0 ± 0 | B | 1970 ± 126 | ab |
| | | 7 | 0.8 ± 0.2 | c | 0 ± 0 | B | 1552 ± 218 | abc |
| | | 8 | 2.0 ± 0.3 | c | 0 ± 0 | B | 2039 ± 138 | ab |
| | | 9 | 1.7 ± 0.8 | c | 0 ± 0 | B | 1628 ± 155 | abc |
| | | 10 | 0.5 ± 0.4 | c | 0 ± 0 | B | 1653 ± 247 | abc |
| | | 11 | 0.1 ± 0.1 | c | 0 ± 0 | B | 1957 ± 44 | ab |
| | | 14 | 1.6 ± 0.9 | c | 0 ± 0 | B | 1990 ± 65 | ab |
| | | 18 | 0.5 ± 0.3 | c | 0 ± 0 | B | 1885 ± 91 | ab |
| | | 19 | 1.5 ± 0.9 | c | 0 ± 0 | B | 1839 ± 55 | abc |
| Construct 2 | Cry2Ab | 20 | 2.0 ± 0.6 | c | 0 ± 0 | B | 1993 ± 64 | ab |
| | | 22 | 1.3 ± 0.7 | c | 0 ± 0 | B | 1957 ± 31 | ab |
| Construct 3 | Cry1A.105 | 29 | 0.8 ± 0.5 | c | 0 ± 0 | B | 1841 ± 124 | abc |
| | | 30 | 0.8 ± 0.4 | c | 0 ± 0 | B | 1833 ± 69 | abc |
| | | 31 | 0.4 ± 0.2 | c | 0 ± 0 | B | 1439 ± 357 | abc |
| | Negative | A3555 | 138.6 ± 10.2 | b | 27.2 ± 1.7 | A | 1288 ± 31 | bc |
| | | A5547 | 188.9 ± 25.1 | a | 21.0 ± 6.3 | A | 731 ± n/a | c |

Within columns means followed by the same letter are not significantly different (Tukey-Kramer means test at P < 0.05).

At another open field trial, conducted at field trial site 2, defoliating caterpillars were first encountered at the late vegetative stage of growth, and increased to highly damaging levels by the R3 stage of growth. Species encountered included *A. gemmatalis* (53%), "loopers" (probably *C. includens*, but *R. nu* possible) (44%) and *Spodoptera* spp. (3%). Replicate was not a significant source of variability in larval incidence (F=0.0085; df=2, 57; P=0.9915) or defoliation (F=0.0027; df=2, 57; P=0.9973), while event was highly significant for both (larval incidence: F=19.644; df=19, 40; P<0.0001; defoliation: F=671.3147; df=19, 40; P<0.0001). Cumulative larval incidence (Table 10) reached 43-50 larvae per m row in the negative checks, while negligible numbers were encountered in the transgenic entries. Maximum defoliation (Table 10) averaged 87-90% in the negative checks, while no more than trace levels were observed in all transgenic entries.

Event MON87751 had a significantly lower incidence of incidence of defoliating lepidopteran larvae (season cumulative), and a significantly lower percent defoliation (season maximum), when compared to non-transgenic controls.

TABLE 10

Incidence of defoliating lepidopteran larvae (season cumulative) and defoliation (season maximum) of events generated with construct 1, 2, or 3 in a naturally-infested open field efficacy trial conducted at field trial site 2.

| Transformation Construct | GOI | Event | Larvae/m row (season cumulative) | | % Defoliation (season maximum) | |
|---|---|---|---|---|---|---|
| | Cry1Ac | GM_A19459 | 1.9 ± 0.4 | b | 0 ± 0 | b |
| Construct 1 | Cry2Ab + Cry1A.105 | 2 | 1.3 ± 0.2 | b | 0 ± 0 | b |
| | | 3 | 2.3 ± 0.6 | b | 0 ± 0 | b |
| | | 4 | 3.1 ± 0.4 | b | 0 ± 0 | b |
| | | MON87751 | 1.6 ± 0.3 | b | 0 ± 0 | b |
| | | 7 | 1.7 ± 0.5 | b | 0 ± 0 | b |
| | | 8 | 2.3 ± 1.6 | b | 0 ± 0 | b |
| | | 9 | 2.0 ± 0.7 | b | 1.7 ± 1.7 | b |
| | | 10 | 2.1 ± 1.0 | b | 0 ± 0 | b |
| | | 11 | 3.3 ± 1.0 | b | 0 ± 0 | b |
| | | 14 | 1.1 ± 0.2 | b | 0 ± 0 | b |
| | | 18 | 2.8 ± 0.6 | b | 0 ± 0 | b |
| | | 19 | 3.1 ± 0.8 | b | 0 ± 0 | b |
| Construct 1 | Cry2Ab | 20 | 2.9 ± 1.3 | b | 0 ± 0 | b |
| | | 22 | 2.4 ± 0.9 | b | 0 ± 0 | b |
| Construct 3 | Cry1A.105 | 29 | 1.5 ± 0.1 | b | 2.0 ± 2.0 | b |
| | | 30 | 2.4 ± 0.9 | b | 2.0 ± 2.0 | b |
| | | 31 | 1.8 ± 0.7 | b | 0 ± 0 | b |
| | Negative | A3555 | 42.9 ± 10.4 | a | 86.7 ± 3.3 | a |
| | | A5547 | 49.9 ± 8.4 | a | 90.0 ± 0.0 | a |

Within columns means followed by the same letter are not significantly different (Tukey-Kramer means test at P < 0.05).

In another open field trial, conducted at field trial site 3, replicate was not a significant source of variability in total ($F=0.312$; $df=2, 24$; $P=0.7349$) or damaged ($F=0.0438$; $df=2, 24$; $P=0.9572$) pods per plant or yield ($F=0.2221$; $df=2, 24$; $P=0.8025$). Event, however, was a significant source of variability in total ($F=4.3643$; $df=8, 18$; $P=0.0045$) and damaged ($F=34.5288$; $df=8, 18$; $P<0.0001$) pods per plant, though not yield ($F=0.6237$, $df=8, 18$, $P=0.7475$). Negative checks averaged 25.0-26.0 pods per plant with 30.8-31.0% of pods damaged, while test events, including event MON87751, averaged 28.9-38.9 pods per plant with <2% of pods damaged (Table 11). The reduced number of pods per plant in the negative checks is likely a result of premature pod abscission caused by podworm damage, as numerous damaged pods were observed lying on the ground beneath the plants in the negative checks (but not the test events) (Table 11).

TABLE 11

Total and damaged pods per plant in podworm-infested open field efficacy trial, conducted at field trial site 3, evaluating events generated with construct 1, 2, or 3.

| Transformation Construct | Event | GOI | Total pods/plant | Damaged pods/plant |
|---|---|---|---|---|
| Construct 1 | MON87751 | Cry2Ab + Cry1A.105 | 38.9 ± 2.9  A | 1.0 ± 0.4  B |
|  | 8 |  | 37.4 ± 4.1  AB | 1.4 ± 0.4  B |
|  | 10 |  | 37.2 ± 1.9  AB | 0.9 ± 0.5  B |
| Construct 2 | 20 | Cry2Ab | 38.6 ± 1.0  A | 0.8 ± 0.5  B |
| Construct 3 | 29 | Cry1A.105 | 35.1 ± 2.7  AB | 0.6 ± 0.2  B |
| NEG | 40-3-2 |  | 25.0 ± 4.0  AB | 30.8 ± 1.3  A |
|  | A3555 |  | 26.0 ± 0.1  B | 31.0 ± 6.5  A |

Means (±S.E.) within columns followed by the same letter are not significantly different (Tukey-Kramer means test, $P < 0.05$).

In open field trials conducted at field trial site 4, defoliating caterpillars were encountered at the R3 stage of growth, and increased to highly damaging levels by the R6-R7 stage of growth. Species encountered included *A. gemmatalis* (77%), *Plathypena scabra* (green cloverworm) (17%), and *C. includens* (6%). Replicate was not a significant source of variability in larval incidence ($F=0.0219$; $df=2, 69$; $P=0.9783$), defoliation ($F=0.0007$; $df=2, 69$; $P=0.9993$), or yield ($F=1.1477$; $df=2, 69$; $P=0.3233$). Event was significant, to highly significant, for all three (larval incidence: $F=96.9673$; $df=23, 48$; $P<0.0001$; defoliation: $F=363.8854$; $df=23, 48$; $P<0.0001$; yield: $F=1.7814$; $df=23, 48$; $P=0.046$). Cumulative larval incidence (Table 12) reached 117-123 larvae per m row in the negative checks, while virtually no larvae were encountered in any of the transgenic entries. Maximum defoliation (Table 12) averaged 68-83% in the negative checks and was absent in all transgenic entries, including event MON87751.

TABLE 12

Incidence of defoliating lepidopteran larvae (season cumulative) and % defoliation (season maximum) from events generated with construct 1, 2, or 3 in a naturally-infested open field trial conducted at field trial site 4.

| Transformation Construct | GOI | Event | Larvae/m row (season cumulative) | % Defoliation (season maximum) |
|---|---|---|---|---|
|  | Cry1Ac | GM_A19478 | 0.7 ± 0.7  b | 0 ± 0  c |
| Construct 1 | Cry2Ab + Cry1A.105 | 2 | 0.7 ± 0.7  b | 0 ± 0  c |
|  |  | 3 | 0 ± 0  b | 0 ± 0  c |
|  |  | 4 | 0.7 ± 0.7  b | 0 ± 0  c |
|  |  | MON87751 | 0 ± 0  b | 0 ± 0  c |
|  |  | 8 | 1.7 ± 0.9  b | 0 ± 0  c |
|  |  | 9 | 1.3 ± 1.3  b | 0 ± 0  c |
|  |  | 10 | 0 ± 0  b | 0 ± 0  c |
|  |  | 11 | 1.0 ± 0.0  b | 0 ± 0  c |
|  |  | 14 | 0.7 ± 0.7  b | 0 ± 0  c |
|  |  | 18 | 0 ± 0  b | 0 ± 0  c |
|  |  | 19 | 1.3 ± 1.3  b | 0 ± 0  c |
| Construct 2 | Cry2Ab | 20 | 2.0 ± 2.0  b | 0 ± 0  c |
|  |  | 22 | 0.7 ± 0.7  b | 0 ± 0  c |
| Construct 3 | Cry1A.105 | 31 | 1.0 ± 0.6  b | 0 ± 0  c |
|  |  | 29 | 0.7 ± 0.7  b | 0 ± 0  c |
|  | Negative | A3555 | 122.7 ± 16.2  a | 83.3 ± 3.3  a |
|  |  | A5547 | 117.0 ± 2.1  a | 68.3 ± 4.4  b |

Within columns means followed by the same letter are not significantly different (Tukey-Kramer means test at $P < 0.05$).

At another open field trial conducted at field trial site 5, defoliating caterpillars were first encountered at the R2 stage of growth, and increased to highly damaging levels during the R5-R6 stage of growth. Species encountered included *A. gemmatalis* (93%), *C. includens* (5%), and *Spodoptera ornithogalli* (2%). Replicate was not a significant source of variability in larval incidence (F=0.0206; df=2, 69; P=0.9796), defoliation (F=0.0054; df=2, 69; P=0.9946), or yield (F=0.2379; df=2, 69; P=0.7889). Event was highly significant for all three (larval incidence: F=122.46; df=23, 48; P<0.0001; defoliation: F=623.0217; df=23, 48; P<0.0001; yield: F=2.9366; df=23, 48; P=0.0008). Cumulative larval incidence (Table 13) reached 76-137 larvae per m row in the negative checks, while virtually no larvae were encountered in any of the transgenic entries. Maximum defoliation (Table 13) averaged 82-88% in the negative checks and was absent in all transgenic entries, including event MON87751.

TABLE 13

Incidence of defoliating lepidopteran larvae (season cumulative) and defoliation (season maximum), from events generated with construct 1, 2, or 3 in a naturally-infested open field trial conducted at field trial site 5.

| Transformation Construct | GOI | Event | Larvae/m row (season cumulative) | | % Defoliation (season maximum) | |
|---|---|---|---|---|---|---|
| | Cry1Ac | GM_A19478 | 1.0 ± 0.6 | c | 0 ± 0 | c |
| Construct 1 | Cry2Ab + Cry1A.105 | 2 | 1.0 ± 1.0 | c | 0 ± 0 | c |
| | | 3 | 1.7 ± 0.3 | c | 0 ± 0 | c |
| | | 4 | 1.0 ± 0.6 | c | 0 ± 0 | c |
| | | MON87751 | 1.0 ± 0.6 | c | 0 ± 0 | c |
| | | 8 | 1.0 ± 0.6 | c | 0 ± 0 | c |
| | | 9 | 1.7 ± 0.3 | c | 0 ± 0 | c |
| | | 10 | 0.7 ± 0.7 | c | 0 ± 0 | c |
| | | 11 | 1.3 ± 0.9 | c | 0 ± 0 | c |
| | | 14 | 2.0 ± 1.2 | c | 0 ± 0 | c |
| | | 18 | 1.0 ± 1.0 | c | 0 ± 0 | c |
| | | 19 | 0.3 ± 0.3 | c | 0 ± 0 | c |
| Construct 2 | Cry2Ab | 20 | 2.3 ± 1.3 | c | 0 ± 0 | c |
| | | 22 | 0.3 ± 0.3 | c | 0 ± 0 | c |
| Construct 3 | Cry1A.105 | 31 | 1.3 ± 0.3 | c | 0 ± 0 | c |
| | | 29 | 1.3 ± 0.3 | c | 0 ± 0 | c |
| | Negative | A3555 | 76.0 ± 7.0 | b | 81.7 ± 4.4 | b |
| | | A5547 | 137.0 ± 10.6 | a | 88.3 ± 1.7 | a |

Within columns means followed by the same letter are not significantly different (Tukey-Kramer means test at P < 0.05).

At another open field trial, conducted at field trial site 6, defoliating caterpillars (primarily *H. zea* and *C. includens*) were encountered during the R6 stages of growth but never reached highly significant numbers. However, substantial damage to plants by *E. lignosellus* in borders, buffers, and negative checks occurred earlier in the season, resulting in wilted, dying, and dead plants by the R5-R6 stage of growth, at which time damage data were recorded. Replicate was not a significant source of plants damaged by *E. lignosellus* (F=0.3431; df=2, 69; P=0.71). Event was highly significant for plants damaged by *E. lignosellus*: F=16.7555; df=23, 48; P<0.0001). The percent of plants damaged by *E. lignosellus* (Table 14) averaged 10-28% in the negative checks, while no plants in any of the transgenic entries exhibited damage, including event MON87751.

TABLE 14

Incidence of defoliating damage by *E. lignosellus* (LCSB-naturally-infested open field efficacy trial, conducted at field trial site 6, evaluating events generated with construct 1, 2, or 3.

| Transformation Construct | GOI | Event | # *E. lignosellus* damaged plants | |
|---|---|---|---|---|
| | Cry1Ac | GM_A19478 | 0 ± 0 | c |
| Construct 1 | Cry2Ab + Cry1A.105 | 2 | 0 ± 0 | c |
| | | 3 | 0 ± 0 | c |
| | | 4 | 0 ± 0 | c |
| | | MON87751 | 0 ± 0 | c |
| | | 8 | 0 ± 0 | c |
| | | 9 | 0 ± 0 | c |
| | | 10 | 0 ± 0 | c |
| | | 11 | 0 ± 0 | c |
| | | 14 | 0 ± 0 | c |
| | | 18 | 0 ± 0 | c |
| | | 19 | 0 ± 0 | c |
| Construct 2 | Cry2Ab | 20 | 0 ± 0 | c |
| | | 22 | 0 ± 0 | c |
| Construct 3 | Cry1A.105 | 31 | 0 ± 0 | c |
| | | 29 | 0 ± 0 | c |
| | Negative | A3555 | 10.3 ± 5.9 | b |
| | | A5547 | 28 ± 4 | a |

Within columns means followed by the same letter are not significantly different (Tukey-Kramer means test at $P < 0.05$).

At another open field trial, conducted at field trial site 7, defoliating caterpillars were first encountered at the R1-R2 stage of growth and increased to highly damaging levels by the R4-R6 stage of growth. Species encountered included *C. includens* (54%), *Spodoptera exigua* (43%), and *Estigmene acrea* (2%). Replicate was not a significant source of variability in larval incidence (F=0.0866; df=2, 69; P=0.9172), or defoliation (F=0.1129; df=2, 69; P=0.8934). Event was highly significant for both (larval incidence: F=69.918; df=23, 48; P<0.0001; defoliation: F=21.6603; df=23, 48; P<0.0001). Cumulative larval incidence (Table 15) reached 152-166 larvae per m row in the negative checks, while virtually no larvae were encountered in the Cry1Ac positive control, or events generated with constructs 1, 2, or 3 expressing Cry2Ab and/or Cry1A.105. Maximum defoliation (Table 15) averaged 24% in the negative checks but did not exceed trace levels in events generated with constructs 1, 2, or 3 expressing Cry2Ab and/or Cry1A.105, including event MON87751 or the Cry1Ac positive control.

TABLE 15

Incidence of defoliating lepidopteran larvae (season cumulative), defoliation (season maximum), and yield from events generated with construct 1, 2, or 3 in naturally-infested open field trial, conducted at field trial site 7.

| Transformation Construct | GOI | Event | Larvae/m row (season cumulative) | | % Defoliation (season maximum) | |
|---|---|---|---|---|---|---|
| | Cry1Ac | GM_A19478 | 6.0 ± 1.5 | d | 0.7 ± 0.7 | c |
| Construct 1 | Cry2Ab + Cry1A.105 | 2 | 2.5 ± 1.2 | d | 0 ± 0 | c |
| | | 3 | 3.6 ± 1.3 | d | 0 ± 0 | c |
| | | 4 | 3.2 ± 1.3 | d | 0.3 ± 0.3 | c |
| | | MON87751 | 3.5 ± 1.5 | d | 0 ± 0 | c |
| | | 8 | 3.9 ± 0.8 | d | 0 ± 0 | c |
| | | 9 | 3.0 ± 0.6 | d | 0 ± 0 | c |
| | | 10 | 2.3 ± 0.5 | d | 0 ± 0 | c |
| | | 11 | 3.0 ± 0.4 | d | 0 ± 0 | c |
| | | 14 | 2.7 ± 0.9 | d | 0 ± 0 | c |
| | | 18 | 4.3 ± 0.8 | d | 0.3 ± 0.3 | c |
| | | 19 | 4.3 ± 0.6 | d | 0 ± 0 | c |
| Construct 2 | Cry2Ab | 20 | 7.0 ± 1.4 | d | 0 ± 0 | c |
| | | 22 | 4.5 ± 0.7 | d | 0.3 ± 0.3 | c |
| Construct 3 | Cry1A.105 | 31 | 3.3 ± 0.9 | d | 0 ± 0 | c |
| | | 29 | 5.0 ± 1.9 | d | 0 ± 0 | c |
| | Negative | A3555 | 152.0 ± 14.6 | a | 24.0 ± 1.0 | a |
| | | A5547 | 165.8 ± 11.6 | a | 24.0 ± 1.0 | a |

Within columns means followed by the same letter are not significantly different (Tukey-Kramer means test at $P < 0.05$).

At another open field trial, conducted at field trial site 8, moderate pressure by the defoliating caterpillars *C. includens* (41%), *A. gemmatalis* (38%), *S. frugiperda* (13%) and *S. ornithogalli* (8%) occurred during the R4-R6 stages of growth. Replicate was not a significant source of variability in larval incidence (F=0.0924; df=3, 52; P=0.9639), or defoliation (F=0.372; df=3, 52; P=0.7735). Event was a significant source of variability in larval incidence (F=40.008, df=13, 42, P<0.0001) and defoliation (F=11.9356, df=13, 42, P<0.0001). Cumulative larval incidence and maximum defoliation averaged 9.1-13.9 larvae per m row and 31-35% (the latter moderately above economic threshold), respectively, in the negative checks but did not exceed trace in the positive control and all test events, including event MON87751 (Table 16). No significant occurrence of non-target pests in the trial was noted.

TABLE 16

Cumulative incidence of defoliating lepidopteran larvae, maximum percent defoliation and yield in naturally-infested open field efficacy trial conducted at field trial site 8.

| Transformation Construct | Event | GOI | Cumulative larvae/m row | | Maximum % defoliation | |
|---|---|---|---|---|---|---|
| POS | GM_A19478 | Cry1Ac | 0.5 ± 0.2 | C | 0 ± 0 | B |
| Construct 1 | MON87751 | Cry2Ab + Cry1A.105 | 0.3 ± 0.2 | C | 0 ± 0 | B |
| | 8 | | 0.3 ± 0.2 | C | 0 ± 0 | B |
| | 10 | | 0.7 ± 0.4 | C | 0.5 ± 0.5 | B |
| Construct 2 | 20 | Cry2Ab | 0.7 ± 0.5 | C | 5.0 ± 5.0 | B |
| Construct 3 | 29 | Cry1A.105 | 1.3 ± 0.8 | C | 5.0 ± 5.0 | B |
| Construct 4 | 32 | Cry2Ab + Cry1A.105 | 1.4 ± 0.7 | C | 0.3 ± 0.3 | B |
| | 40 | | 0.6 ± 0.1 | C | 0.3 ± 0.3 | B |
| Construct 5 | 46 | Cry2Ab | 0.5 ± 0.1 | C | 0.3 ± 0.3 | B |
| Construct 6 | 42 | Cry1A.105 | 1.0 ± 0.4 | C | 0.3 ± 0.3 | B |
| NEG | A3555 | Negative | 9.1 ± 0.5 | B | 35.0 ± 9.6 | A |
| | A5547 | | 13.9 ± 1.0 | A | 31.3 ± 4.3 | A |

Within columns means (±S.E.) followed by the same letter are not significantly different (Tukey-Kramer means test at $P < 0.05$).

During a second season of open field trials conducted at field trial site 6, very heavy pressure by *H. zea* occurred during the R3-R5 stages of growth. Replicate was not a significant source of variability in damaged pods (F=0.0280; df=3, 52; P=0.9936). Event was a significant source of variability in damaged pods (F=15.4758, df=13, 42, P<0.0001). Negative checks averaged 64-78% damaged pods, while virtually no damage occurred in any of the test events, including event MON87751 (Table 17).

TABLE 17

Cumulative incidence of defoliating lepidopteran larvae, maximum percent defoliation, pod production, percent of pods damaged by heliothine larvae and yield in naturally-infested open field efficacy trial conducted during a second season at field trial site 6.

| Transformation Construct | Event | GOI | % Pods damaged | |
|---|---|---|---|---|
| POS | GM_A19478 | Cry1Ac | 0.1 ± 0.1 | C |
| Construct 1 | MON87751 | Cry2Ab + Cry1A.105 | 0.1 ± 0.1 | C |
| | 8 | | 0.1 ± 0.1 | C |
| | 10 | | 0.7 ± 0.4 | C |
| Construct 2 | 20 | Cry2Ab | 0 ± 0 | C |
| Construct 3 | 29 | Cry1A.105 | 0 ± 0 | C |
| Construct 4 | 32 | Cry2Ab + Cry1A.105 | 0.1 ± 0.1 | C |
| | 40 | | 0.5 ± 0.2 | C |
| Construct 5 | 46 | Cry2Ab | 0.6 ± 0.4 | C |
| Construct 6 | 42 | Cry1A.105 | 0.6 ± 0.5 | C |
| NEG | A3555 | Negative | 63.8 ± 4.4 | B |
| | A5547 | | 78.0 ± 8.8 | A |

Within columns means followed by the same letter are not significantly different (Tukey-Kramer means test at P < 0.05).

The results of the multiple open field trials described in this example, combined with the results of the multiple screenhouse trials (described in Example 3) further confirm effective, season-long suppression of larval populations of all lepidopteran soybean pests encountered by transgenic soybean events generated by constructs 1, 2 or 3 across five plant generations (R2 through R7), suggesting stable transgene expression within and across generations.

The combined results demonstrate that, under conditions of above-threshold pressure by all four primary target pests (*Anticarsia gemmatalis* and *Chrysodeixis includens* in one geographic location, and the same target pests plus *Rachiplusia nu* and *Crocidosema aporema* in a second geographic location), efficacy by transgenic events generated with constructs 1, 2 or 3, including event MON87751, was equivalent to a transgenic event expressing Cry1Ac and previously demonstrated to control lepidopteran insect pests of soybean. The events generated with constructs 2 or 3 and expressing only Cry2Ab protein or only Cry1A.105 protein, respectively, also demonstrated equivalent efficacy to the transgenic event expressing Cry1Ac protein, suggesting that expression of both Cry2Ab and Cry1A.105 proteins in event MON87751 will have improved durability over the Cry1Ac transgenic event through improved insect resistance management.

Equivalent efficacy among the events generated with construct 1, including event MON87751, has also been demonstrated against numerous secondary target pests, including three species of armyworm (*Spodoptera exigua*, *S. frugiperda* and *S. eridania*), two heliothine podworms (*Helicoverpa zea* and *H. gelotopeon*), one stalkboring insect (*Elasmopalpus lignosellus*) and one defoliator (*Plathypena scabra*).

EXAMPLE 5

This example describes the molecular characterization of event MON87751, which included protein expression and extensive molecular characterization. This molecular characterization was completed concurrently on events which were being tested in agronomic field trials, efficacy screenhouse trials, and efficacy field trials.

For molecular characterization of event MON87751, copy number of the transgene insert sequence (comprising both Cry2Ab and Cry1A.105 cassettes, SEQ ID NO:9) was determined using a combination of Southern analysis and endpoint TAQMAN® assay. The molecular analysis confirmed that there was only a single insert (T-DNA expression cassette containing expression cassettes for both Cry2Ab and Cry1A.105 proteins, and represented by SEQ ID NO:9) with no detection of the vector backbone, and no detection of the T-DNA cassette containing the selection/scorable marker sequences. The full sequence of the single insert (SEQ ID NO:9) in event MON87751 genomic DNA confirmed that the sequence was identical to the sequence of the transformation construct.

Figure 3:
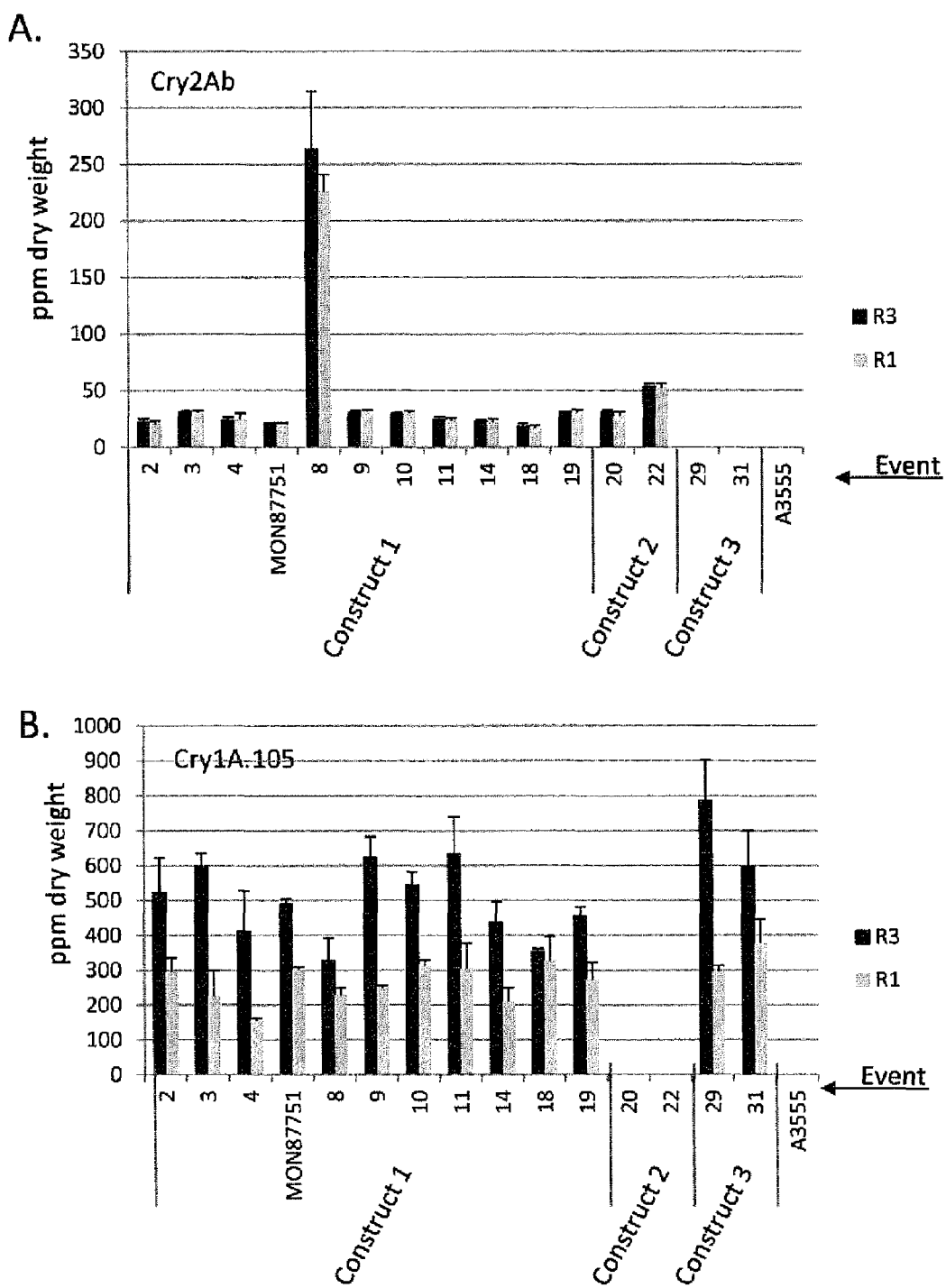
FIG. 3 is a graphical representation of the results of ELISA analysis of Cry protein expression in events generated with construct 1, construct 2, and construct 3, compared to a non-transgenic soybean line (A3555). Panel A. shows Cry2Ab protein levels in leaf tissue collected at R1 and R3 stage of plant growth. Panel B. shows Cry1A.105 protein levels in leaf tissue collected at R1 and R3 stage of plant growth.

For protein expression, leaf samples were collected from plants homozygous for event MON87751 allele and extracts prepared from lyophilized samples, ELISAs were conducted per standard protocols measuring protein level of Cry2Ab or Cry1A.105 with antibodies specific for Cry2Ab or Cry1A.105, respectively, and results were expressed as parts per million (ppm) of dry weight. Leaf samples were collected at the R1 and R3 stage of plant growth for events generated by transformation with constructs 1, 2 or 3 and the non-transgenic control A3555. ELISA results indicated that Cry2Ab levels for events generated from construct 1 and construct 2 ranged from about 20 ppm to about 50 ppm dry weight, with the exception of event 8 (which was determined to have a linked viral promoter, but no other sequence, from the selectable/scorable marker T-DNA, and event 8 was not further evaluated), and no Cry2Ab expression from the events generated with construct 3 (expressing Cry1A.105 only) or the non-transgenic control (FIG. 3A). Further the Cry2Ab protein expression levels were approximately equal for both R1 and R3 growth stages. ELISA results indicated that Cry1A.105 levels for events generated from construct 1 and construct 3 ranged from about 150 ppm to about 800 ppm dry weight, and no Cry1A.105 expression from either the events generated with construct 2 (expressing Cry2Ab only) or the non-transgenic control (FIG. 3B). Further the Cry1A.105 protein expression levels ranged higher for leaf samples at the R3 growth stage compared to the R1 growth stage.

Figure 4:
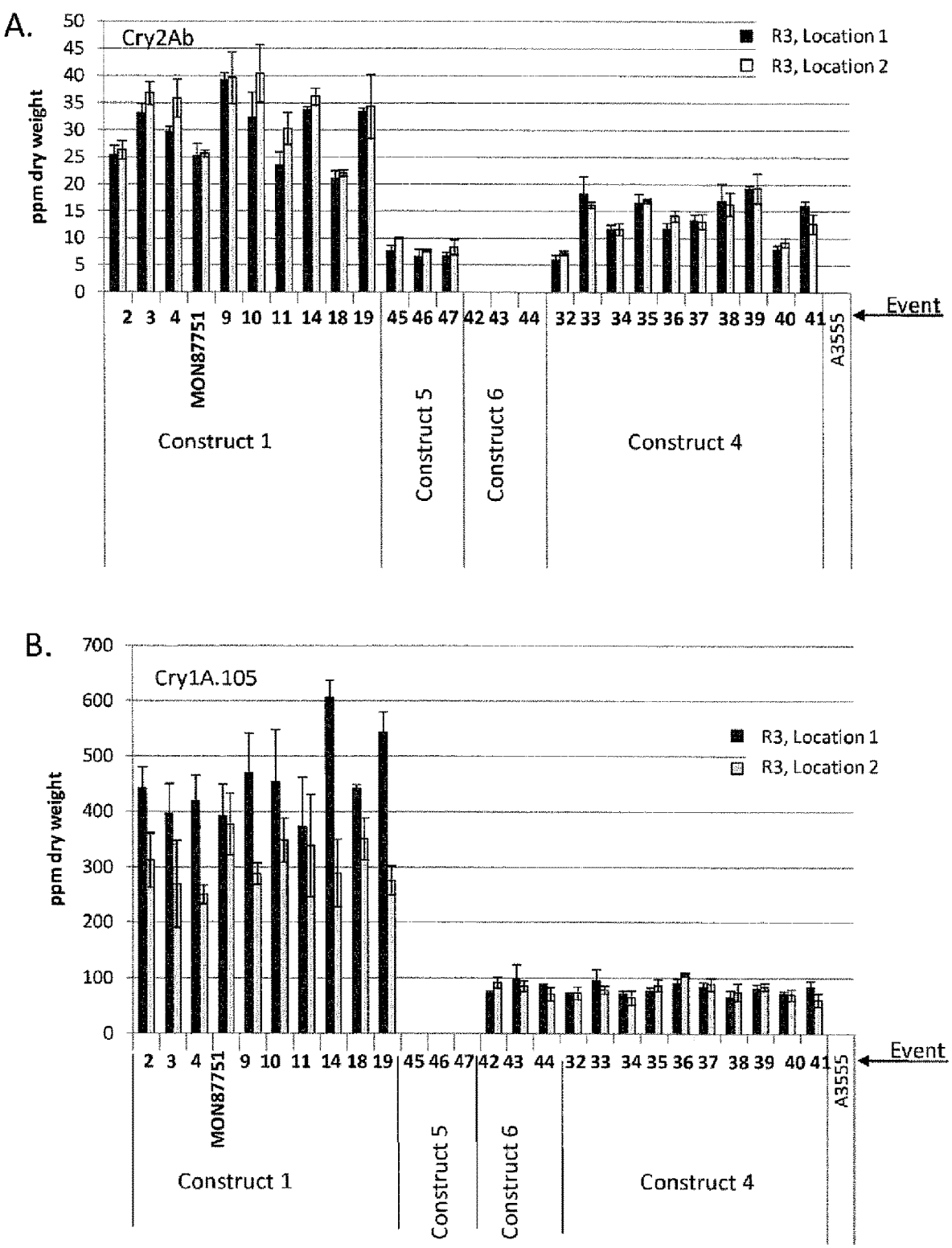
FIG. 4 is a graphical representation of the results of ELISA analysis of Cry protein expression in events generated with construct 1, construct 5, construct 6, and construct 4, compared to a non-transgenic soybean line (A3555). Panel A. shows Cry2Ab protein levels in leaf tissue collected at the R3 stage of plant growth from plants grown in two separate screenhouse trials. Panel B. shows Cry1A.105 protein levels in leaf tissue collected at the R3 stage of plant growth from plants grown in two separate screenhouse trials.

Additional ELISA results show that Cry2Ab protein levels from events generated with construct 1 were higher relative to events generated with either construct 5 or construct 4, and as expected, there was no Cry2Ab detected for either the non-transgenic control or the events generated with construct 6 (expressing Cry1A.105 only) (FIG. 4A). In the same set of leaf samples, ELISA results show that there is a two-fold or higher level of expression of Cry1A.105, for events generated with construct 1, with an approximate four-fold higher expression for MON87751, when compared to events generated with either construct 6 or construct 4, and as expected, there was no Cry1A.105 expression detected for either the non-transgenic control or the events generated with construct 5 (expressing Cry2Ab only) (FIG. 4B). For these ELISAs, leaf samples were collected from the R3 stage of growth from plants grown at each of two separate efficacy screenhouse trial locations.

Further ELISA results show that Cry2Ab protein levels in extracts from an event generated with construct 1, and an event generated with construct 2 were a) higher relative to events generated with either construct 4, construct 5, or construct 7; b) approximately the same or somewhat lower relative to events generated with either construct 9, or construct 11; and c) as expected, there was no Cry2Ab detected for either the non-transgenic control (not shown) or the events generated with either construct 3 or construct 6 (expressing Cry1A.105 only) (FIG. 5). For these ELISAs, leaf samples were collected at the R3 and R5 stage of growth, and the Cry2Ab levels were higher at the R5 growth stage for events generated with construct 1 and construct 2, and the Cry2Ab levels were higher in events generated with construct 9, and construct 11 (FIG. 5). In the same set of leaf samples, ELISA results show that Cry1A.105 protein levels in extracts from events generated with construct 1 and construct 3 were significantly higher relative to events generated with construct 4, construct 6, construct 9 or construct 7, and, as expected, there was no Cry1A.105 detected for either the non-transgenic control (not shown) or the events generated with either construct 2 or construct 5 (expressing Cry2Ab only) (FIG. 6). For these ELISAs, leaf samples were collected at the R3 and R5 stage of growth, and the Cry1A.105 levels were orders of magnitude higher at the R5 growth stage for events generated with construct 1 and construct 3, compared to events generated with construct 4, construct 6, construct 9 or construct 7, see FIG. 6A Y-axis plotted at 0-5000 ppm dry weight and FIG. 6B Y-axis plotted at 0-500 ppm dry weight. The ELISA data indicate that there is higher expression of both Cry2Ab and Cry1A.105 in events generated with construct 1 compared to events generated with construct 4, construct 7 or construct 9, all containing two Cry protein expression cassettes—one expression cassette encoding Cry2Ab and one expression cassette encoding Cry1A.105. Additionally, it was noted that the relatively high protein expression in events generated with construct 1 (including event MON87751), construct 2, and construct 3, was stable over at least 4 generations of soybean (R0, R1, R2, and R3), and the Cry1A.105 protein level increased in leaf tissue collected from homozygous events at the R3 to R5 stage of growth.

EXAMPLE 6

This example describes methods useful in identifying the presence of event MON87751 DNA in a soybean sample. A pair of PCR primers and a probe were designed for the purpose of identifying the unique junction formed between the genomic DNA and the arbitrarily assigned 3' end of the inserted DNA of event MON87751 (i.e., the 3' junction) and encompassed in SEQ ID NO:10, SEQ ID NO: 8, SEQ ID NO:2, SEQ ID NO:4, or SEQ ID NO:6.

The sequence of the oligonucleotide forward primer SQ20267 (SEQ ID NO:11) is identical to the nucleotide sequence corresponding to positions 11400 through 11426 of SEQ ID NO:10, and positions 212 through 238 of SEQ ID NO:8, and positions 10066 through 10092 of SEQ ID NO:9. The sequence of the oligonucleotide reverse primer SQ25826 (SEQ ID NO:12) is identical to the reverse compliment of the nucleotide sequence corresponding to positions 11454 through 11479 of SEQ ID NO:10, and positions 266 through 291 of SEQ ID NO:8, and positions 51 through 76 of SEQ ID NO:6, and positions 31 through 56 of SEQ ID NO:4. The sequence of the oligonucleotide probe PB10263 (SEQ ID NO:13) is identical to the nucleotide sequence corresponding to positions 11428 through 11446 of SEQ ID NO:10, and positions 10094 through 10112 of SEQ ID NO:9, and positions 240 through 258 of SEQ ID NO:8, and positions 25 through 43 of SEQ ID NO:6, and positions 5 through 23 of SEQ ID NO:4. The PCR primers SQ20267 (SEQ ID NO:11) and SQ25826 (SEQ ID NO:12) amplify an 80 nucleotide amplicon of the unique the genomic/insert DNA at the right junction of event MON87751. This same primer pair with probe PB10263 (SEQ ID NO:13), which may be fluorescently labeled (e.g., a 6FAM™ fluorescent label), can be used in an Endpoint TaqMan® PCR assay to identify the presence of DNA derived from event MON87751 in a sample.

In addition to SQ20267 (SEQ ID NO:11), SQ25826 (SEQ ID NO:12) and PB10263 (SEQ ID NO:13), it should be apparent to persons skilled in the art that other primers and/or probes can be designed to either amplify and/or hybridize to sequences within SEQ ID NO:10 which are unique to, and useful for, detecting the presence of DNA derived from event MON87751 in a sample.

Following standard molecular biology laboratory practices, PCR assays for event identification were developed for detection event MON87751 DNA in a sample. Parameters of either a standard PCR assay or a TaqMan® PCR assay were optimized with each set of primer pairs and probes (i.e. probes labeled with a fluorescent tag such as 6FAM™) used to detect the presence of DNA derived from event MON87751 in a sample SQ20267 (SEQ ID NO:11), SQ25826 (SEQ ID NO:12) and PB10263 (SEQ ID NO:13). A control for the PCR reaction includes internal control primers and an internal control probe (e.g., VIC™—labeled), specific to a single copy gene in the soybean genome. One of skill in the art will know how to design primers specific to a single copy gene in the soybean genome. Generally, the parameters which were optimized for detection of event MON87751 DNA in a sample included primer and probe concentration, amount of template DNA, and PCR amplification cycling parameters. The template DNA samples and controls were as follows: [1] DNA extracted from either leaf sample or single seed sample to be analyzed; [2] negative control DNA (non-transgenic soybean DNA); [3] negative water control (no template); and [4] positive control MON87751 DNA. Other methods known to those skilled in the art that produce amplicons that identify the event MON87751 DNA in a sample is within the skill of the art.

A zygosity assay is useful for determining if a plant comprising an event is homozygous for the event DNA; that is comprising the exogenous DNA in the same location on each chromosome of a chromosomal pair; or heterozygous for an event DNA, that is comprising the exogenous DNA on only one chromosome of a chromosomal pair; or is null for the event DNA, that is wild-type. An endpoint TAQ-MAN® thermal amplification method was used to develop a zygosity assay for event MON87751. For this assay, three primers and two probes were mixed together with the sample for the assay. The three primers were SQ20267 (SEQ ID NO:11), which hybridizes and extends specifically from the 3' region of the inserted exogenous DNA; primer SQ27115 (SEQ ID NO:14), which hybridizes and extends specifically from the soybean genomic DNA flanking the 3' side of the inserted exogenous DNA; and primer SQ26901 (SEQ ID NO:15), which hybridizes and extends specifically from the soybean genomic DNA flanking the 5' side of the inserted exogenous DNA. Primers SQ20267 and SQ27115 and the probe PB10263 (SEQ ID NO:13) (6-FAM™—labeled) are diagnostic when there is a copy of the inserted exogenous DNA present in the template DNA, i.e., for event MON87751. Primers SQ26901 and SQ27115 and the probe PB11254 (SEQ ID NO:16) (VIC™—labeled) are diagnostic when there is no copy of the inserted exogenous DNA present in the genomic DNA, i.e. wild-type. When the three primers and two probes are mixed together in a PCR reaction with DNA extracted from a plant homozygous for event MON87751, there is a fluorescent signal only from 6-FAM™—labeled probe PB10263 which is indicative of and diagnostic for a plant homozygous for event MON87751. When the three primers and two probes are mixed together in a PCR reaction with DNA extracted from a plant heterozygous for event MON87751, there is a fluorescent signal from both the 6-FAM™—labeled probe PB10263 and the VIC™—labeled probe PB11254 which is indicative of and diagnostic for a plant heterozygous for event MON87751. When the three primers and two probes are mixed together in a PCR reaction with DNA extracted from a plant which is null for event MON87751 (i.e. wild-type), there is a fluorescent signal from only the VIC™—labeled probe PB11254 which is indicative of and diagnostic for a plant null for event MON87751, i.e. wild-type. The template DNA samples and controls were as follows: [1] DNA extracted from either leaf sample or single seed sample to be analyzed; [2] negative control DNA (non-transgenic DNA); [3] negative water control (no template); [4] positive control MON87751 genomic DNA from known heterozygous sample; and [5] positive control MON87751 genomic DNA from known homozygous sample.

EXAMPLE 7

The following example describes how one may identify the MON87751 event within progeny of any breeding activity using soybean event MON87751.

DNA event primer pairs are used to produce a PCR amplicon diagnostic for soybean event MON87751. An amplicon diagnostic for MON87751 comprises at least one junction sequence, provided as SEQ ID NO:1 or SEQ ID NO:2 or SEQ ID NO:3 or SEQ ID NO:4 or SEQ ID NO:5 or SEQ ID NO:6. Primer pairs that will produce a diagnostic amplicon for MON87751 include primer pairs based upon the flanking sequences and the inserted expression cassette (SEQ ID NO:9). To acquire a diagnostic amplicon in which SEQ ID NO:1 or SEQ ID NO:3 or SEQ ID NO:5 is found, one would design a forward primer molecule based upon SEQ ID NO:7 from bases 1 through 1334 and a reverse primer molecule based upon the inserted expression cassette DNA sequence (SEQ ID NO:9 from positions 1 through 10119) in which the primer molecules are of sufficient length of contiguous nucleotides to specifically hybridize to SEQ ID NO:7 and SEQ ID NO:9. To acquire a diagnostic amplicon in which SEQ ID NO:2 or SEQ ID NO:4 or SEQ ID NO:6 is found, one would design a forward primer molecule based upon the inserted expression cassette DNA sequence (SEQ ID NO:9 from positions 1 through 10119) and a reverse primer molecule based upon the 3' flanking sequence (SEQ ID NO:8 from position 266 through 1452), in which the primer molecules are of sufficient length of contiguous nucleotides to specifically hybridize to SEQ ID NO:8 and SEQ ID NO:9.

An example of the amplification conditions for this analysis is illustrated in Example 4. However, any modification of these methods or the use of DNA primers homologous or complementary to SEQ ID NO:7 or SEQ ID NO:8 or DNA sequences of the genetic elements contained in the transgene insert (SEQ ID NO:9) of MON87751 that produce an amplicon diagnostic for MON87751 is within the art. A diagnostic amplicon comprises a DNA molecule homologous or complementary to at least one transgene/genomic junction DNA (SEQ ID NO:1 or SEQ ID NO:2 or SEQ ID NO:3 or SEQ ID NO:4 or SEQ ID NO:5 or SEQ ID NO:6), or a substantial portion thereof. Alternatively, a diagnostic amplicon comprises a DNA molecule homologous or complementary to at least one unique transgene sequence (SEQ ID NO:17 or SEQ ID NO:18 or SEQ ID NO:19 or SEQ ID NO:20 or SEQ ID NO:21 or SEQ ID NO:22 or SEQ ID NO:23).

An analysis for event MON87751 plant tissue sample should include a positive tissue control from event MON87751, a negative control from a soybean plant that is not event MON87751 (for example, but not limited to A3555), and a negative control that contains no soybean genomic DNA. A primer pair that will amplify an endogenous soybean DNA molecule will serve as an internal control for the DNA amplification conditions. Additional primer sequences can be selected from SEQ ID NO:7, SEQ ID NO:8, or SEQ ID NO:9 by those skilled in the art of DNA amplification methods, and conditions selected for the production of an amplicon by the methods shown in Example 4 may differ, but result in an amplicon diagnostic for event MON87751 DNA. The use of these DNA primer sequences with modifications to the methods of Example 4 are within the scope of the invention. The amplicon produced by at least one DNA primer sequence derived from SEQ ID NO:7, SEQ ID NO:8, or SEQ ID NO:9 that is diagnostic for MON87751 is an aspect of the invention.

DNA detection kits contain at least one DNA primer of sufficient length of contiguous nucleotides derived from SEQ ID NO:7, SEQ ID NO:8, or SEQ ID NO:9, that when used in a DNA amplification method produces a diagnostic amplicon for MON87751 or its progeny is an aspect of the invention. A MON87751 soybean plant, plant part, plant cell, seed, or commodity product that will produce an amplicon diagnostic for MON87751 when tested in a DNA amplification method is an aspect of the invention. The assay for the MON87751 amplicon can be performed by using an Applied Biosystems GeneAmp® PCR System 9700 (run at maximum speed) or MJ Research DNA Engine PTC-225 thermal cycler or any other amplification system that can be used to produce an amplicon diagnostic of MON87751 as shown in Example 4.

EXAMPLE 8

To produce soybean plants or plant parts thereof which comprise enhanced agronomic, insecticidal, or herbicidal properties, soybean plants containing event MON87751 are crossed with soybean plants containing potentially any other soybean event or combination thereof and phenotypes are evaluated to determine the resulting properties of the progeny plants. Properties conferred to progeny plants resulting from such plant breeding can extend beyond lepidopteran resistance of event MON87751, including, but not limited to above-ground pest control, herbicide tolerance, nematicidal properties, drought resistance, virus resistance, anti-fungal control, bacteria resistance, male sterility, cold tolerance, salt tolerance, increased yield, enhanced oil composition, increased oil content, enhanced nutrient use efficiency, or altered amino acid content. Examples of transgenic events with improved agronomic traits are well known in the art. Following is a non-limiting list of possible transgenic soybean lines which can be used in breeding with event MON87751 to confer enhanced properties in soybean plants, plant parts, seed, or commodity product. The breeding may include any and all combinations of the following: herbicide tolerance: soybean GTS 40-3-2, MON87708, MON89788, A2704-12, A2704-21, A5547-35, A5547-127, BPS-CV127-9, DP356043, GU262, W62, W98, DAS-44406-6, DAS-68416-4, FG72, BPS-CV127-9, SYHT04R, SYHT0H2, 3560.4.3.5, EE-GM3, pDAB4472-1606, pDAB4468-0416, pDAB8291.45.36, 127, AAD-12; insect resistance: MON87701, DAS-81419-2; increased enhanced oil composition: DP-305423, G94-1, G94-19, G168, OT96-15, MON87705, MON87769; increased yield: MON 87712.

All publications and published patent documents cited in this specification, and which are material to the invention, are incorporated herein by reference to the same extent as if each individual publication or patent application was specifically and individually indicated to be incorporated by reference.

What is claimed is:

1. A recombinant DNA molecule comprising the nucleotide sequence of SEQ ID:17.

2. A method of detecting the presence of a DNA molecule diagnostic for soybean event MON87751 DNA in a sample, said method comprising:
   detecting the presence of the recombinant DNA molecule of claim 1 in said sample.

3. A soybean plant cell comprising the recombinant DNA molecule of claim 1.

4. A soybean plant part comprising the recombinant DNA molecule of claim 1.

5. A soybean plant comprising the recombinant DNA molecule of claim 1.

6. A microorganism comprising the recombinant DNA molecule of claim 1.

7. A method of producing soybean seed comprising crossing the plant of claim 5 with itself or a second soybean plant.

* * * * *

```
                          SEQUENCE LISTING

<160> NUMBER OF SEQ ID NOS: 26

<210> SEQ ID NO 1
    <211> LENGTH: 20
    <212> TYPE: DNA
    <213> ORGANISM: Artificial Sequence
    <220> FEATURE:
    <223> OTHER INFORMATION: Artificial DNA sequence comprising soybean
          genomic sequence and transgene sequence

<400> SEQUENCE: 1
ttggagatct ccagtcagca                                                    20

<210> SEQ ID NO 2
    <211> LENGTH: 20
    <212> TYPE: DNA
    <213> ORGANISM: Artificial Sequence
    <220> FEATURE:
    <223> OTHER INFORMATION: Artificial DNA sequence comprising soybean
          genomic sequence and transgene sequence

<400> SEQUENCE: 2
catgtagatt cctatgagaa                                                    20

<210> SEQ ID NO 3
    <211> LENGTH: 60
    <212> TYPE: DNA
    <213> ORGANISM: Artificial Sequence
    <220> FEATURE:
    <223> OTHER INFORMATION: Artificial DNA sequence comprising soybean
          genomic sequence and transgene sequence

<400> SEQUENCE: 3
tgtagatatt tcccctcact ttggagatct ccagtcagca tcatcacacc aaaagttagg        60

<210> SEQ ID NO 4
    <211> LENGTH: 60
    <212> TYPE: DNA
    <213> ORGANISM: Artificial Sequence
    <220> FEATURE:
    <223> OTHER INFORMATION: Artificial DNA sequence comprising soybean
          genomic sequence and transgene sequence

<400> SEQUENCE: 4
catcatactc attgctgatc catgtagatt cctatgagaa tgagaggaca agacagctcg        60

<210> SEQ ID NO 5
    <211> LENGTH: 100
    <212> TYPE: DNA
    <213> ORGANISM: Artificial Sequence
    <220> FEATURE:
    <223> OTHER INFORMATION: Artificial DNA sequence comprising soybean
          genomic sequence and transgene sequence

<400> SEQUENCE: 5
ttgctctttg gagtttattt tgtagatatt tcccctcact ttggagatct ccagtcagca        60
tcatcacacc aaaagttagg cccgaatagt ttgaaattag                             100
```

<210> SEQ ID NO 6
<211> LENGTH: 100
<212> TYPE: DNA
<213> ORGANISM: Artificial Sequence
<220> FEATURE:
<223> OTHER INFORMATION: Artificial DNA sequence comprising soybean
      genomic sequence and transgene sequence

<400> SEQUENCE: 6 ttcttttttct ccatattgac catcatactc attgctgatc catgtagatt cctatgagaa      60
tgagaggaca agacagctcg gtcaaaactc aatcgtcgaa                            100

<210> SEQ ID NO 7
<211> LENGTH: 1626
<212> TYPE: DNA
<213> ORGANISM: Artificial Sequence
<220> FEATURE:
<223> OTHER INFORMATION: Artificial DNA sequence comprising soybean
      genomic sequence and transgene sequence

<400> SEQUENCE: 7 ttaatttttta agtaaactaa tttatgtcta aagggtttat tttaaaaata ggttaataat      60
aaaatttcat atgatttttt tatcaaacac aaaaattatt taaaattaat ttaaatttaa     120
attaatttta gactaaaaaa taattatca atatgaagcc taatatgtga atattccct       180 atatttacat cttaagtatg tgagttaggt ttactaatat tatatttcat aggtcttttt     240
tgttgatttt atacatattt cttttcatat aaataataac gttttttat cgtaattatt      300 aatttttttat ttttattaac aggaattcga agtcatattt atttctttct cgtttagata    360
gcaacttaat gttatgtatt tccgttaata catttttaaa aaaatttacg atattatgat    420
aagtcatgat caaatacgaa acatacttag tgtaacgtca ttaaattcca tttccatgga    480
atgtgagtac agttcattat ttaatttaat ttttttttg ttgcagaatt taattgacca     540
ggttttgtgg tgacgtctct gcacaggctt cccgtaaggc gtcctaatca taatcttaaa    600
attcttcaat atctaccttg tattttgggt aatgggaaaa tcagactcga tctgtatttt    660
cagttgcaat tctcttcctt ctcgtgactc tccagtacct tgttgatttg aacgacttgg    720
ttaatcttta aattaccttc attaaacatt cgtttgaatt aggtgttaca ttgttaggac    780
cacaacggtg tgacctcaca accttgcgga gttaattatg gtggattggt gggtacatat    840
atagactcat catcaggaac aaaaaatatc tacgaaacca ttatatttat ttttgttgtt    900
tgagactgtc tacatgaatg atacgagact aaagattgtt atttgtcagg aattgtaatt    960 tattttttact acaatataaa caacgagaaa acaacggttg aggttgacat ggtaatcaac   1020
taattgtatt taaaaaaaaa aaaaaaaaca attgtaccat cgtacttggc tcatgagatc    1080
cccacatgct tagatcaggg caatccttaa ctatcactca tgaactcagt cacgacacat    1140
agaggaatag ttagcgaatg tgactcgaac attgcacgac tcccatgaca cctgatatgt    1200
atatatagat ccagatgaga gactcacacg tacatttac tcatcccaat tataaataca     1260
taaacactat agaacaccac taaattgctc tttggagttt attttgtaga tatttcccct    1320
cactttggag atctccagtc agcatcatca caccaaaagt taggcccgaa tagttttgaaa   1380 ttagaaagct cgcaattgag gtctgtcgac cctgcaggta cactggcgcg ccacctcagc    1440
gctgtgcctg ttgcgacaac tattttatg tatgcaagag tcagcatatg tataattgat    1500
tcagaatcgt tttgacgagt tcggatgtag tagtagccat tatttaatgt acatactaat   1560
cgtgaatagt gaatatgatg aaacattgta tcttattgta taaatatcca taaacacatc   1620

```
atgaaa                                                            1626
```

<210> SEQ ID NO 8
<211> LENGTH: 1452
<212> TYPE: DNA
<213> ORGANISM: Artificial Sequence
<220> FEATURE:
<223> OTHER INFORMATION: Artificial DNA sequence comprising soybean
      genomic sequence and transgene sequence

<400> SEQUENCE: 8

```
cgcatcgatc gtgaagtttc tcatctaagc ccccatttgg acgtgaatgt agacacgtcg    60
aaataaagat ttccgaatta gaataatttg tttattgctt tcgcctataa atacgacgga   120
tcgtaatttg tcgttttatc aaaatgtact ttcattttat aataacgctg cggacatcta   180
catttttgaa ttgaaaaaaa attggtaatt actctttctt tttctccata ttgaccatca   240
tactcattgc tgatccatgt agattcctat gagaatgaga ggacaagaca gctcggtcaa   300
aactcaatcg tcgaaattca atgggaacat tttggtatct aacctcaact tcaatactgg   360
agatcggaaa ttccactaac aaggaaatga ccattcgatc ggacctcatc agaactcagt   420
agtaacatat tgtatttgaa agaacaatta aatcatatat aagcttttgt ggaaaaaaag   480
gatactacgt actaaaatat aaacgttgaa gtaaattaca gaaaatgcta atttcataac   540
acggttatct tcaaatttta gtggcccgtt taagccctag ttaaatcaaa tatatgaatg   600
cagtttatgt ataaggtatg catgtgttat agttaatcga gtttagataa ttagaatcaa   660
atatatgatt aatggtacct gtgttacata aagagactaa ttaacctaag ttctgaacaa   720
gtaattaatc aaacattgaa gtgatagatg ttgggcctaa atccagagca taacctttac   780
gtcaatgaac tacaaatttt cacactagaa acatacattg aactttttt ccttcgttta   840
aactcctttt cttttaactg tgtttccgcg tttaatcaaa ttttacgtgt gtcgaccgaa   900
agttagaaat tataactaat aacagactca agttgacgta atttttcat gatacctacg   960
tattgctcgg agtttagatg ctatataaac atgagtgatg acatggtttt aaattgtgct  1020
tccagttgtg ttaccatgaa ctaaaaaatc ttataggtaa ttgtaagaaa atatgattga  1080
tccagtcatg attgcggtta tgatgcgatt gtacagaatc aaaatacctt gaaattgcga  1140
ttgcaattgt tattacagac tccaatttaa aatcatgagt gaggatttta tgatagatcg  1200
aatcaatgtt tcacactaca cctggaataa aaacctgagt cgtttattag atctatatct  1260
tcatatgcat gcatgtacct tagctattca ttttttcactg taaatctta ctcacactta  1320
aaatagtcgt gcatttgata tttgaatgaa atttatagag ctttcgattt gagatagtcc  1380
catctctatt tgggttggtc aatcatggag catgaaaaaa acaatagttt agctaggca   1440
ggccaaatta at                                                     1452
```

<210> SEQ ID NO 9
<211> LENGTH: 10119
<212> TYPE: DNA
<213> ORGANISM: Artificial Sequence
<220> FEATURE:
<223> OTHER INFORMATION: Artificial DNA sequence comprising transgene
      sequence

<400> SEQUENCE: 9

```
ccagtcagca tcatcacacc aaaagttagg cccgaatagt ttgaaattag aaagctcgca    60
attgaggtct gtcgaccctg caggtacact ggcgcgccac ctcagcgctg tgcctgttgc   120
gacaactatt tttatgtatg caagagtcag catatgtata attgattcag aatcgttttg   180
```

```
acgagttcgg atgtagtagt agccattatt taatgtacat actaatcgtg aatagtgaat      240
atgatgaaac attgtatctt attgtataaa tatccataaa cacatcatga aagacacttt      300
ctttcacggt ctgaattaat tatgatacaa ttctaataga aaacgaatta aattacgttg      360
aattgtatga aatctaattg aacaagccaa ccacgacgac gactaacgtt gcctggattg      420
actcggttta agttaaccac taaaaaaacg gagctgtcat gtaacacgcg gatcgagcag      480
gtcacagtca tgaagccatc aaagcaaaag aactaatcca agggctgaga tgattaatta      540
gtttaaaaat tagttaacac gagggaaaag gctgtctgac agccaggtca cgttatcttt      600
acctgtggtc gaaatgattc gtgtctgtcg attttaatta ttttttttgaa aggccgaaaa      660 taaagttgta agagataaac ccgcctatat aaattcatat attttctctc cgctttgaat      720
tgtctcgttg tcctcctcac tttcatcggc cgttttttgaa tctccggcga cttgacagag      780
aagaacaagg aagaagacta agagagaaag taagagataa tccaggagat tcattctccg      840
ttttgaatct tcctcaatct catcttcttc cgctctttct ttccaaggta ataggaactt      900
tctggatcta ctttatttgc tggatctcga tcttgttttc tcaatttcct tgagatttgg      960
aattcgttta atttggatct gtgaacctcc actaaatctt ttggttttac tagaatcgat    1020
ctaagttgac cgatcagtta gctcgattat agctaccaga atttggcttg accttgatgg    1080
agagatccat gttcatgtta cctgggaaat gatttgtata tgtgaattga aatctgaact    1140
gttgaagtta gattgaatct gaacactgtc aatgttagat tgaatctgaa cactgtttaa    1200
ggttagatga agtttgtgta tagattcttc gaaactttag gatttgtagt gtcgtacgtt    1260
gaacagaaag ctatttctga ttcaatcagg gtttatttga ctgtattgaa ctcttttttgt    1320 gtgtttgcag cagatctaca atggcgcaag ttagcagaat ctgcaatggt gtgcagaacc    1380
catctcttat ctccaatctc tcgaaatcca gtcaacgcaa atctccctta tcggtttctc    1440
tgaagacgca gcagcatcca cgagcttatc cgatttcgtc gtcgtgggga ttgaagaaga    1500
gtgggatgac gttaattggc tctgagcttc gtcctcttaa ggtcatgtct tctgtttcca    1560
cggcgtgcat gcttgccatg gataactcag ttttgaacag tgggagaact acaatctgtg    1620
atgcttataa cgtggcagct catgacccctt ttctttttca gcacaagagt cttgatactg    1680
tccaaaagga gtggacagaa tggaaaaaga ataaccactc tctttacttg gaccctattg    1740
tgggtactgt cgcctccttc ctccttaaaa agttggatc actcgttgga aagagaattt    1800
tgagtgagtt gagaaatctt attttcccctt caggatctac caatttgatg caagacattc    1860
tcagggagac tgaaaaattt ctcaaccaga ggcttaacac tgcacccctc gccagagtga    1920
atgctgagct tactggcttg caagctaatg ttgaggagtt taacaggcaa gtcgataatt    1980
tcctcaatcc aaacagaaac gctgtgcccc tcagcataac ttcatcagtg aacactatgc    2040
aacaactgtt tttgaataga ttgccccagt ttcagatgca aggttaccaa ctcctcttgc    2100
ttccactctt cgcccaggct gctaacctgc atctcagttt tatcagggat gtgatttga    2160 atgctgatga gtgggggatt tcagctgcca cccttaggac ctaccgcgat tatctcaaaa    2220
actacactag ggactactct aattactgca ttaacactta tcagagcgct tcaagggac    2280 ttaataccag actgcacgac atgctcgagt ttaggactta catgtttctg aatgttttcg    2340
agtacgtcag tatttggagt cttttcaagt atcagtcact ccttgttagc agcggtgcta    2400
acttgtacgc ttctgggtca gggccccagc agactcagag cttacaagc caggattggc    2460 ccttcctgta ttctctgttt caagtgaata gtaattacgt gttgaacggt ttctccgggg    2520
```

```
ctaggctgtc aaatacctttt cccaacattg tgggacttcc tggatctact accactcacg    2580
ctctcctggc agctagggtt aattattctg gcggcattag tagcggagat attggggctt    2640
ctccattcaa tcagaatttc aactgttcta cttttcttcc tccactcctt actcccttcg    2700
ttagatcctg gttggatagt gggtctgata gagagggcgt cgccaccgtt acaaactggc    2760
aaaccgaatc ctttgaaaca acactcggac ttaggtctgg cgctttcaca gctagaggaa    2820
attccaatta ctttcctgat tattttatta ggaacataag tggcgttcca ctcgttgtta    2880
ggaatgagga cctgaggaga cctcttcatt acaacgaaat aagaaacatc gcatctccat    2940
caggcacccc tggcggagct agggcttata tggtttccgt gcataataga aagaacaaca    3000
ttcatgctgt ccacgagaat ggatcaatga ttcacctggc tcccaacgac tataccgggt    3060
ttactatttc acctattcac gccacacaag tcaacaatca gacaaggacc ttcatttccg    3120
agaaattcgg aaatcagggg gacagtctga gattcgagca gaataacact accgcaagat    3180
atactcttag aggaaatgga aattcttaca acttgtactt gagggtgagc tcaatcggca    3240
attcaacaat cagagttact attaacggca gggtgtatac tgcaacaaac gtcaacacta    3300
ctacaaacaa tgatggcgtt aatgataacg gagcaaggtt ctcagatatt aacattggga    3360
atgttgtcgc aagttccaat tcagatgtgc cccttgatat taacgtgaca cttaattcag    3420
gcacccaatt tgacttgatg aacataatgc tggtgcccac aaatatctca ccactctact    3480
aataaggcca aggcgatcta tgactgaatt gccaatgcac cagcctgtct acatgatgaa    3540
taaataaaga gtccatccag tgtgatggct catgcctgtg tgagtgtgac tgaatccatc    3600
agtgtgtgtg tgtgtttgtg tcaaccatgt gtgaatcagg tgtcaaaaat cgtggctgga    3660
aatccatgtg gtttctagct ttatgtaaat gttgtttgtg aaatataaat attgttttgt    3720
gtatgtgaat tttactctct cattttttctc ttgcactcac cattctatta tagtaatttt    3780
tttaatcgcc agcagaacac gcgctgaggc aaatcctacc acctcatttg caaatttatt    3840
atgtgttttt tttccgtggt cgagattgtg tattattctt tagttattac aagactttta    3900
gctaaaattt gaaagaattt actttaagaa aatcttaaca tctgagataa tttcagcaat    3960
agattatatt tttcattact ctagcagtat ttttgcagat caatcgcaac atatatggtt    4020
gttagaaaaa atgcactata tatatatata ttattttttc aattaaaagt gcatgatata    4080
taatatatat atatatatat atgtgtgtgt gtatatggtc aaagaaattc ttatacaaat    4140
atacacgaac acatatattt gacaaaatca agtattaca ctaaacaatg agttggtgca     4200
tggccaaaac aaatatgtag attaaaaatt ccagcctcca aaaaaaaatc caagtgttgt    4260
aaagcattat atatatatag tagatcccaa attttttgtac aattccacac tgatcgaatt    4320
tttaaagttg aatatctgac gtaggatttt tttaatgtct tacctgacca tttactaata    4380
acattcatac gttttcattt gaaatatcct ctataattat attgaatttg gcacataata    4440
agaaacctaa ttggtgattt attttactag taaatttctg gtgatgggct ttctactaga    4500
aagctctcgg aaaatcttgg accaaatcca tattccatga cttcgattgt taaccctatt    4560
agttttcaca acatactat caatatcatt gcaacggaaa aggtacaagt aaaacattca     4620
atccgatagg gaagtgatgt aggaggttgg gaagacaggc ccagaaagag atttatctga    4680
cttgttttgt gtatagtttt caatgttcat aaaggaagat ggagacttga gaagtttttt    4740
ttggactttg tttagctttg ttgggcgttt ttttttttga tcaataactt tgttgggctt    4800
atgatttgta atatttcgt ggactcttta gtttatttag acgtgctaac tttgttgggc     4860
ttatgacttg ttgtaacata ttgtaacaga tgacttgatg tgcgactaat cttacacat    4920
```

```
taaacatagt tctgttttt  gaaagttctt attttcattt ttatttgaat gttatatatt   4980
tttctatatt tataattcta gtaaaaggca aattttgctt ttaaatgaaa aaaatatata   5040
ttccacagtt tcacctaatc ttatgcattt agcagtacaa attcaaaaat ttcccatttt   5100
tattcatgaa tcataccatt atatattaac taaatccaag gtaaaaaaaa ggtatgaaag   5160
ctctatagta agtaaaatat aaattcccca taaggaaagg gccaagtcca ccaggcaagt   5220
aaaatgagca agcaccactc caccatcaca caatttcact catagataac gataagattc   5280
atggaattat cttccacgtg gcattattcc agcggttcaa gccgataagg gtctcaacac   5340
ctctccttag gcctttgtgg ccgttaccaa gtaaaattaa cctcacacat atccacactc   5400
aaaatccaac ggtgtagatc ctagtccact tgaatctcat gtatcctaga ccctccgatc   5460
actccaaagc ttgttctcat tgttgttatc attatatata gatgaccaaa gcactagacc   5520
aaacctcagt cacacaaaga gtaaagaaga acaatggctt cctctatgct ctcttccgct   5580
actatggttg cctctccggc tcaggccact atggtcgctc ctttcaacgg acttaagtcc   5640
tccgctgcct tcccagccac ccgcaaggct aacaacgaca ttacttccat cacaagcaac   5700
ggcggaagag ttaactgcat gcaggtgtgg cctccgattg gaaagaagaa gtttgagact   5760
ctctcttacc ttcctgacct taccgattcc ggtggtcgcg tcaactgcat gcaggccatg   5820
gacaacaacc caaacatcaa cgaatgcatt ccatcaaact gcttgagtaa cccagaagtt   5880
gaagtacttg gtggagaacg cattgaaacc ggttacactc ccatcgacat ctccttgtcc   5940
ttgacacagt ttctgctcag cgagttcgtg ccaggtgctg ggttcgttct cggactagtt   6000
gacatcatct ggggtatctt tggtccatct caatgggatg cattcctggt gcaaattgag   6060
cagttgatca accagaggat cgaagagttc gccaggaacc aggccatctc taggttggaa   6120
ggattgagca atctctacca aatctatgca gagagcttca gagagtggga agccgatcct   6180
actaacccag ctctccgcga ggaaatgcgt attcaattca acgacatgaa cagcgccttg   6240
accacagcta tcccattgtt cgcagtccag aactaccaag ttcctctctt gtccgtgtac   6300
gttcaagcag ctaatcttca cctcagcgtg cttcgagacg ttagcgtgtt tgggcaaagg   6360
tggggattcg atgctgcaac catcaatagc cgttacaacg accttactag gctgattgga   6420
aactacaccg accacgctgt tcgttggtac aacactggct tggagcgtgt ctggggtcct   6480
gattctagag attggattag atacaaccag ttcaggagaa aattgaccct cacagttttg   6540
gacattgtgt ctctcttccc gaactatgac tccagaacct accctatccg tacagtgtcc   6600
caacttacca gagaaatcta tactaaccca gttcttgaga acttcgacgg tagcttccgt   6660
ggttctgccc aaggtatcga aggctccatc aggagcccac acttgatgga catcttgaac   6720
agcataacta tctacaccga tgctcacaga ggagagtatt actggtctgg acaccagatc   6780
atggcctctc cagttggatt cagcgggccc gagtttacct ttcctctcta tggaactatg   6840
ggaaacgccg ctccacaaca acgtatcgtt gctcaactag gtcagggtgt ctacagaacc   6900
ttgtcttcca ccttgtacag aagacccttc aatatcggta tcaacaacca gcaactttcc   6960
gttcttgacg gaacagagtt cgcctatgga acctcttcta acttgccatc cgctgtttac   7020
agaaagagcg gaaccgttga ttccttggac gaaatcccac cacagaacaa caatgtgcca   7080
cccaggcaag gattctccca caggttgagc cacgtgtcca tgttccgttc cggattcagc   7140
aacagttccg tgagcatcat cagagctcct atgttctctt ggatacaccg tagtgctgag   7200
ttcaacaaca tcattgcatc cgacagcatt actcaaatac ccttggtgaa agcacataca   7260
```

```
cttcagtcag gtactactgt tgtcagaggt ccagggttta caggaggaga cattcttcgt    7320
cgcacaagtg gaggacccTT tgcttacact attgttaaca tcaatggcca attgccccaa    7380
aggtatcgtg caagaatccg ctatgcctct actacaaatc tcaggatcta cgtgactgtt    7440
gcaggtgaaa ggatctttgc tggtcagttc aacaagacta tggataccgg tgacccttTG    7500
acattccaat cttttagcta cgcaactatc aacacagctt ttacattccc aatgagccag    7560
agtagcttca cagtaggtgc tgacactttc agctcaggga tgaagtttta catcgacagg    7620
tttgaattga ttccagttac tgcaaccctc gaggctgagt acaaccttga gagagcccag    7680
aaggctgtga cgccctctt tacctccacc aatcagcttg gcttgaaaac taacgttact    7740
gactatcaca ttgaccaagt gtccaacttg gtcacctacc ttagcgatga gttctgcctc    7800
gacgagaagc gtgaactctc cgagaaagtt aaacacgcca agcgtctcag cgacgagagg    7860
aatctcttgc aagactccaa cttcaaagac atcaacaggc agccagaacg tggttggggt    7920
ggaagcaccg ggatcaccat ccaaggaggc gacgatgtgt tcaaggagaa ctacgtcacc    7980
ctctccggaa ctttcgacga gtgctaccct acctacttgt accagaagat cgatgagtcc    8040
aaactcaaag ccttcaccag gtatcaactt agaggctaca tcgaagacag ccaagaccTT    8100
gaaatctact cgatcaggta caatgccaag cacgagaccg tgaatgtccc aggtactggt    8160
tccctctggc cactttctgc ccaatctccc attgggaagt gtggagagcc taacagatgc    8220
gctccacacc ttgagtggaa tcctgacttg gactgctcct gcagggatgg cgagaagtgt    8280
gcccaccatt ctcatcactt ctccttggac atcgatgtgg gatgtactga cctgaatgag    8340 gacctcgag tctgggtcat cttcaagatc aagacccaag acggacacgc aagacttggc    8400
aaccttgagt ttctcgaaga gaaaccattg gtcggtgaag ctctcgctcg tgtgaagaga    8460
gcagagaaga agtggaggga caaacgtgag aaactcgaat gggaaactaa catcgtttac    8520
aaggaggcca agagtccgt ggatgctttg ttcgtgaact cccaatatga tcagttgcaa    8580
gccgacacca acatcgccat gatccacgcc gcagacaaac gtgtgcacag cattcgtgag    8640
gcttacttgc ctgagttgtc cgtgatccct ggtgtgaacg ctgccatctt cgaggaactt    8700
gagggacgta tctttaccgc attctccttg tacgatgcca gaaacgtcat caagaacggt    8760
gacttcaaca atggcctcag ctgctggaat gtgaaaggtc atgtggacgt ggaggaacag    8820
aacaatcagc gttccgtcct ggttgtgcct gagtgggaag ctgaagtgtc ccaagaggtt    8880
agagtctgtc caggtagagg ctacattctc cgtgtgaccg cttacaagga gggatacggt    8940
gagggttgcg tgaccatcca cgagatcgag aacaacaccg acgagcttaa gttctccaac    9000
tgcgtcgagg aagaaatcta tcccaacaac accgttactt gcaacgacta cactgtgaat    9060
caggaagagt acggaggtgc ctacactagc cgtaacagag gttacaacga agctccttcc    9120
gttcctgctg actatgcctc cgtgtacgag gagaaatcct acacagatgg cagacgtgag    9180
aacccttgcg agttcaacag aggttacagg gactacacac cacttccagt tggctatgtt    9240
accaaggagc ttgagtactt tcctgagacc gacaaagtgt ggatcgagat cggtgaaacc    9300
gagggaaccT tcatcgtgga cagcgtggag cttctcttga tggaggaata atgagcaagg    9360
aggatcatga acatcacaaa gtgaatttat tttatgtttg caccatatat tattatttgt    9420
gacacatttt agaactctta aaccattttt ctgtttgcat tttagctact ggttgttgta    9480
ttcacaataa tgatgcagtc ctatgcttct tggtgtaaga ttcaatacta tgtaaagtgt    9540
atgtctttgg ttgtatacta tttaaaatct attcttgtat tgtataattt attttagcct    9600
ttgtttgaga ttgaggttac ttgttctgtt gcatttaatc acaagttttc attttgttat    9660
```

```
acgtacgtgt tataccctgt ttttggacct aaaaatactg ggcccaattt catttcaaac      9720
tttgtcaatt atcaaatttc aactgcacag ttcacaaata gagtgaggtt gatttgcggc      9780
cgcacgtcct gcttggccta ctaggccaac gcaggcgctg ccgtgacgg ccacgagcga       9840 actaggcctt gggccgcatc gatcgtgaag tttctcatct aagcccccat ttggacgtga      9900
atgtagacac gtcgaaataa agatttccga attagaataa tttgtttatt gctttcgcct      9960
ataaatacga cggatcgtaa tttgtcgttt tatcaaaatg tactttcatt ttataataac     10020
gctgcggaca tctacatttt tgaattgaaa aaaaattggt aattactctt tcttttctc      10080 catattgacc atcatactca ttgctgatcc atgtagatt                             10119
```

<210> SEQ ID NO 10
<211> LENGTH: 12640
<212> TYPE: DNA
<213> ORGANISM: Artificial Sequence
<220> FEATURE:
<223> OTHER INFORMATION: Artificial DNA sequence comprising soybean
      genomic sequence and transgene sequence

<400> SEQUENCE: 10

```
ttaattttta agtaaactaa tttatgtcta aagggtttat tttaaaaata ggttaataat        60
aaaatttcat atgattttt tatcaaacac aaaaattatt taaaattaat ttaaatttaa       120
attaatttta gactaaaaaa taattatca atatgaagcc taatatgtga atattacct        180 atatttacat cttaagtatg tgagttaggt ttactaatat tatatttcat aggtctttt       240 tgttgatttt atacatattt cttttcatat aaataataac gtttttttat cgtaattatt      300
aattttttat tttattaac aggaattcga agtcatattt atttctttct cgtttagata       360
gcaacttaat gttatgtatt tccgttaata cattttaaa aaaatttacg atattatgat       420
aagtcatgat caaatacgaa acatacttag tgtaacgtca ttaaattcca tttccatgga      480
atgtgagtac agttcattat ttaatttaat tttttttttg ttgcagaatt taattgacca      540
ggttttgtgg tgacgtctct gcacaggctt cccgtaaggc gtcctaatca taatcttaaa      600
attcttcaat atctaccttg tattttgggt aatgggaaaa tcagactcga tctgtatttt      660
cagttgcaat tctcttcctt ctcgtgactc tccagtacct tgttgatttg aacgacttgg      720 ttaatctta aattaccttc attaaacatt cgtttgaatt aggtgttaca ttgttaggac       780
cacaacggtg tgacctcaca accttgcgga gttaattatg gtggattggt gggtacatat      840
atagactcat catcaggaac aaaaaatatc tacgaaacca ttatatttat ttttgttgtt      900
tgagactgtc tacatgaatg atacgagact aaagattgtt atttgtcagg aattgtaatt      960
tatttttact acaatataaa caacgagaaa acaacggtt aggttgacat ggtaatcaac      1020
taattgtatt taaaaaaaa aaaaaaaaca attgtaccat cgtacttggc tcatgagatc      1080
cccacatgct tagatcaggg caatccttaa ctatcactca tgaactcagt cacgacacat     1140
agaggaatag ttagcgaatg tgactcgaac attgcacgac tcccatgaca cctgatatgt     1200
atatatagat ccagatgaga gactcacacg tacattttac tcatcccaat tataaataca     1260
taaacactat agaacaccac taaattgctc tttggagttt atttgtaga tatttccct       1320 cactttggag atctccagtc agcatcatca caccaaaagt taggcccgaa tagtttgaaa     1380
ttagaaagct cgcaattgag gtcgtcgac cctgcaggta cactggcgcg ccacctcagc      1440
gctgtgcctg ttgcgacaac tatttttatg tatgcaagag tcagcatatg tataattgat     1500
tcagaatcgt tttgacgagt tcggatgtag tagtagccat tatttaatgt acatactaat     1560
```

```
cgtgaatagt gaatatgatg aaacattgta tcttattgta taaatatcca taaacacatc    1620
atgaaagaca ctttctttca cggtctgaat taattatgat acaattctaa tagaaaacga    1680
attaaattac gttgaattgt atgaaatcta attgaacaag ccaaccacga cgacgactaa    1740
cgttgcctgg attgactcgg tttaagttaa ccactaaaaa aacggagctg tcatgtaaca    1800
cgcggatcga gcaggtcaca gtcatgaagc catcaaagca aaagaactaa tccaagggct    1860
gagatgatta ttagtttaa aaattagtta acacgaggga aaaggctgtc tgacagccag    1920
gtcacgttat ctttacctgt ggtcgaaatg attcgtgtct gtcgatttta attatttttt    1980
tgaaaggccg aaaataaagt tgtaagagat aaacccgcct atataaattc atatattttc    2040
tctccgcttt gaattgtctc gttgtcctcc tcactttcat cggccgtttt tgaatctccg    2100
gcgacttgac agagaagaac aaggaagaag actaagagag aaagtaagag ataatccagg    2160
agattcattc tccgttttga atcttcctca atctcatctt cttccgctct ttctttccaa    2220
ggtaatagga actttctgga tctactttat ttgctggatc tcgatcttgt tttctcaatt    2280
tccttgagat ttggaattcg tttaatttgg atctgtgaac ctccactaaa tcttttggtt    2340
ttactagaat cgatctaagt tgaccgatca gttagctcga ttatagctac cagaatttgg    2400
cttgaccttg atggagagat ccatgttcat gttacctggg aaatgatttg tatatgtgaa    2460
ttgaaatctg aactgttgaa gttagattga atctgaacac tgtcaatgtt agattgaatc    2520
tgaacactgt ttaaggttag atgaagtttg tgtatagatt cttcgaaact ttaggatttg    2580
tagtgtcgta cgttgaacag aaagctattt ctgattcaat cagggtttat ttgactgtat    2640
tgaactcttt ttgtgtgttt gcagcagatc tacaatggcg caagttagca gaatctgcaa    2700
tggtgtgcag aacccatctc ttatctccaa tctctcgaaa tccagtcaac gcaaatctcc    2760
cttatcggtt tctctgaaga cgcagcagca tccacgagct tatccgattt cgtcgtcgtg    2820
gggattgaag aagagtggga tgacgttaat tggctctgag cttcgtcctc ttaaggtcat    2880
gtcttctgtt tccacggcgt gcatgcttgc catggataac tcagttttga acagtgggag    2940
aactacaatc tgtgatgctt ataacgtggc agctcatgac cctttttctt ttcagcacaa    3000
gagtcttgat actgtccaaa aggagtggac agaatggaaa aagaataacc actctcttta    3060
cttggaccct attgtgggta ctgtcgcctc cttcctcctt aaaaaagttg gatcactcgt    3120
tggaaagaga atttttgagtg agttgagaaa tcttattttc ccttcaggat ctaccaattt    3180
gatgcaagac attctcaggg agactgaaaa atttctcaac cagaggctta acactgacac    3240
cctcgccaga gtgaatgctg agcttactgg cttgcaagct aatgttgagg agtttaacag    3300
gcaagtcgat aatttcctca atccaaacag aaacgctgtg cccctcagca taacttcatc    3360
agtgaacact atgcaacaac tgttttgaa tagattgccc cagtttcaga tgcaaggtta    3420
ccaactcctc ttgcttccac tcttcgccca ggctgctaac ctgcatctca gttttatcag    3480
ggatgtgatt ttgaatgctg atgagtgggg gatttcagct gccaccctta ggacctaccg    3540
cgattatctc aaaaactaca ctagggacta ctctaattac tgcattaaca cttatcagag    3600
cgctttcaag ggacttaata ccagactgca cgacatgctc gagtttagga cttacatgtt    3660
tctgaatgtt ttcgagtacg tcagtatttg gagtcttttc aagtatcagt cactccttgt    3720
tagcagcggt gctaacttgt acgcttctgg gtcagggccc cagcagactc agagctttac    3780
aagccaggat tggcccttcc tgtattctct gtttcaagtg aatagtaatt acgtgttgaa    3840
cggtttctcc ggggctaggc tgtcaaatac ctttcccaac attgtgggac ttcctggatc    3900
```

-continued

```
tactaccact cacgctctcc tggcagctag ggttaattat tctggcggca ttagtagcgg      3960
agatattggg gcttctccat tcaatcagaa tttcaactgt tctactttc ttcctccact       4020
ccttactccc ttcgttagat cctggttgga tagtgggtct gatagagagg gcgtcgccac      4080
cgttacaaac tggcaaaccg aatcctttga acaacactc ggacttaggt ctggcgcttt       4140
cacagctaga ggaaattcca attactttcc tgattatttt attaggaaca taagtggcgt      4200
tccactcgtt gttaggaatg aggacctgag gagacctctt cattacaacg aaataagaaa      4260
catcgcatct ccatcaggca ccctggcgg agctagggct tatatggttt ccgtgcataa       4320
tagaaagaac aacattcatg ctgtccacga gaatggatca atgattcacc tggctcccaa      4380
cgactatacc gggtttacta tttcacctat tcacgccaca caagtcaaca atcagacaag      4440
gaccttcatt tccgagaaat tcggaaatca ggggacagt ctgagattcg agcagaataa       4500
cactaccgca agatatactc ttagaggaaa tggaaattct tacaacttgt acttgagggt      4560
gagctcaatc ggcaattcaa caatcagagt tactattaac ggcagggtgt atactgcaac      4620
aaacgtcaac actactacaa acaatgatgg cgttaatgat aacggagcaa ggttctcaga      4680
tattaacatt gggaatgttg tcgcaagttc caattcagat gtgcccctg atattaacgt       4740
gacacttaat tcaggcaccc aatttgactt gatgaacata atgctggtgc ccacaaatat      4800
ctcaccactc tactaataag gccaaggcga tctatgactg aattgccaat gcaccagcct      4860
gtctacatga tgaataaata aagagtccat ccagtgtgat ggctcatgcc tgtgtgagtg      4920
tgactgaatc catcagtgtg tgtgtgtgtt tgtgtcaacc atgtgtgaat caggtgtcaa      4980
aaatcgtggc tggaaatcca tgtggtttct agctttatgt aaatgttgtt tgtgaaatat      5040
aaatattgtt ttgtgtatgt gaattttact ctctcatttt tctcttgcac tcaccattct      5100
attatagtaa tttttttaat cgccagcaga acacgcgctg aggcaaatcc taccacctca      5160
tttgcaaatt tattatgtgt ttttttccg tggtcgagat tgtgtattat tctttagtta       5220
ttacaagact tttagctaaa atttgaaaga atttacttta agaaaatctt aacatctgag      5280
ataatttcag caatagatta tattttcat tactctagca gtattttgc agatcaatcg        5340
caacatatat ggttgttaga aaaatgcac tatatatata tatattattt ttcaattaa        5400
aagtgcatga tatataatat atatatatat atatatgtgt gtgtgtatat ggtcaaagaa      5460
attcttatac aaatatacac gaacacatat atttgacaaa atcaaagtat tacactaaac      5520
aatgagttgg tgcatggcca aaacaaatat gtagattaaa aattccagcc tccaaaaaaa      5580
aatccaagtg ttgtaaagca ttatatatat atagtagatc ccaaattttt gtacaattcc      5640
acactgatcg aatttttaaa gttgaatatc tgacgtagga ttttttttaat gtcttacctg    5700
accatttact aataacattc atcgttttc atttgaaata tcctctataa ttatattgaa       5760
tttggcacat aataagaaac ctaattggtg atttatttta ctagtaaatt tctggtgatg      5820
ggctttctac tagaaagctc tcggaaaatc ttggaccaaa tccatattcc atgacttcga      5880
ttgttaaccc tattagtttt cacaaacata ctatcaatat cattgcaacg aaaaggtac       5940
aagtaaaaca ttcaatccga tagggaagtg atgtaggagg ttgggaagac aggcccagaa      6000
agagatttat ctgacttgtt ttgtgtatag ttttcaatgt tcataaagga agatgggagac     6060
ttgagaagtt ttttttggac tttgtttagc tttgttgggc gttttttttt ttgatcaata     6120
actttgttgg gcttatgatt tgtaatattt tcgtggactc tttagtttat ttagacgtgc     6180
taactttgtt gggcttatga cttgttgtaa catattgtaa cagatgactt gatgtgcgac      6240
taatctttac acattaaaca tagttctgtt ttttgaaagt tcttattttc atttttattt     6300
```

```
gaatgttata tatttttcta tatttataat tctagtaaaa ggcaaatttt gcttttaaat    6360
gaaaaaaata tatattccac agtttcacct aatcttatgc atttagcagt acaaattcaa    6420
aaatttccca tttttattca tgaatcatac cattatatat taactaaatc caaggtaaaa    6480
aaaaggtatg aaagctctat agtaagtaaa atataaattc cccataagga aagggccaag    6540
tccaccaggc aagtaaaatg agcaagcacc actccaccat cacacaattt cactcataga    6600
taacgataag attcatggaa ttatcttcca cgtggcatta ttccagcggt tcaagccgat    6660
aagggtctca acacctctcc ttaggccttt gtggccgtta ccaagtaaaa ttaacctcac    6720
acatatccac actcaaaatc caacggtgta gatcctagtc cacttgaatc tcatgtatcc    6780
tagaccctcc gatcactcca aagcttgttc tcattgttgt tatcattata tatagatgac    6840
caaagcacta gaccaaacct cagtcacaca aagagtaaag aagaacaatg gcttcctcta    6900
tgctctcttc cgctactatg gttgcctctc cggctcaggc cactatggtc gctccttttca   6960 acggacttaa gtcctccgct gccttcccag ccacccgcaa ggctaacaac gacattactt    7020
ccatcacaag caacggcgga agagttaact gcatgcaggt gtggcctccg attggaaaga    7080
agaagtttga gactctctct taccttcctg accttaccga ttccggtggt cgcgtcaact    7140
gcatgcaggc catggacaac aacccaaaca tcaacgaatg cattccatac aactgcttga    7200
gtaacccaga agttgaagta cttggtggag aacgcattga aaccggttac actcccatcg    7260
acatctcctt gtccttgaca cagtttctgc tcagcgagtt cgtgccaggt gctgggttcg    7320
ttctcggact agttgacatc atctggggta tctttggtcc atctcaatgg gatgcattcc    7380
tggtgcaaat tgagcagttg atcaaccaga ggatcgaaga gttcgccagg aaccaggcca    7440
tctctaggtt ggaaggattg agcaatctct accaaatcta tgcagagagc ttcagagagt    7500
gggaagccga tcctactaac ccagctctcc gcgaggaaat gcgtattcaa ttcaacgaca    7560 tgaacgcgc cttgaccaca gctatcccat tgttcgcagt ccagaactac caagttcctc    7620
tcttgtccgt gtacgttcaa gcagctaatc ttcacctcag cgtgcttcga gacgttagcg    7680
tgtttgggca aaggtgggga ttcgatgctg caaccatcaa tagccgttac aacgaccta    7740 ctaggctgat tggaaactac accgaccacg ctgttcgttg gtacaacact ggcttggagc    7800
gtgtctgggg tcctgattct agagattgga ttagatacaa ccagttcagg agagaattga    7860
ccctcacagt tttggacatt gtgtctctct cccgaactaa tgactccaga acctacccta    7920
tccgtacagt gtcccaactt accagagaaa tctatactaa cccagttctt gagaacttcg    7980
acggtagctt ccgtggttct gcccaaggta tcgaaggctc catcaggagc ccacacttga    8040
tggacatctt gaacagcata actatctaca ccgatgctca cagaggagag tattactggt    8100
ctggacacca gatcatggcc tctccagttg gattcagcgg gccgagtttt accttcctc     8160 tctatggaac tatgggaaac gccgctccac aacaacgtat cgttgctcaa ctaggtcagg    8220
gtgtctacag aaccttgtct tccaccttgt acagaagacc cttcaatatc ggtatcaaca    8280
accagcaact ttccgttctt gacggaacag agttcgccta tggaacctct tctaacttgc    8340
catccgctgt ttacagaaag agcggaaccg ttgattcctt ggacgaaatc ccaccacaga    8400
acaacaatgt gccacccagg caaggattct cccacaggtt gagccacgtg tccatgttcc    8460
gttccggatt cagcaacagt tccgtgagca tcatcagagc tcctatgttc tcttggatac    8520
accgtagtgc tgagttcaac aacatcattg catccgacag cattactcaa ataccccttgg   8580 tgaaagcaca tacacttcag tcaggtacta ctgttgtcag aggtccaggg tttacaggag    8640
```

```
gagacattct tcgtcgcaca agtggaggac cctttgctta cactattgtt aacatcaatg    8700
gccaattgcc ccaaaggtat cgtgcaagaa tccgctatgc ctctactaca aatctcagga    8760
tctacgtgac tgttgcaggt gaaaggatct ttgctggtca gttcaacaag actatggata    8820
ccggtgaccc tttgacattc aatcttttta gctacgcaac tatcaacaca gcttttacat    8880
tcccaatgag ccagagtagc ttcacagtag gtgctgacac tttcagctca gggaatgaag    8940
tttacatcga caggtttgaa ttgattccag ttactgcaac cctcgaggct gagtacaacc    9000
ttgagagagc ccagaaggct gtgaacgccc tctttacctc caccaatcag cttggcttga    9060
aaactaacgt tactgactat cacattgacc aagtgtccaa cttggtcacc taccttagcg    9120
atgagttctg cctcgacgag aagcgtgaac tctccgagaa agttaaacac gccaagcgtc    9180
tcagcgacga gaggaatctc ttgcaagact ccaacttcaa agacatcaac aggcagccag    9240
aacgtggttg gggtggaagc accgggatca ccatccaagg aggcgacgat gtgttcaagg    9300
agaactacgt caccctctcc ggaactttcg acgagtgcta ccctacctac ttgtaccaga    9360
agatcgatga gtccaaactc aaagccttca ccaggtatca acttagaggc tacatcgaag    9420
acagccaaga ccttgaaatc tactcgatca ggtacaatgc caagcacgag accgtgaatg    9480
tcccaggtac tggttccctc tggccacttt ctgcccaatc tcccattggg aagtgtggag    9540
agcctaacag atgcgctcca caccttgagt ggaatcctga cttggactgc tcctgcaggg    9600
atggcgagaa gtgtgcccac cattctcatc acttctcctt ggacatcgat gtgggatgta    9660
ctgacctgaa tgaggacctc ggagtctggg tcatcttcaa gatcaagacc caagacggac    9720
acgcaagact tggcaacctt gagtttctcg aagagaaacc attggtcggt gaagctctcg    9780
ctcgtgtgaa gagagcagag aagaagtgga gggacaaacg tgagaaactc gaatgggaaa    9840
ctaacatcgt ttacaaggag gccaaagagt ccgtggatgc tttgttcgtg aactcccaat    9900
atgatcagtt gcaagccgac accaacatcg ccatgatcca cgccgcagac aaacgtgtgc    9960
acagcattcg tgaggcttac ttgcctgagt tgtccgtgat ccctggtgtg aacgctgcca   10020
tcttcgagga acttgaggga cgtatctttta ccgcattctc cttgtacgat gccagaaacg   10080
tcatcaagaa cggtgacttc aacaatggcc tcagctgctg gaatgtgaaa ggtcatgtgg   10140
acgtggagga acagaacaat cagcgttccg tcctggttgt gcctgagtgg aagctgaag    10200 tgtcccaaga ggttagagtc tgtccaggta gaggctacat tctccgtgtg accgcttaca   10260
aggagggata cggtgagggt tgcgtgacca tccacgagat cgagaacaac accgacgagc   10320
ttaagttctc caactgcgtc gaggaagaaa tctatcccaa caacaccgtt acttgcaacg   10380
actacactgt gaatcaggaa gagtacggag gtgcctacac tagccgtaac agaggttaca   10440
acgaagctcc ttccgttcct gctgactatg cctccgtgta cgaggagaaa tcctacacag   10500
atggcagacg tgagaaccct tgcgagttca acagaggtta cagggactac acaccacttc   10560
cagttggcta tgttaccaag gagcttgagt actttcctga ccgacaaa gtgtggatcg    10620 agatcggtga aaccgaggga accttcatcg tggacagcgt ggagcttctc ttgatggagg   10680
aataatgagc aaggaggatc atgaacatca caaagtgaat ttattttatg tttgcaccat   10740
atattattat ttgtgacaca ttttagaact cttaaaccat ttttctgttt gcattttagc   10800
tactggttgt tgtattcaca ataatgatgc agtcctatgc ttcttggtgt aagattcaat   10860
actatgtaaa gtgtatgtct ttggttgtat actatttaaa atctattctt gtattgtata   10920 atttattta gcctttgttt gagattgagg ttacttgttc tgttgcattt aatcacaagt    10980
tttcattttg ttatacgtac gtgttatacc ctgttttgg acctaaaaat actgggccca   11040
```

```
atttcatttc aaactttgtc aattatcaaa tttcaactgc acagttcaca aatagagtga    11100
ggttgatttg cggccgcacg tcctgcttgg cctactaggc caacgcaggc gctggccgtg    11160
acggccacga gcgaactagg ccttgggccg catcgatcgt gaagtttctc atctaagccc    11220
ccatttggac gtgaatgtag acacgtcgaa ataaagattt ccgaattaga ataatttgtt    11280
tattgctttc gcctataaat acgacggatc gtaatttgtc gttttatcaa aatgtacttt    11340 catttttataa taacgctgcg gacatctaca ttttgaattt gaaaaaaaat tggtaattac    11400
tctttctttt tctccatatt gaccatcata ctcattgctg atccatgtag attcctatga    11460
gaatgagagg acaagacagc tcggtcaaaa ctcaatcgtc gaaattcaat gggaacattt    11520
tggtatctaa cctcaacttc aatactggag atcggaaatt ccactaacaa ggaaatgacc    11580
attcgatcgg acctcatcag aactcagtag taacatattg tatttgaaag aacaattaaa    11640
tcatatataa gcttttgtgg aaaaaaagga tactacgtac taaaatataa acgttgaagt    11700
aaattacaga aaatgctaat ttcataacac ggttatcttc aaattttagt ggcccgttta    11760
agccctagtt aaatcaaata tatgaatgca gtttatgtat aaggtatgca tgtgttatag    11820
ttaatcgagt ttagataatt agaatcaaat atatgattaa tggtacctgt gttacataaa    11880
gagactaatt aacctaagtt ctgaacaagt aattaatcaa acattgaagt gatagatgtt    11940
gggcctaaat ccagagcata acctttacgt caatgaacta caaattttca cactagaaac    12000
atacattgaa cttttttttcc ttcgtttaaa ctccttttct tttaactgtg tttccgcgtt    12060
taatcaaatt ttacgtgtgt cgaccgaaag ttagaaatta aactaataa cagactcaag    12120 ttgacgtaat tttttcatga tacctacgta ttgctcggag tttagatgct atataaacat    12180
gagtgatgac atggttttaa attgtgcttc cagttgtgtt accatgaact aaaaaatctt    12240
ataggtaatt gtaagaaaat atgattgatc cagtcatgat tgcggttatg atgcgattgt    12300
acagaatcaa aataccttga aattgcgatt gcaattgtta ttacagactc caatttaaaa    12360
tcatgagtga ggatttttatg atagatcgaa tcaatgtttc acactacacc tggaataaaa    12420
acctgagtcg tttattagat ctatatcttc atatgcatgc atgtacctta gctattcatt    12480
tttcactgta aatctttact cacacttaaa atagtcgtgc atttgatatt tgaatgaaat    12540
ttatagagct ttcgatttga gatagtccca tctctatttg ggttggtcaa tcatggagca    12600
tgaaaaaaac aatagtttag ctaggccagg ccaaattaat                          12640

<210> SEQ ID NO 11
<211> LENGTH: 27
<212> TYPE: DNA
<213> ORGANISM: Artificial Sequence
<220> FEATURE:
<223> OTHER INFORMATION: Chemically Synthesized Oligonucleotide PCR
      Primer

<400> SEQUENCE: 11
ctctttcttt ttctccatat tgaccat                                          27

<210> SEQ ID NO 12
<211> LENGTH: 26
<212> TYPE: DNA
<213> ORGANISM: Artificial Sequence
<220> FEATURE:
<223> OTHER INFORMATION: Chemically Synthesized Oligonucleotide PCR
      Primer

<400> SEQUENCE: 12
```
ctgtcttgtc ctctcattct catagg                                26

<210> SEQ ID NO 13
<211> LENGTH: 19
<212> TYPE: DNA
<213> ORGANISM: Artificial Sequence
<220> FEATURE:
<223> OTHER INFORMATION: Chemically Synthesized Oligonucleotide PCR
      Probe

<400> SEQUENCE: 13
atactcattg ctgatccat                                        19

<210> SEQ ID NO 14
<211> LENGTH: 24
<212> TYPE: DNA
<213> ORGANISM: Artificial Sequence
<220> FEATURE:
<223> OTHER INFORMATION: Chemically Synthesized Oligonucleotide PCR
      Primer

<400> SEQUENCE: 14
agctgtcttg tcctctcatt ctca                                  24

<210> SEQ ID NO 15
<211> LENGTH: 30
<212> TYPE: DNA
<213> ORGANISM: Artificial Sequence
<220> FEATURE:
<223> OTHER INFORMATION: Chemically Synthesized Oligonucleotide PCR
      Primer

<400> SEQUENCE: 15
ctctttggag tttattttgt agatatttcc                            30

<210> SEQ ID NO 16
<211> LENGTH: 18
<212> TYPE: DNA
<213> ORGANISM: Artificial Sequence
<220> FEATURE:
<223> OTHER INFORMATION: Chemically Synthesized Oligonucleotide PCR
      Probe

<400> SEQUENCE: 16
tcactttgga gatcggag                                         18

<210> SEQ ID NO 17
<211> LENGTH: 112
<212> TYPE: DNA
<213> ORGANISM: Artificial Sequence
<220> FEATURE:
<223> OTHER INFORMATION: Artificial DNA sequence comprising transgene
      sequence

<400> SEQUENCE: 17
atagtttgaa attagaaagc tcgcaattga ggtctgtcga ccctgcaggt acactggcgc    60
gccacctcag cgctgtgcct gttgcgacaa ctatttttat gtatgcaaga gt           112

<210> SEQ ID NO 18
<211> LENGTH: 52
<212> TYPE: DNA
<213> ORGANISM: Artificial Sequence
<220> FEATURE:
<223> OTHER INFORMATION: Artificial DNA sequence comprising transgene
      sequence

<400> SEQUENCE: 18
attgaactct ttttgtgtgt ttgcagcaga tctacaatgg cgcaagttag ca          52

<210> SEQ ID NO 19
<211> LENGTH: 283
<212> TYPE: DNA
<213> ORGANISM: Artificial Sequence
<220> FEATURE:
<223> OTHER INFORMATION: Artificial DNA sequence comprising transgene
      sequence

<400> SEQUENCE: 19
cggcgtgcat gcttgccatg gataactcag ttttgaacag tgggagaact acaatctgtg    60
atgcttataa cgtggcagct catgacccct tttcttttca gcacaagagt cttgatactg   120
tccaaaagga gtggacagaa tggaaaaaga ataaccactc tctttacttg gaccctattg   180
tgggtactgt cgcctccttc ctccttaaaa aagttggatc actcgttgga aagagaattt   240
tgagtgagtt gagaaatctt attttcccct caggatctac caa                    283

<210> SEQ ID NO 20
<211> LENGTH: 486
<212> TYPE: DNA
<213> ORGANISM: Artificial Sequence
<220> FEATURE:
<223> OTHER INFORMATION: Artificial DNA sequence comprising transgene
      sequence

<400> SEQUENCE: 20
gagtacgtca gtatttggag tcttttcaag tatcagtcac tccttgttag cagcggtgct    60
aacttgtacg cttctgggtc agggccccag cagactcaga gctttacaag ccaggattgg   120
cccttcctgt attctctgtt tcaagtgaat agtaattacg tgttgaacgg tttctccggg   180
gctaggctgt caaataccct tcccaacatt gtgggacttc ctggatctac taccactcac   240
gctctcctgg cagctagggt taattattct ggcggcatta gtagcggaga tattggggct   300
tctccattca atcagaattt caactgttct acttttcttc ctccactcct tactcccttc   360
gttagatcct ggttggatag tgggtctgat agagagggcg tcgccaccgt tacaaactgg   420
caaaccgaat cctttgaaac aacactcgga cttaggtctg gcgctttcac agctagagga   480
aattcc                                                              486

<210> SEQ ID NO 21
<211> LENGTH: 179
<212> TYPE: DNA
<213> ORGANISM: Artificial Sequence
<220> FEATURE:
<223> OTHER INFORMATION: Artificial DNA sequence comprising transgene
      sequence

<400> SEQUENCE: 21
taacggagca aggttctcag atattaacat tgggaatgtt gtcgcaagtt ccaattcaga    60
tgtgcccctt gatattaacg tgacacttaa ttcaggcacc caatttgact tgatgaacat   120
aatgctggtg cccacaaata tctcaccact ctactaataa ggccaaggcg atctatgac    179

<210> SEQ ID NO 22
<211> LENGTH: 106
<212> TYPE: DNA
<213> ORGANISM: Artificial Sequence
<220> FEATURE:
<223> OTHER INFORMATION: Artificial DNA sequence comprising transgene
      sequence

```
<400> SEQUENCE: 22
tcttgcactc accattctat tatagtaatt tttttaatcg ccagcagaac acgcgctgag      60
gcaaatccta ccacctcatt tgcaaattta ttatgtgttt tttttc                   106

<210> SEQ ID NO 23
<211> LENGTH: 60
<212> TYPE: DNA
<213> ORGANISM: Artificial Sequence
<220> FEATURE:
<223> OTHER INFORMATION: Artificial DNA sequence comprising transgene
      sequence

<400> SEQUENCE: 23
acagcgtgga gcttctcttg atggaggaat aatgagcaag gaggatcatg aacatcacaa      60

<210> SEQ ID NO 24
<211> LENGTH: 66
<212> TYPE: DNA
<213> ORGANISM: Artificial Sequence
<220> FEATURE:
<223> OTHER INFORMATION: Artificial DNA sequence comprising transgene
      sequence

<400> SEQUENCE: 24
cttgttctgt tgcatttaat cacaagtttt cattttgtta tacgtacgtg ttataccctg      60
tttttg                                                                66

<210> SEQ ID NO 25
<211> LENGTH: 156
<212> TYPE: DNA
<213> ORGANISM: Artificial Sequence
<220> FEATURE:
<223> OTHER INFORMATION: Artificial DNA sequence comprising transgene
      sequence

<400> SEQUENCE: 25
ctttgtcaat tatcaaattt caactgcaca gttcacaaat agagtgaggt tgatttgcgg      60
ccgcacgtcc tgcttggcct actaggccaa cgcaggcgct ggccgtgacg gccacgagcg    120
aactaggcct tgggccgcat cgatcgtgaa gtttct                              156

<210> SEQ ID NO 26
<211> LENGTH: 1905
<212> TYPE: DNA
<213> ORGANISM: Artificial Sequence
<220> FEATURE:
<223> OTHER INFORMATION: Artificial DNA sequence comprising transgene
      sequence

<400> SEQUENCE: 26
atggataact cagttttgaa cagtgggaga actacaatct gtgatgctta taacgtggca      60
gctcatgacc cttttctttt tcagcacaag agtcttgata ctgtccaaaa ggagtggaca    120
gaatggaaaa agaataacca ctctctttac ttggacccta ttgtgggtac tgtcgcctcc    180
ttcctcctta aaaagttgg atcactcgtt ggaaagagaa ttttgagtga gttgagaaat    240
cttattttcc cttcaggatc taccaatttg atgcaagaca ttctcaggga gactgaaaaa    300
tttctcaacc agaggcttaa cactgacacc ctcgccagag tgaatgctga gcttactggc    360
ttgcaagcta atgttgagga gtttaacagg caagtcgata atttcctcaa tccaaacaga    420
aacgctgtgc ccctcagcat aacttcatca gtgaacacta tgcaacaact gttttttgaat    480 agattgcccc agtttcagat gcaaggttac caactcctct tgcttccact cttcgcccag    540
```

```
gctgctaacc tgcatctcag ttttatcagg gatgtgattt tgaatgctga tgagtggggg    600
atttcagctg ccaccctttag gacctaccgc gattatctca aaaactacac tagggactac    660
tctaattact gcattaacac ttatcagagc gctttcaagg gacttaatac cagactgcac    720
gacatgctcg agtttaggac ttacatgttt ctgaatgttt tcgagtacgt cagtatttgg    780
agtcttttca agtatcagtc actccttgtt agcagcggtg ctaacttgta cgcttctggg    840
tcagggcccc agcagactca gagctttaca agccaggatt ggcccttcct gtattctctg    900
tttcaagtga atagtaatta cgtgttgaac ggtttctccg gggctaggct gtcaaatacc    960
tttcccaaca ttgtgggact tcctggatct actaccactc acgctctcct ggcagctagg   1020
gttaattatt ctggcggcat tagtagcgga gatattgggg cttctccatt caatcagaat   1080
ttcaactgtt ctacttttct tcctccactc cttactccct tcgttagatc ctggttggat   1140
agtgggtctg atagagaggg cgtcgccacc gttacaaact ggcaaaccga atcctttgaa   1200
acaacactcg gacttaggtc tggcgctttc acagctagag gaaattccaa ttactttcct   1260
gattatttta ttaggaacat aagtggcgtt ccactcgttg ttaggaatga ggacctgagg   1320
agacctcttc attacaacga aataagaaac atcgcatctc catcaggcac ccctggcgga   1380
gctagggctt atatggtttc cgtgcataat agaaagaaca acattcatgc tgtccacgag   1440
aatggatcaa tgattcacct ggctcccaac gactataccg ggtttactat ttcacctatt   1500
cacgccacac aagtcaacaa tcagacaagg accttcattt ccgagaaatt cggaaatcag   1560
ggggacagtc tgagattcga gcagaataac actaccgcaa gatatactct tagaggaaat   1620
ggaaattctt acaacttgta cttgagggtg agctcaatcg gcaattcaac aatcagagtt   1680
actattaacg gcagggtgta tactgcaaca aacgtcaaca ctactacaaa caatgatggc   1740
gttaatgata acggagcaag gttctcagat attaacattg ggaatgttgt cgcaagttcc   1800
aattcagatg tgccccttga tattaacgtg acacttaatt caggcaccca atttgacttg   1860
atgaacataa tgctggtgcc cacaaatatc tcaccactct actaa                    1905
```